(12) United States Patent
Kwak et al.

(10) Patent No.: US 8,535,814 B2
(45) Date of Patent: Sep. 17, 2013

(54) HETEROCYCLIC COMPOUND AND ORGANIC LIGHT EMITTING DEVICE INCLUDING THE SAME

(75) Inventors: Yoon-Hyun Kwak, Yongin (KR); Seok-Hwan Hwang, Yongin (KR); Young-Kook Kim, Yongin (KR); Hye-Jin Jung, Yongin (KR); Jong-Hyuk Lee, Yongin (KR); Jin-O Lim, Yongin (KR); Hyung-Jun Song, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 325 days.

(21) Appl. No.: 12/854,065

(22) Filed: Aug. 10, 2010

(65) Prior Publication Data

US 2011/0031485 A1    Feb. 10, 2011

(30) Foreign Application Priority Data

Aug. 10, 2009  (KR) ........................ 10-2009-0073521

(51) Int. Cl.
 *H01L 51/54* (2006.01)
 *C09K 11/06* (2006.01)
 *C07D 487/04* (2006.01)

(52) U.S. Cl.
 USPC ............. 428/690; 428/917; 313/504; 257/40; 548/418

(58) Field of Classification Search
 None
 See application file for complete search history.

(56) References Cited

U.S. PATENT DOCUMENTS

| | | | |
|---|---|---|---|
| 2,675,380 A | 4/1954 | Fielden et al. | |
| 5,153,073 A | 10/1992 | Ohnuma et al. | |
| 5,843,607 A | 12/1998 | Hu et al. | |
| 5,942,340 A | 8/1999 | Hu et al. | |
| 5,952,115 A * | 9/1999 | Hu et al. | 428/690 |
| 6,951,693 B2 | 10/2005 | Hosokawa et al. | |
| 2005/0287396 A1* | 12/2005 | Nakamura et al. | 428/690 |
| 2006/0043858 A1 | 3/2006 | Ikeda et al. | |
| 2007/0237984 A1 | 10/2007 | Matsuura et al. | |
| 2008/0122344 A1 | 5/2008 | Shin et al. | |
| 2008/0124455 A1 | 5/2008 | Shin et al. | |
| 2008/0268284 A1 | 10/2008 | Kawakami et al. | |
| 2009/0017330 A1 | 1/2009 | Iwakuma et al. | |
| 2009/0230852 A1 | 9/2009 | Lee et al. | |
| 2009/0242876 A1 | 10/2009 | Brunner et al. | |
| 2009/0295276 A1* | 12/2009 | Asari et al. | 313/504 |
| 2009/0302752 A1 | 12/2009 | Parham et al. | |
| 2011/0031484 A1 | 2/2011 | Lee et al. | |
| 2011/0037063 A1 | 2/2011 | Buesing et al. | |
| 2011/0253944 A1 | 10/2011 | Han et al. | |

FOREIGN PATENT DOCUMENTS

| | | |
|---|---|---|
| EP | 1 375 624 A1 | 1/2004 |
| EP | 1 650 208 A1 | 4/2006 |
| EP | 2 145 936 A2 | 1/2010 |
| EP | 2 202 283 A1 | 6/2010 |
| JP | 06-322361 | 11/1994 |
| JP | 11-162650 | 6/1999 |
| JP | 11-167215 | 6/1999 |
| JP | 11-176578 | 7/1999 |
| JP | 2000-156290 | 6/2000 |
| JP | 2000-229974 | 8/2000 |
| JP | 2001-011436 | 1/2001 |
| JP | 2005-048004 | 2/2005 |
| JP | 2005-289921 | 10/2005 |
| JP | 2007088016 A * | 4/2007 |
| JP | 4025136 B2 | 10/2007 |
| JP | 4041816 B2 | 2/2008 |
| JP | 2008-071863 | 3/2008 |
| JP | 2008-078362 | 4/2008 |
| JP | 2008-214306 | 9/2008 |
| JP | 2010-073987 | 4/2010 |
| JP | 2010-087408 | 4/2010 |
| JP | 2011-037854 | 2/2011 |
| KR | 10-2001-0015513 A | 2/2001 |
| KR | 10-2006-0051609 | 5/2006 |
| KR | 10-2007-0067612 | 6/2007 |
| KR | 10-2007-0091643 | 9/2007 |
| KR | 10-2008-0018573 A | 2/2008 |
| KR | 10-2008-0025933 | 3/2008 |
| KR | 10-2008-0047210 | 5/2008 |
| KR | 10-2008-0063234 A | 7/2008 |
| KR | 10-2008-0084979 | 9/2008 |

(Continued)

OTHER PUBLICATIONS

Machine translation of JP2010-087408. Date of publication: Apr. 15, 2012.*

(Continued)

*Primary Examiner* — Gerard Higgins
*Assistant Examiner* — Andrew K Bohaty
(74) *Attorney, Agent, or Firm* — Christie, Parker & Hale, LLP

(57) ABSTRACT

Embodiments of the present invention are directed to heterocyclic compound and an organic light-emitting device including the heterocyclic compound. The heterocyclic compound is represented by Formula 1.

Formula 1

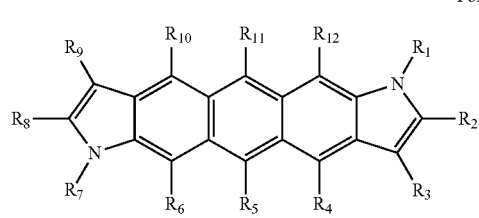

17 Claims, 1 Drawing Sheet

(56) References Cited

FOREIGN PATENT DOCUMENTS

| KR | 10-2008-0095749 A | 10/2008 |
|---|---|---|
| KR | 10-0901887 B1 | 6/2009 |
| KR | 10-2011-0016033 | 2/2011 |
| WO | WO 2007/046246 A1 | 4/2007 |
| WO | WO 2007063796 A1 * | 6/2007 |
| WO | WO 2008/086851 A1 | 7/2008 |
| WO | WO 2009/008099 A1 | 1/2009 |
| WO | WO 2009/127307 A1 | 10/2009 |
| WO | WO 2010/074520 A2 | 7/2010 |

OTHER PUBLICATIONS

Machine translation of JP2007-088016. Date of publication: Apr. 5, 2007.*
KIPO Office action dated Apr. 25, 2011, for Korean priority Patent application 10-2009-0073521, noting listed reference in this IDS.
Registration Determination Certificate dated Nov. 30, 2011 issued in Korean Application No. 10-2009-0073521, 5 pages.
European Search Report dated Apr. 12, 2011, for corresponding European Patent application 10172324.5, noting Category X reference listed in this IDS.
English machine translation of Claim 1 for Japanese Publication 2010-087408 listed above, 2 pages.
U.S. Office action dated Aug. 17, 2002, for cross reference U.S. Appl. No. 12/853,224, (16 pages).
European Search Report dated Nov. 18, 2000, for European Patent application 10172343.5, (6 pages).
European Search Report dated Feb. 24, 2011, for European Patent application 10172343.5, (19 pages).
Kipo Registration Determination Certificate dated Dec. 29, 2011, for Korean Patent application 10-2009-0073522, (5 pages).
Lin et al., "The First Synthesis of Optically Pure Biscarbazoles and Determination of their Absolute Configurations", Tetrahedron Letters, (1999), vol. 40, Shanghai Institute of Organic Chemistry, Chinese Academy of Science, pp. 341-344, XP-4152547.
Kosolapoff et al., "Reaction of Phenylmagnesium Bromide and Diphenylmagnesium with 9,10-Diphenylacridyl Chloride and ρ-Dimethylaminotriphenylmethyl chloride", The Department of Chemistry, University of Michigan, Journal received Oct. 19, 1953, vol. 76, pp. 1276-1278, XP-002622434.
Liu et al., "Analysis of Water-Soluble Products from the Mild Oxidation of Longkou Brown Coal with $H_2O_2$", American Chemical Society, Journal, (2003), vol. 17, No. 2, 1 page, XP-002622435.
Buu-Hoi, et al., "Carcinogenic nitrogen compounds. XXXV. Some heterocyclic derivitaves of pyrene", Journal of the Chemical Society, Journal, (1963), 3 pages, XP-002622436.
Paek, et al., "Blue Organic Light Emitting Compound Having Excellent Thermal Stability and Organic Light Emitting Diode Comprising the Same", Neo View Co., Lt., S. Korea, Rep of Korean Kongkae Taeho Kongbo, 4 pages, XP-002622437.
Thomas, et al, "Improved host material design for phosphorescent guest-host systems", Thin Solid Films, (2003), vol. 436, pp. 264-268, XP-4434523.
Japanese Office action dated Dec. 4, 2012, for corresponding Japanese Patent application 2010-132059, (4 pages).

* cited by examiner

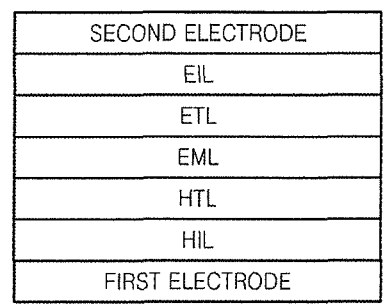

HETEROCYCLIC COMPOUND AND ORGANIC LIGHT EMITTING DEVICE INCLUDING THE SAME

CROSS-REFERENCE TO RELATED PATENT APPLICATION

This application claims priority to and the benefit of Korean Patent Application No. 10-2009-0073521, filed on Aug. 10, 2009, in the Korean Intellectual Property Office, the entire content of which is incorporated herein by reference.

BACKGROUND OF THE INVENTION

1. Field of the Invention

The present invention relates to a heterocyclic compound and an organic light-emitting device including the heterocyclic compound.

2. Description of the Related Art

Organic light-emitting devices are self-emission type display devices and have wide viewing angles, high contrast ratios, and short response times. Due to these characteristics, organic light-emitting devices are drawing more attention.

Such organic light-emitting devices can be roughly classified into inorganic light-emitting devices which include emission layers containing inorganic compounds, and organic light-emitting devices which include emission layers containing organic compounds. Organic light-emitting devices have higher luminance, lower driving voltages, and shorter response times than inorganic light-emitting devices, and can render multi-colored displays. In addition, organic light-emitting devices produce various colors. Thus, much research into such organic light-emitting devices has been conducted.

Typically, an organic light-emitting device has a stack structure including an anode, a cathode and an organic emission layer between the anode and cathode. However, a hole injection layer and/or a hole transport layer may be further stacked between the anode and the organic emission layer, and/or an electron transport layer may be further stacked between the organic emission layer and the cathode. In other words, an organic light-emitting device may have an anode/hole transport layer/organic emission layer/cathode structure or an anode/hole transport layer/organic emission layer/electron transport layer/cathode structure.

As the material for forming the hole transport layer, polyphenyl compounds or anthracene derivatives can be used. However, organic light-emitting devices including hole injection layers and/or hole transport layers formed of such materials do not have satisfactory life span, efficiency, and power consumption characteristics, thus leaving much room for improvement.

SUMMARY OF THE INVENTION

According to embodiments of the present invention, a heterocyclic compound imparts improved electrical characteristics, charge transporting capabilities and light-emission capabilities.

In some embodiments of the present invention, an organic light-emitting device includes the heterocyclic compound.

According to other embodiments of the present invention, a flat panel display device includes the organic light-emitting device.

In still other embodiments of the present invention, an organic light-emitting device comprises at least one layer containing the heterocyclic compound, where the at least one layer is formed using a wet process.

According to embodiments of the present invention, a heterocyclic compound is represented by Formula 1 below:

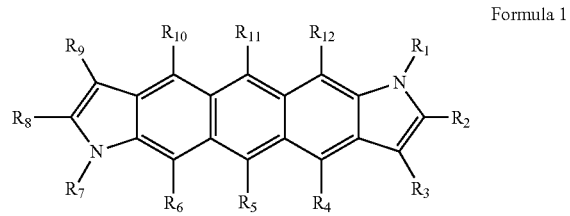

Formula 1

In Formula 1, each of $R_1$ through $R_{12}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_1$ through $R_{12}$ may optionally bond to each other, thereby forming an aromatic ring.

According to embodiments of the present invention, each of $R_1$ and $R_7$ is independently selected from monocyclic to tetracyclic aryl groups, $C_{12}$-$C_{50}$ arylamine groups, monocyclic to tetracyclic aryl groups, and $C_{12}$-$C_{50}$ arylamine groups. Nonlimiting examples of suitable monocyclic to tetracyclic aryl groups or $C_{12}$-$C_{50}$ arylamine groups include unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups. Nonlimiting examples of suitable monocyclic to tetracyclic aryl groups include phenyl groups, naphthyl groups, biphenyl groups, terphenyl groups, anthracenyl groups, fluorenyl groups, carbazolyl groups, and pyrenyl groups, each of which may be substituted with a $C_1$-$C_5$ alkyl group. Other nonlimiting examples of suitable monocyclic to tetracyclic aryl groups include $C_1$-$C_5$ alkoxy groups, cyano groups, amine groups, phenoxy groups, phenyl groups, naphthyl groups, and halogen groups. Nonlimiting examples of suitable $C_{12}$-$C_{50}$ arylamine groups include those substituted with at least one $C_1$-$C_5$ alkyl group, $C_1$-$C_4$ alkoxy group, cyano group, amine group, phenoxy group, phenyl group, or halogen group.

In some embodiments, $R_1$ and $R_7$ are the same, $R_2$, $R_3$, $R_8$ and $R_9$ are the same, or R5 and R11 are the same.

Each of $R_2$, $R_3$, $R_8$ and $R_9$ may be independently selected from methyl groups and phenyl groups.

Each of $R_5$ and $R_{11}$ may be independently selected from t-butyl groups, phenyl groups, naphthyl groups, and fluorenyl groups.

The heterocyclic compound may include one of Compounds 11, 29, 43, 56, 74 and 82 below:
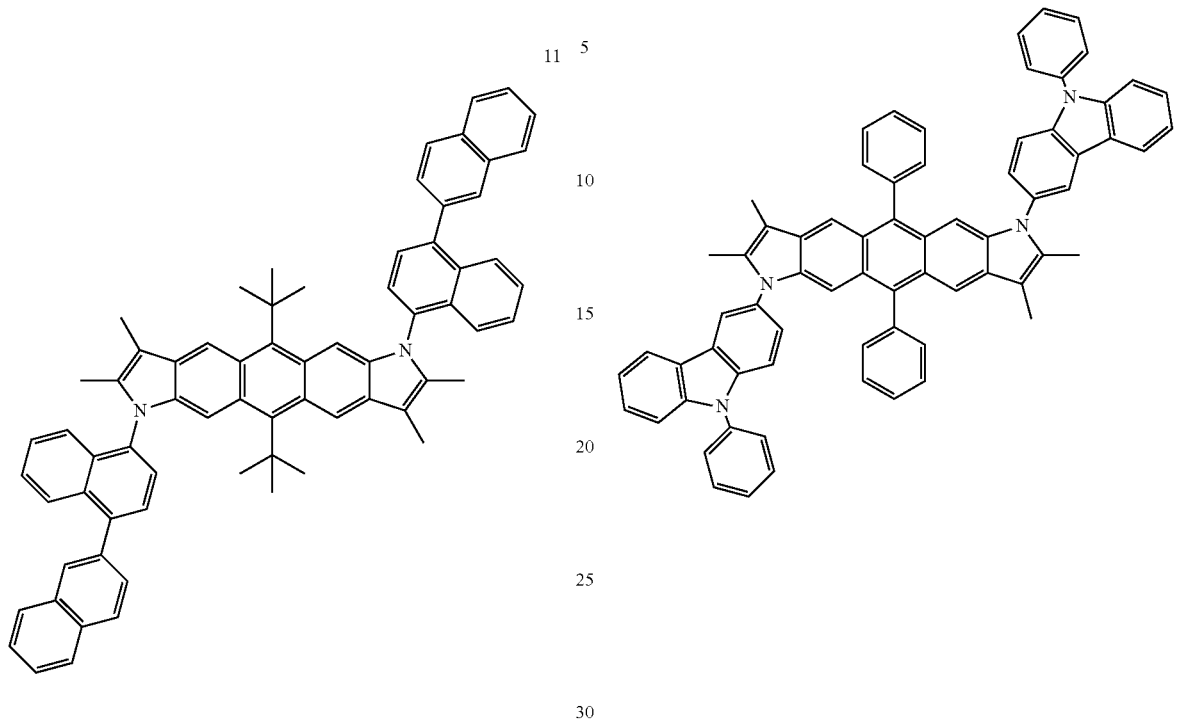
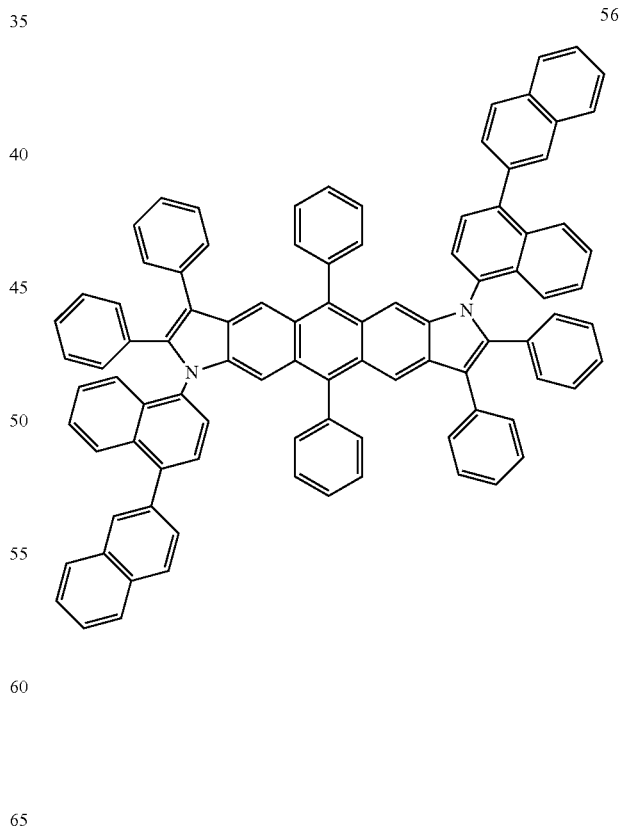

-continued

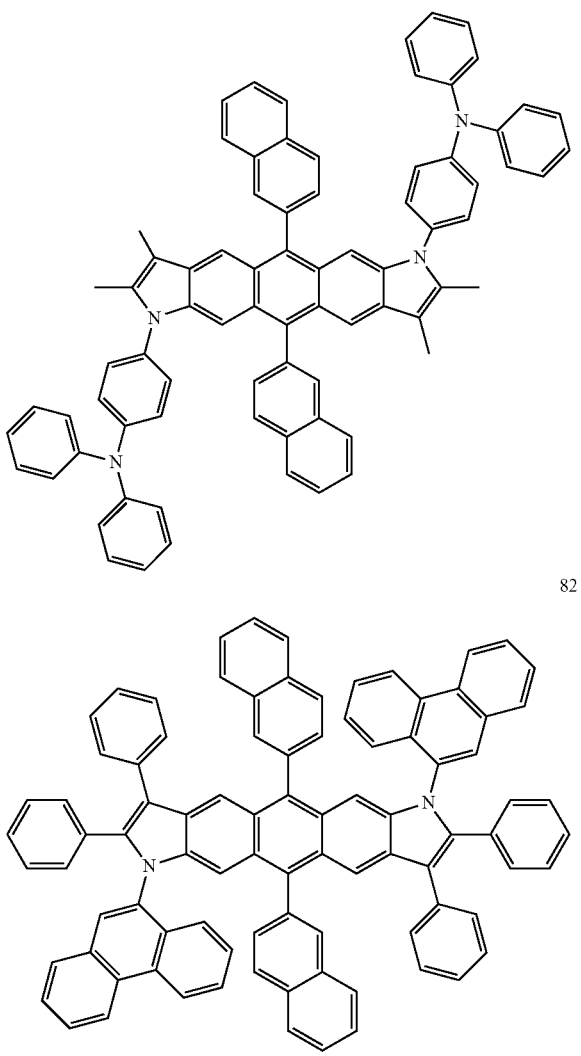

According to embodiments of the present invention, an organic light-emitting device includes a first electrode, a second electrode, and an organic layer between the first electrode and the second electrode, wherein the organic layer includes the heterocyclic compound described above.

According to other embodiments of the present invention, the organic layer may include a hole injection layer or a hole transport layer.

According to still other embodiments of the present invention, the organic layer may include a single film having both electron injection and electron transport functions.

According to yet other embodiments of the present invention, the organic layer may include an emission layer.

According to embodiments of the present invention, the organic layer may include an emission layer, and the heterocylic compound may be a fluorescent or phosphorescent host.

According to embodiments of the present invention, the organic layer may include an emission layer, and the heterocylic compound may be a fluorescent dopant.

According to embodiments of the present invention, the organic layer may include an emission layer, an electron injection layer, or an electron transport layer, and the emission layer may include an anthracene compound.

According to embodiments of the present invention, the organic layer may include an emission layer, an electron injection layer or an electron transport layer, and the emission layer may include an arylamine compound.

According to embodiments of the present invention, the organic layer may include an emission layer, an electron injection layer or an electron transport layer, and the emission layer may include a styryl compound.

According to embodiments of the present invention, the organic layer may include an emission layer, an electron injection layer or an electron transport layer, and the emission layer may include a red emission layer, a green emission layer, a blue emission layer or a white emission layer that includes a phosphorescent compound.

According to embodiments of the present invention, the organic layer may include at least one layer selected from a hole injection layer, a hole transport layer, an electron blocking layer, an emission layer, a hole blocking layer, an electron transport layer, and an electron injection layer.

According to embodiments of the present invention, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

According to embodiments of the present invention, a flat panel display device includes the organic light-emitting device described above, wherein the first electrode of the organic light-emitting device is electrically connected to a source electrode or a drain electrode of a thin-film transistor.

According to embodiments of the present invention, an organic light-emitting device includes a first electrode, a second electrode, and an organic layer between the first electrode and the second electrode, wherein the organic layer includes at least one layer comprising the heterocyclic compound described above, the at least one layer being formed using a wet process.

BRIEF DESCRIPTION OF THE DRAWING

The above and other features and advantages of the present invention will become more apparent by reference to the following detailed description when considered in conjunction with the attached drawing in which:

FIG. 1 is a diagram of the structure of an organic light-emitting device according to an embodiment of the present invention.

DETAILED DESCRIPTION OF THE INVENTION

The present invention will now be described with reference to the accompanying drawings, in which exemplary embodiments of the invention are shown.

A heterocyclic compound according to embodiments of the present invention is represented by Formula 1 below:

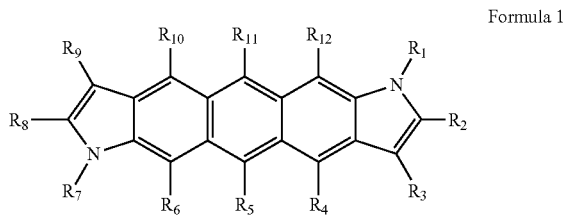

Formula 1

In Formula 1, each of $R_1$ through $R_{12}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_1$ through $R_{12}$ may optionally bond to each other, thereby forming an aromatic ring.

Anthracene derivatives have been used as materials for the organic emission layer. For example, organic light-emitting devices have been manufactured using phenylanthracene dimer or trimer compounds. However, such organic light-emitting devices have narrow energy gaps and lower blue-light color purity since two or three oligomeric species of anthracene are linked by conjugation. In addition, such compounds are highly vulnerable to oxidation and thus are liable to produce impurities, necessitating purification.

In an effort overcome these drawbacks, organic light-emitting devices manufactured using anthracene compounds such as naphthalene substituted for anthracene at the 1,9 positions or diphenylanthracene compounds including an aryl group substituted for a phenyl group at the m-position have been introduced. However, these organic light-emitting devices have lower light-emission efficiency.

In addition, organic light-emitting devices have been manufactured using naphthalene-substituted monoanthracene derivatives. However, the light-emission efficiency of such devices is low at about 1 cd/A, and thus such organic light-emitting devices are not suitable for practical use.

Furthermore, organic light-emitting devices have been manufactured using phenylanthracene compounds including an aryl substituent at the m-position. Such compounds have good thermal resistance but lead to low light-emission efficiency of about 2 cd/A. Thus, further improvement is required.

The heterocyclic compounds of Formula 1 according to embodiments of the present invention may be suitable as a material for an emission layer and/or a charge transport layer or charge injection layer of an organic light-emitting device. The heterocyclic compounds of Formula 1 have high glass transition temperatures (Tg) or melting points due to the introduction of the heterocyclic group. Thus, the heterocyclic compound has thermal resistance against Joule's heat generated in an organic layer, between organic layers, or between an organic layer and a metallic electrode when light emission occurs, and has high durability in high-temperature environments.

An organic light-emitting device manufactured using the heterocyclic compound of Formula 1 (which includes an amine ring fused to a fluorene group) has good durability when stored or operated. In addition, due to the introduction of a substituent such as a fluorene group or a naphthyl group, molecular layers formed as thin films may be maintained in good condition, thereby improving the characteristics of the organic light-emitting device.

Substituents in the heterocyclic compound of Formula 1 will now be described. Each of $R_1$ through $R_7$ may be independently selected from monocyclic to tetracyclic aryl groups, $C_{12}$-$C_{50}$ arylamine groups, substituted monocyclic to tetracyclic aryl groups, and substituted $C_{12}$-$C_{50}$ arylamine groups. Nonlimiting examples of suitable monocyclic to tetracyclic aryl groups and $C_{12}$-$C_{50}$ arylamine groups include unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups. Nonlimiting examples of suitable substituted monocyclic to tetracyclic aryl groups include phenyl groups, naphthyl groups, biphenyl groups, terphenyl groups, anthracenyl groups, fluorenyl groups, carbazolyl groups, and pyrenyl groups substituted with at least one $C_1$-$C_5$ alkyl group, $C_1$-$C_5$ alkoxy group, cyano group, amine group, phenoxy group, phenyl group, naphthyl group, or halogen group. Nonlimiting examples of suitable substituted $C_{12}$-$C_{50}$ arylamine groups include those substituted with at least one $C_1$-$C_5$ alkyl group, $C_1$-$C_4$ alkoxy groups, cyano group, amine group, phenoxy group, phenyl group, or halogen group.

In the heterocyclic compound, $R_1$ and $R_7$ may be identical to each other, $R_2$, $R_3$, $R_8$ and $R_9$ may be identical to each other, or $R_5$ and $R_{11}$ may be identical to each other. Thus, some substituents of the heterocyclic compound of Formula 1 may be symmetric to each other, or all the substituents of the heterocyclic compound of
Formula 1 may be symmetric to each other.

In some embodiments, in Formula 1, each of $R_2$, $R_3$, $R_8$ and $R_9$ may be independently selected from methyl groups and phenyl groups.

In some embodiments, in Formula 1, each of $R_5$ and $R_{11}$ may be independently selected from t-butyl groups, phenyl groups, naphthyl groups, and fluorenyl groups.

Substituents described with reference to Formula 1 will now be described. The unsubstituted $C_1$-$C_{50}$ alkyl group used herein may be linear or branched. Nonlimiting examples of the alkyl group may include methyl groups, ethyl groups, propyl groups, isobutyl groups, sec-butyl groups, pentyl groups, iso-amyl groups, hexyl groups, heptyl groups, octyl groups, nonanyl groups, and dodecyl groups. At least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_3$-$C_{50}$ cycloalkyl group refers to a $C_3$-$C_{50}$ alkyl group having a cyclic form. In the unsubstituted $C_3$-$C_{50}$ alkyl group, one or more hydrogen atoms may be substituted with a substituent such as those described with reference to the unsubstituted $C_1$-$C_{30}$ alkyl group.

The unsubstituted $C_1$-$C_{50}$ alkoxy group used herein is a group having a —OA structure in which A is an unsubstituted $C_1$-$C_{50}$ alkyl group as described above. Nonlimiting examples thereof include methoxy groups, ethoxy groups, propoxy groups, isopropyloxy groups, butoxy groups, and pentoxy groups. At least one hydrogen atom of the alkoxy group may be substituted with a substituent group such as those previously described with respect to the alkyl groups.

The unsubstituted $C_6$-$C_{60}$ aryl group used herein refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent such as those described with reference to the unsubstituted $C_1$-$C_{50}$ alkyl group.

Nonlimiting examples of the substituted or unsubstituted $C_6$-$C_{30}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-toryl groups, o-, m-, and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$ heteroaryl group used herein includes one, two or three hetero atoms selected from N, O, P and S. If the unsubstituted $C_4$-$C_{60}$ heteroaryl group has at least two rings, the rings may be fused to each other or linked to each other by a single bond.

Nonlimiting examples of the unsubstituted $C_4$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. In addition, at least one hydrogen atom in the heteroaryl group may be substituted with a substituent such as those described with reference to the unsubstituted $C_1$-$C_{50}$ alkyl group.

The unsubstituted $C_5$-$C_{50}$ aryloxy group is represented by —$OA_1$ where $A_1$ may be a $C_5$-$C_{60}$ aryl group. Nonlimiting examples of the aryloxy group include phenoxy groups. At least one hydrogen atom in the aryl group may be substituted with a substituent such as those described with reference to the unsubstituted $C_1$-$C_{50}$ alkyl group.

The unsubstituted $C_5$-$C_{50}$ arylthiol group is represented by —$SA_1$ where $A_1$ may be a $C_5$-$C_{60}$ aryl group. Nonlimiting examples of the arylthiol group include phenylthiol groups, naphthylthiol groups, and fluorenylthiol groups. At least one hydrogen atom in the arylthiol group may be substituted with a substituent such as those described with reference to the unsubstituted $C_1$-$C_{50}$ alkyl group.

The unsubstituted $C_6$-$C_{60}$ condensed polycyclic group used herein refers to a substituent including at least two rings, where at least one aromatic ring and/or at least one non-aromatic ring are fused to each other. The unsubstituted $C_6$-$C_{60}$ condensed polycyclic group may include some of the substituents described with reference to the aryl group or the heteroaryl group.

The heterocyclic compound of Formula 1 may be synthesized through the following reaction scheme.

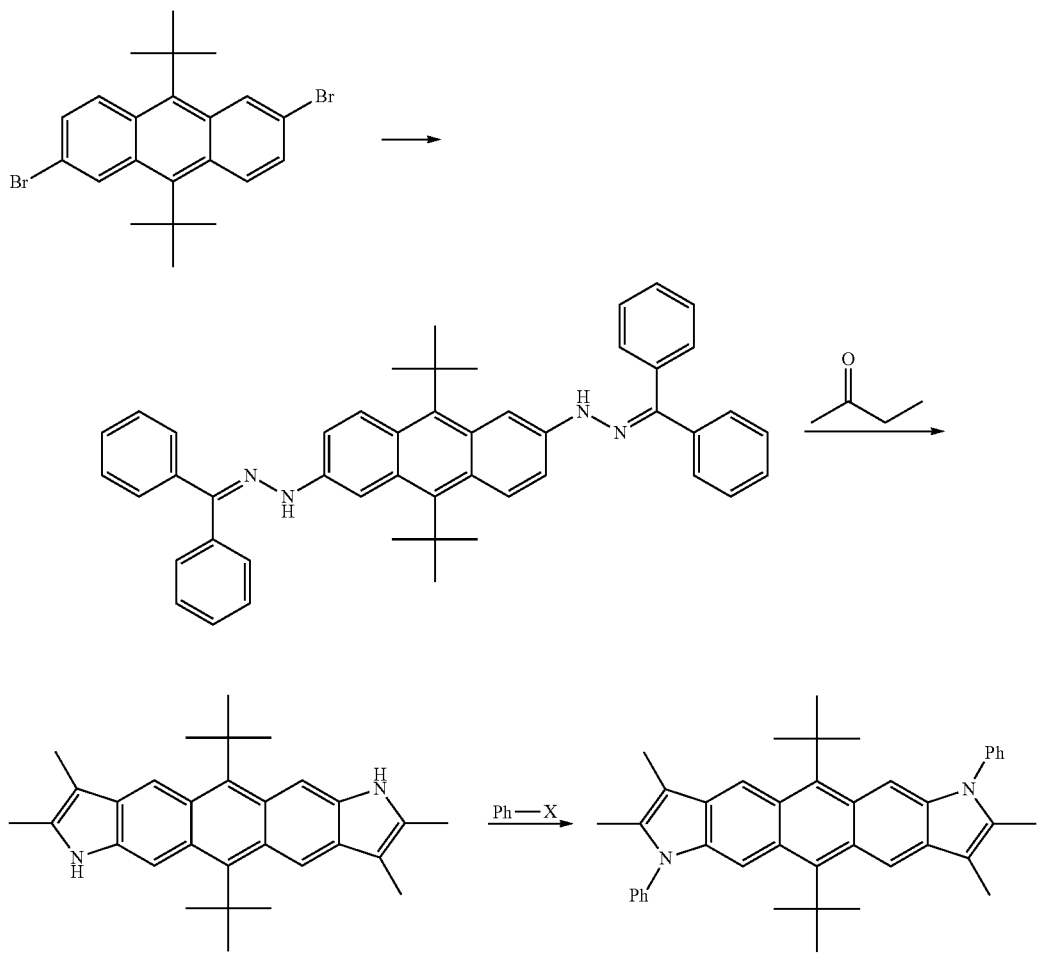

compound 1

Nonlimiting examples of heterocyclic compounds satisfying Formula 1 according to embodiments of the present invention include Compounds 1 through 120 represented below.
1
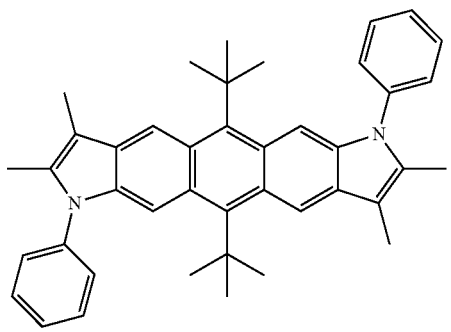
2
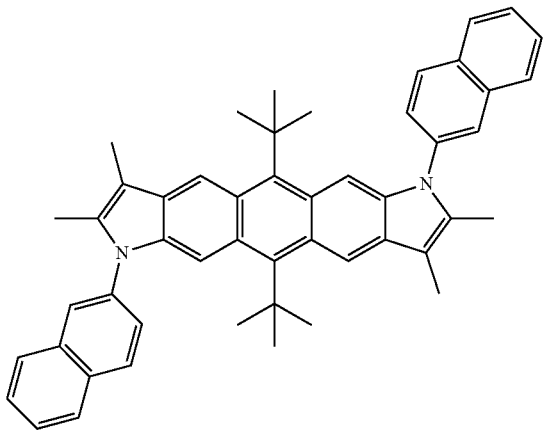
3
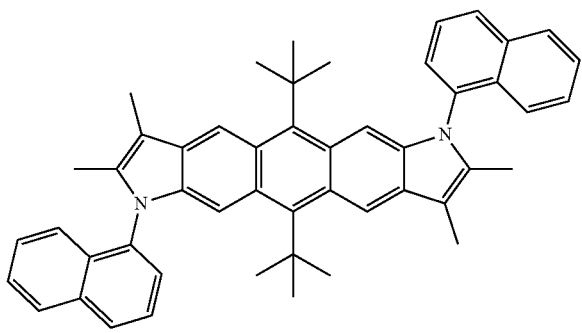
4
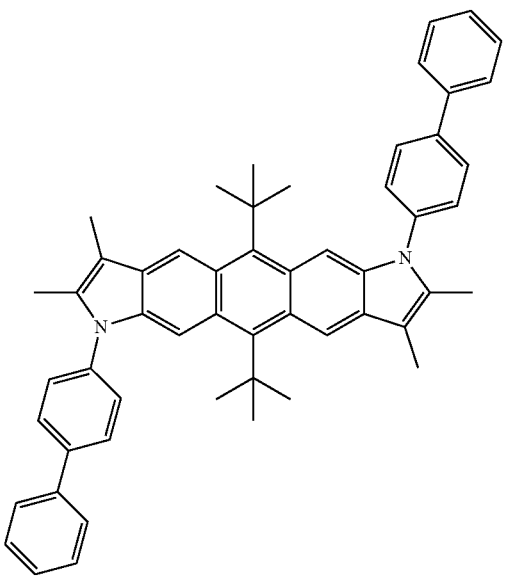
5
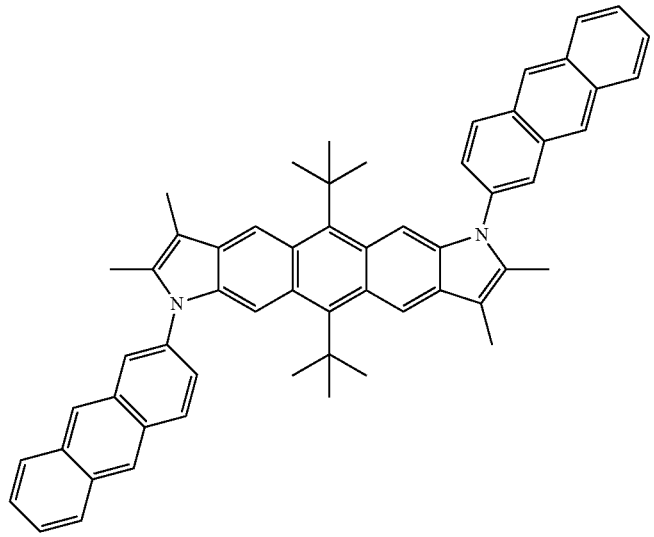

-continued
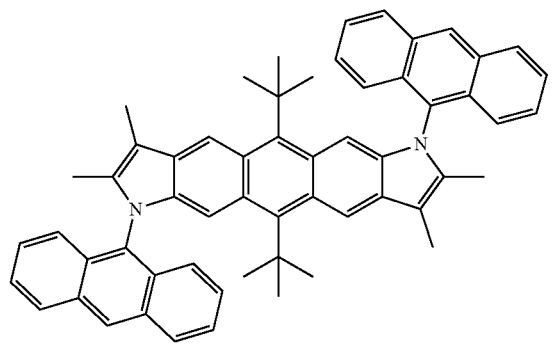
6
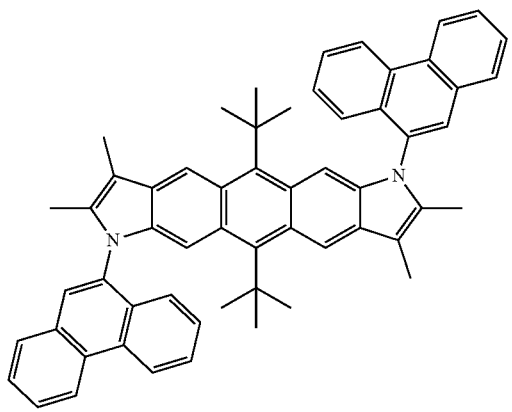
7
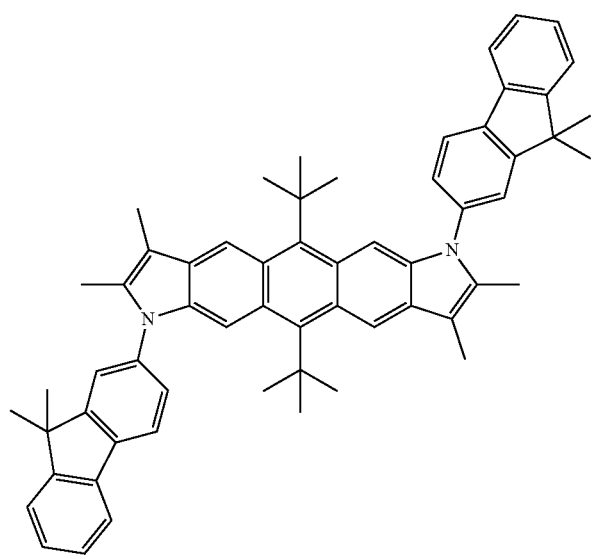
8
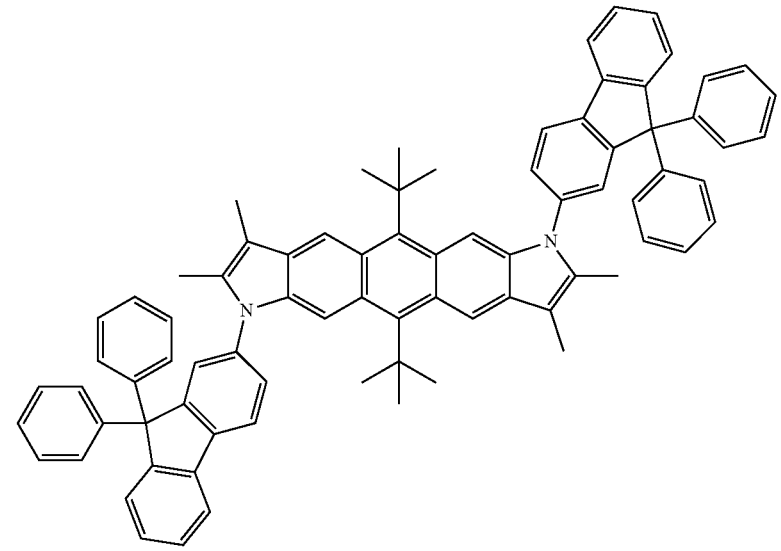
9

-continued
10
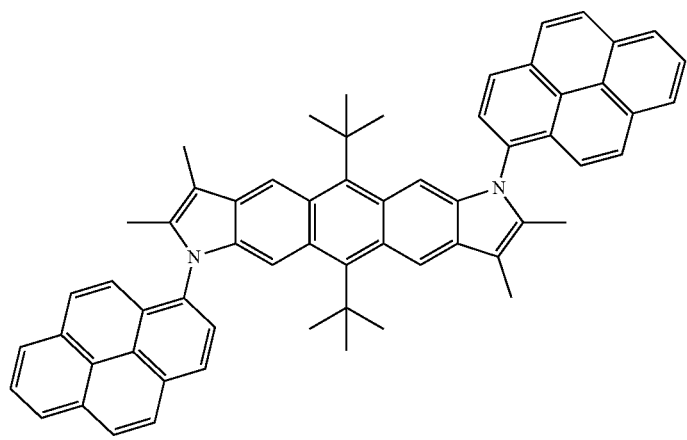
11
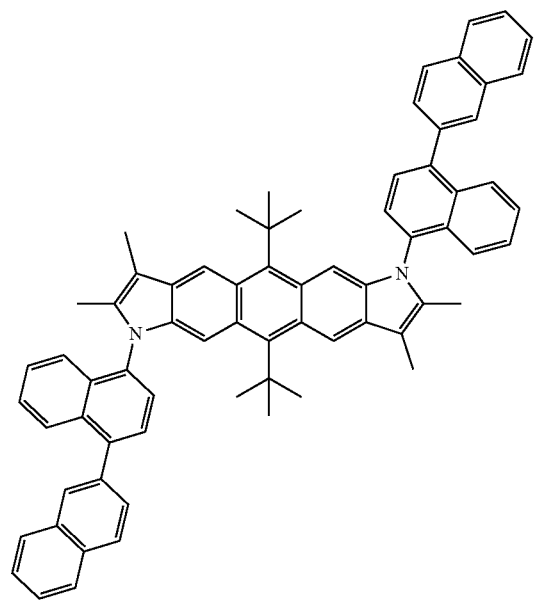
12
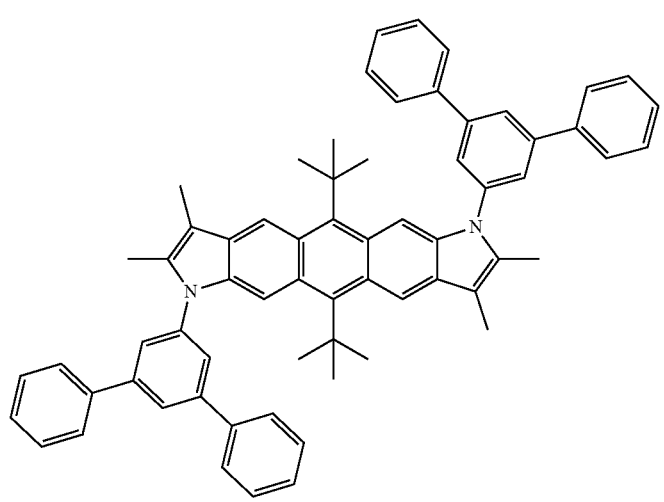

-continued
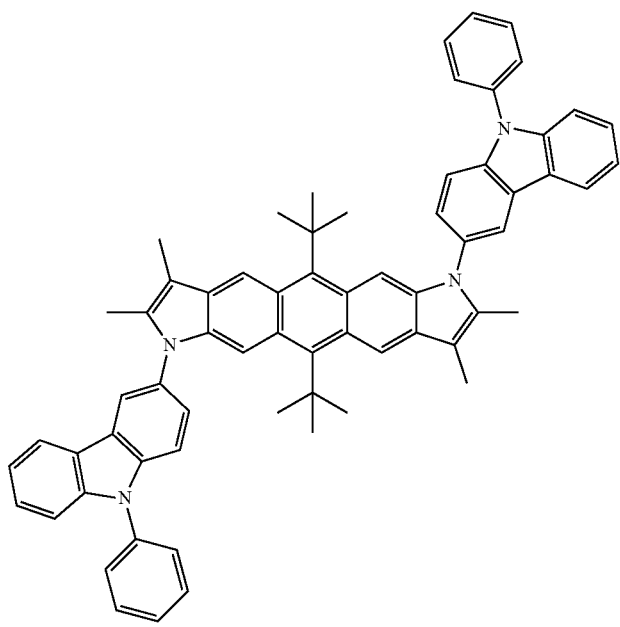
13
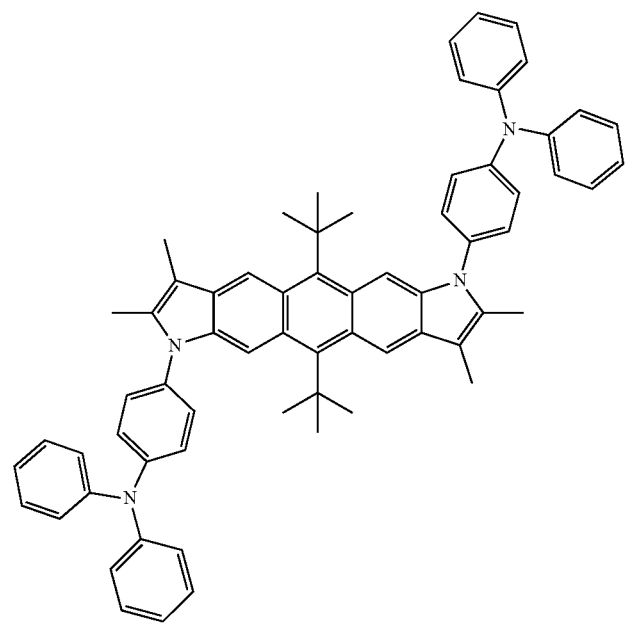
14

-continued
15
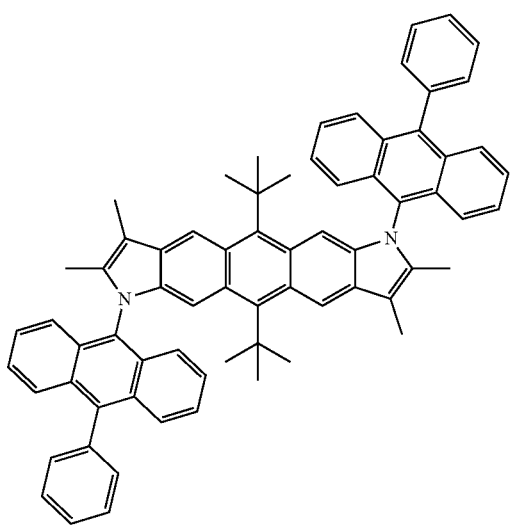
16
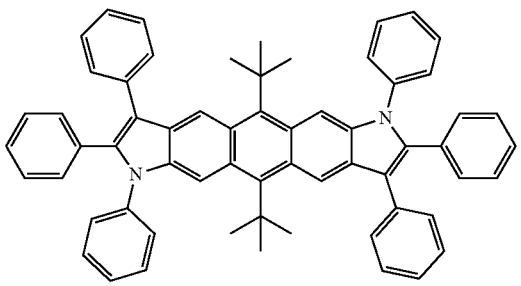
17
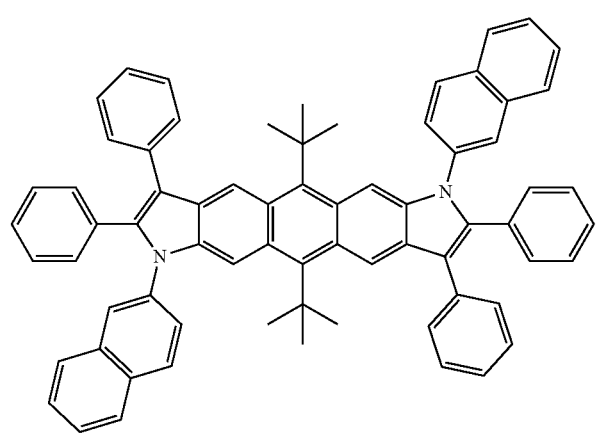
18
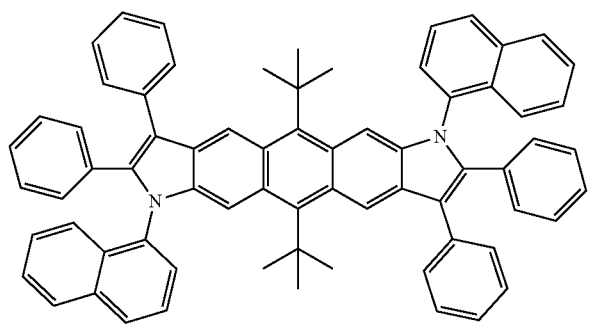

19
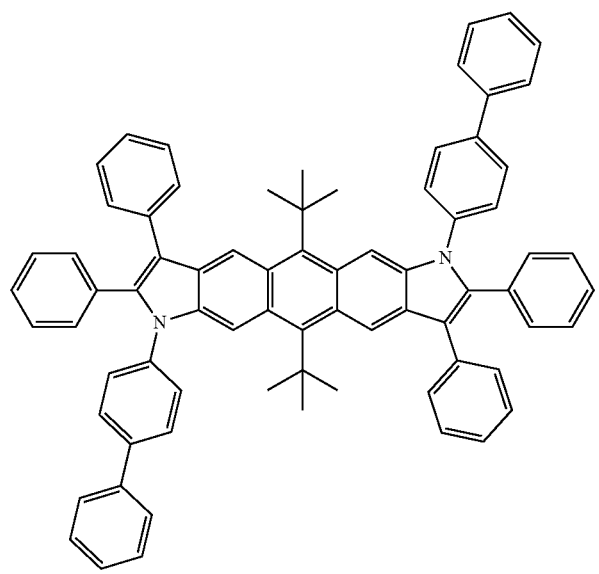
20
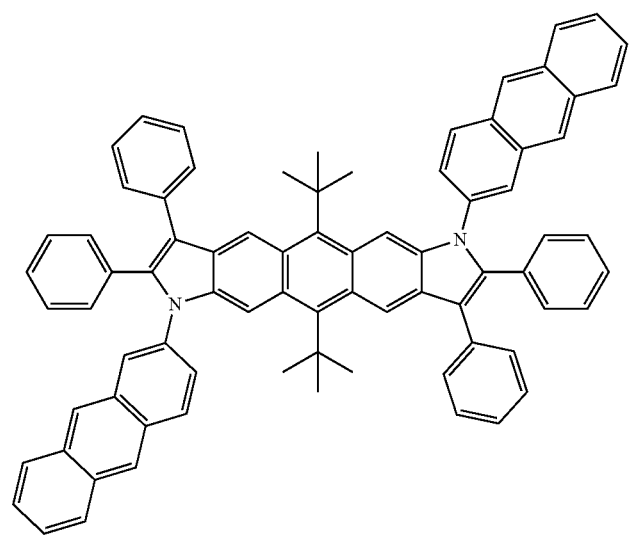
21
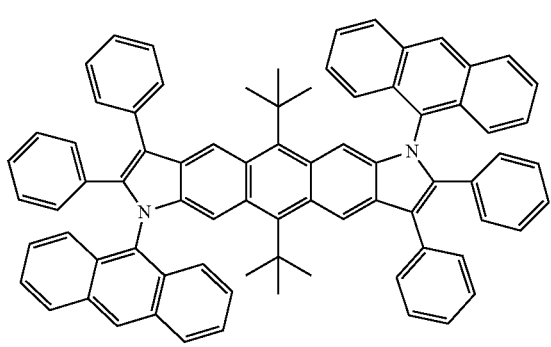
22
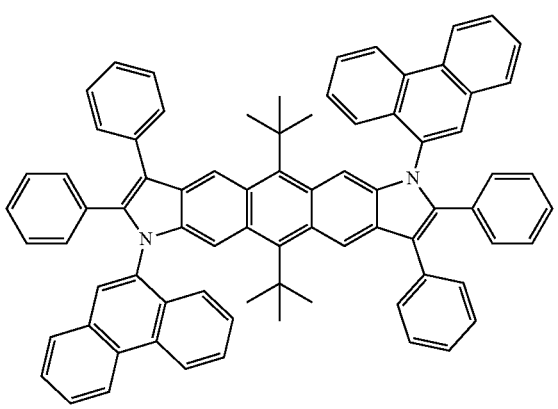

23
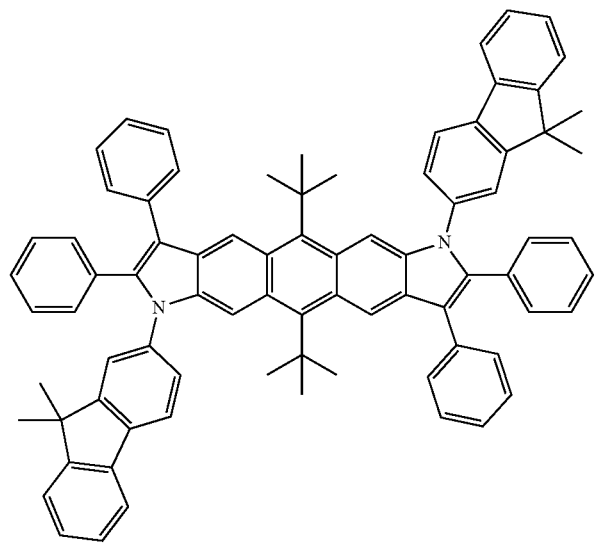
24
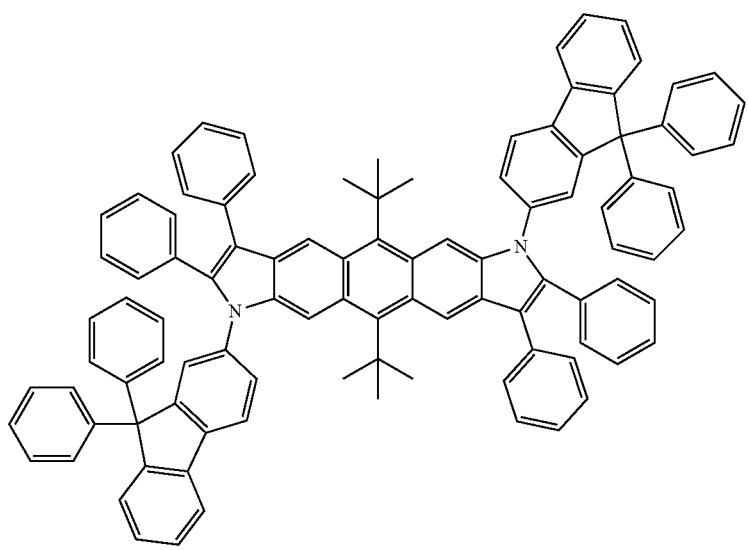
25
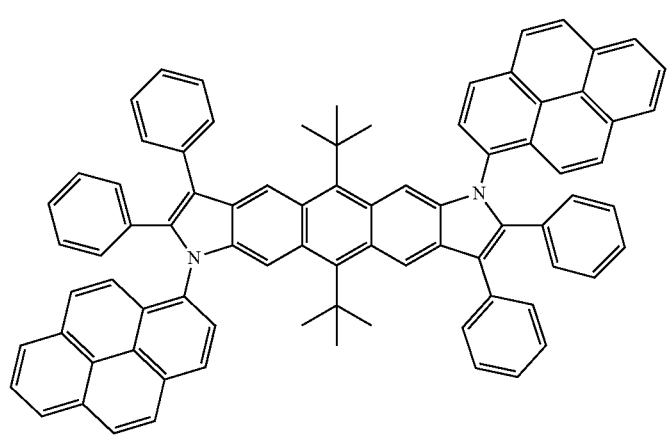

-continued
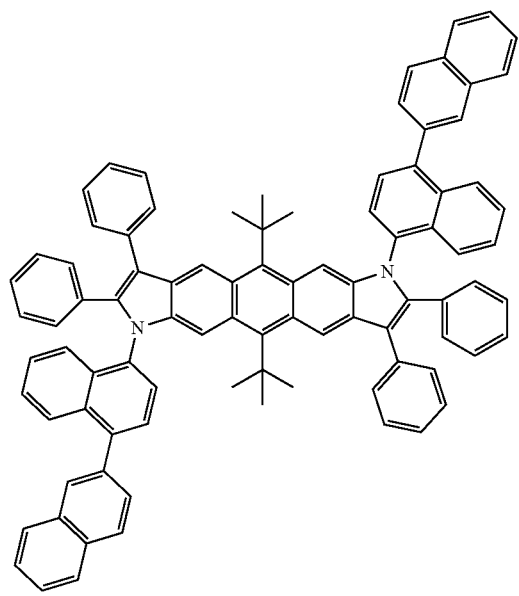
26
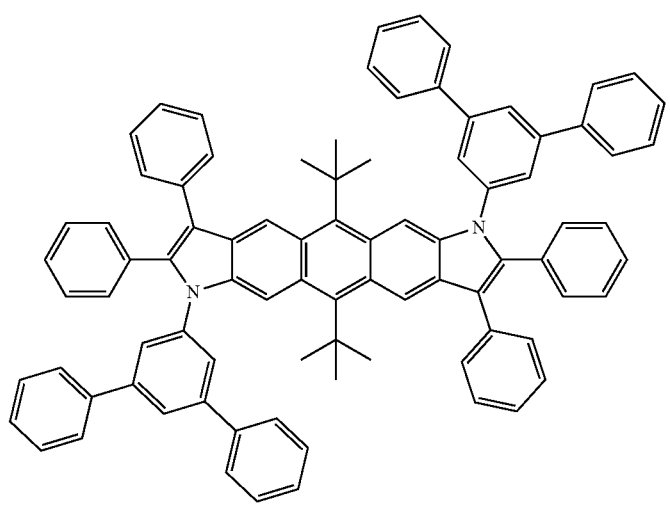
27

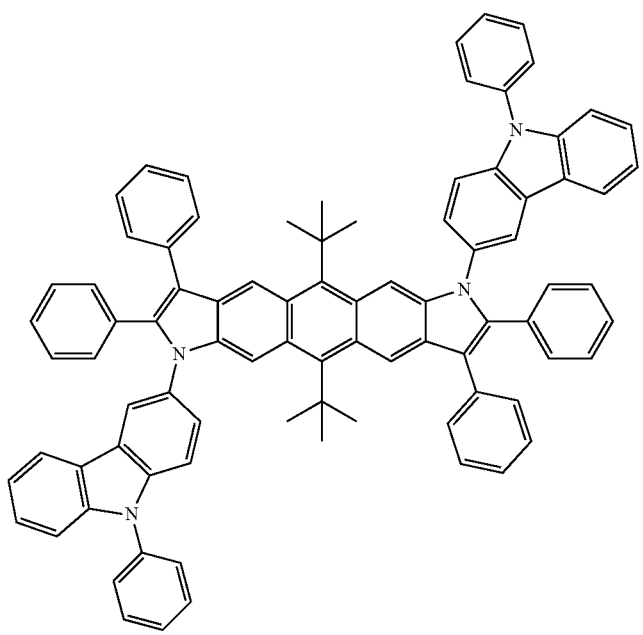
28
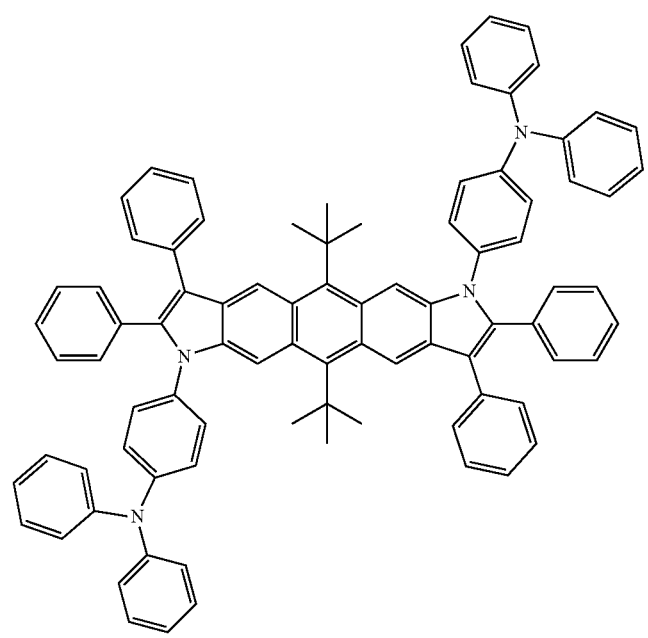
29

-continued
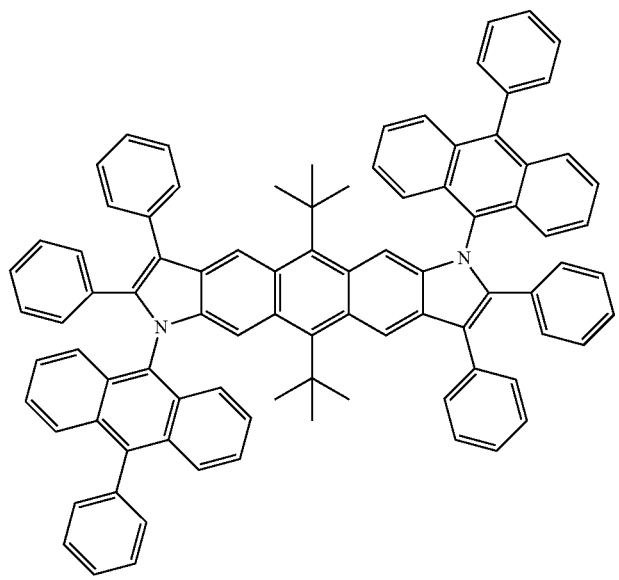
30
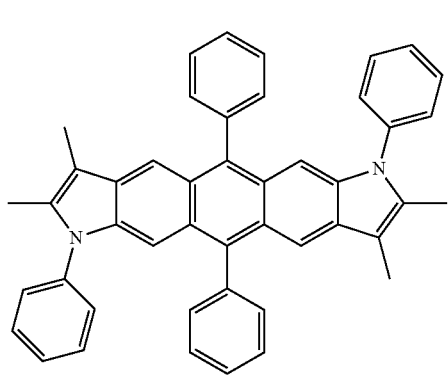
31
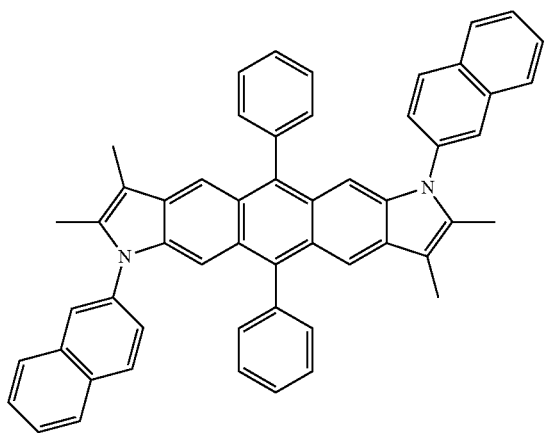
32

33
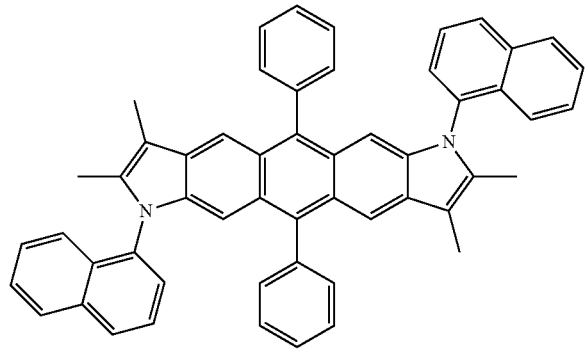
34
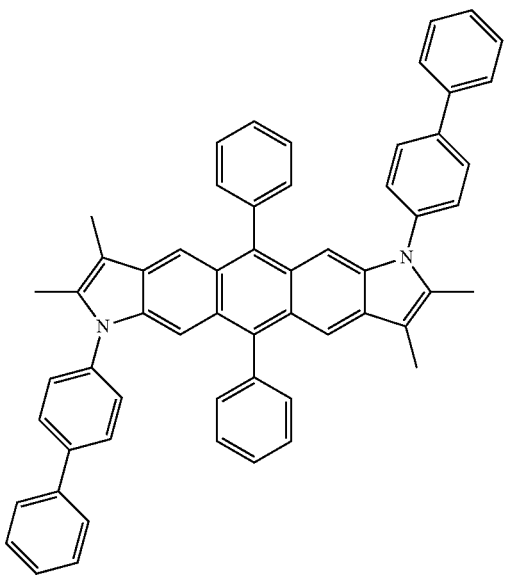
35
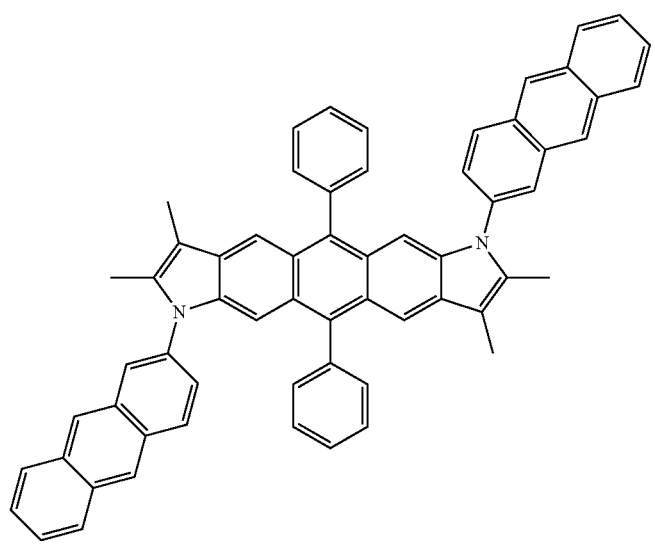
36
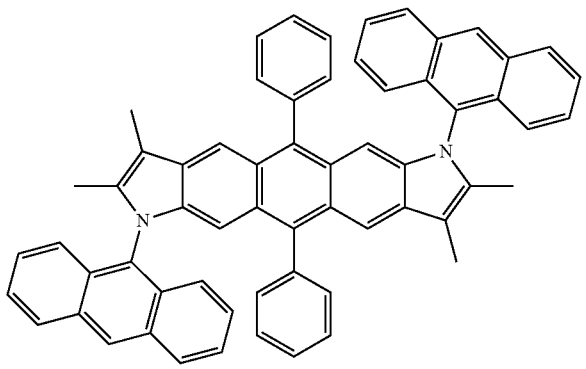

-continued
37
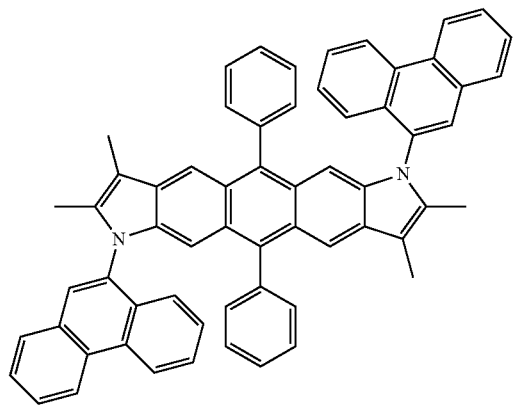
38
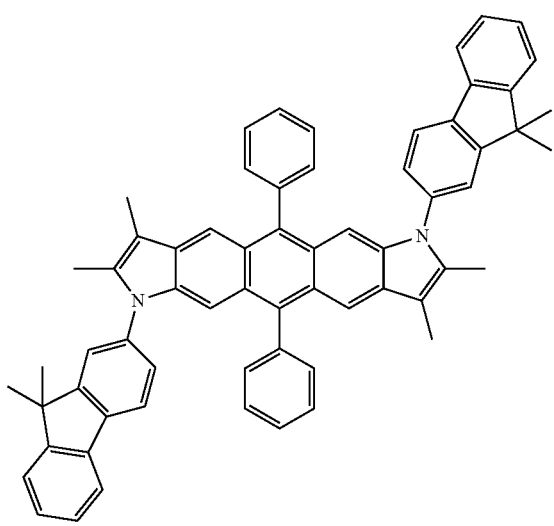
39
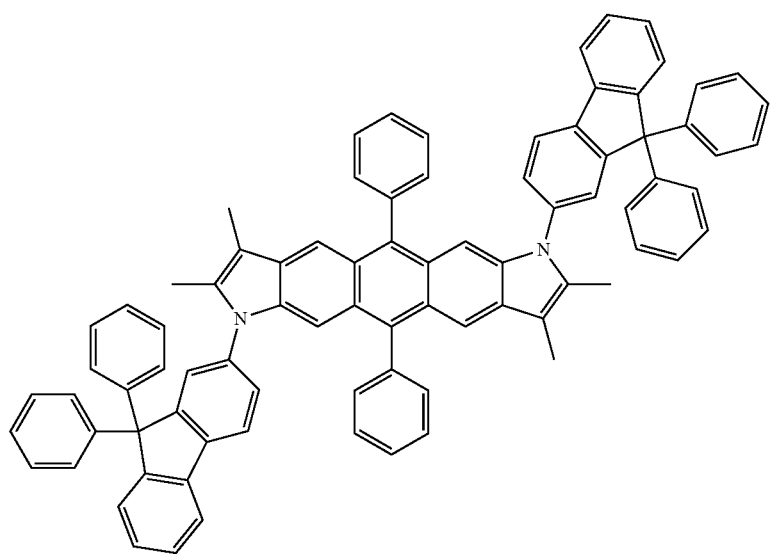
40
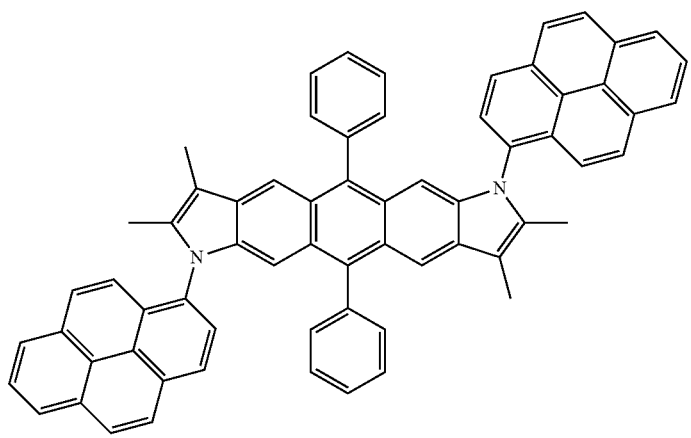

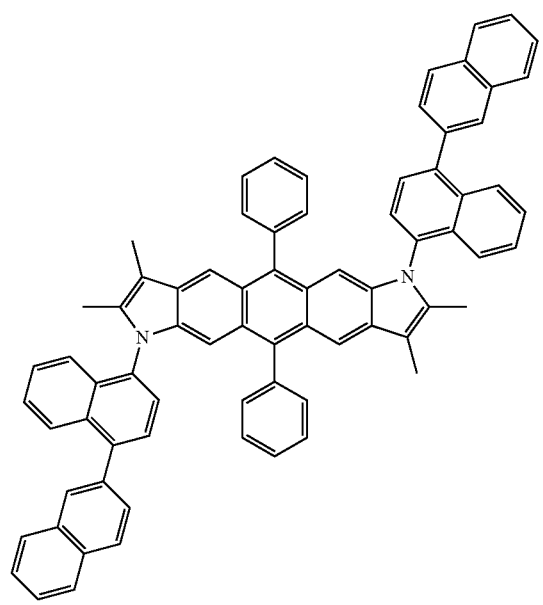
41
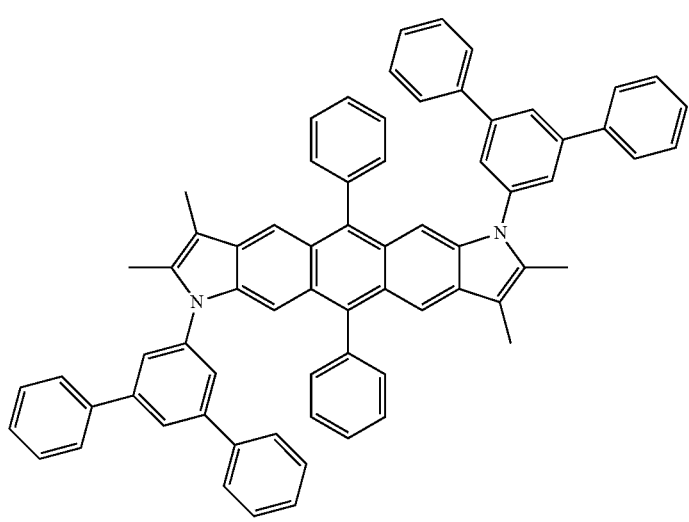
42

-continued
43
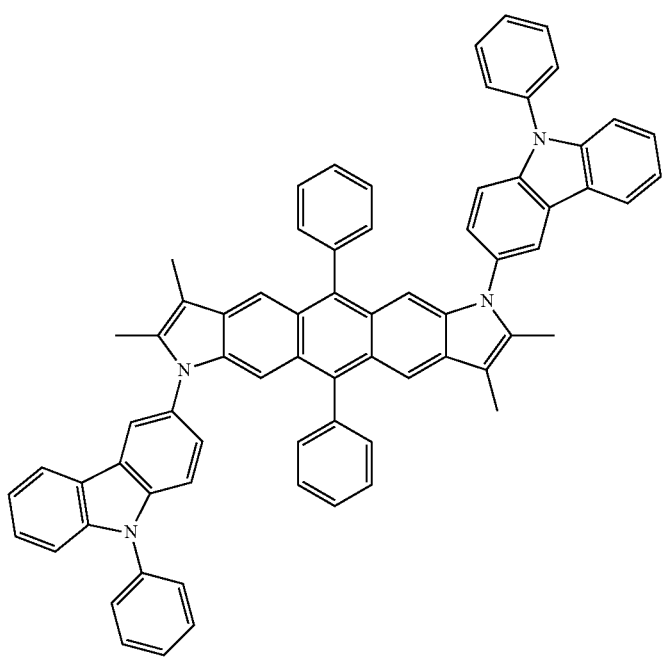
44
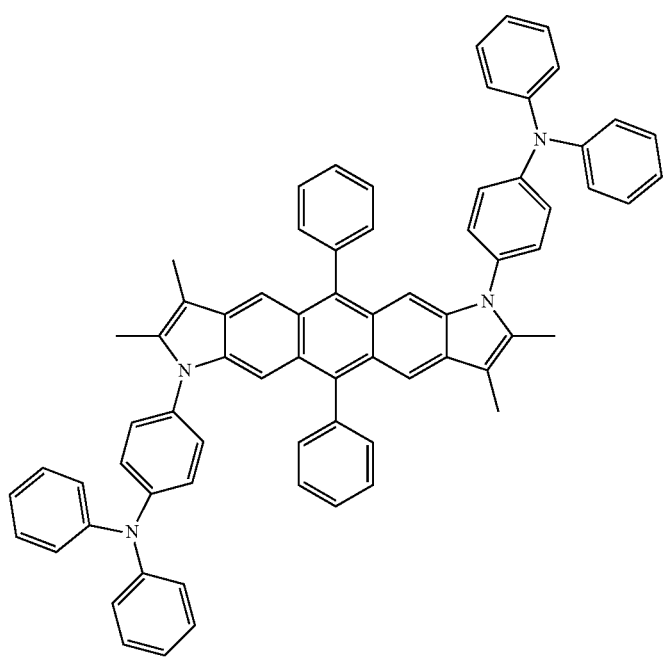

45
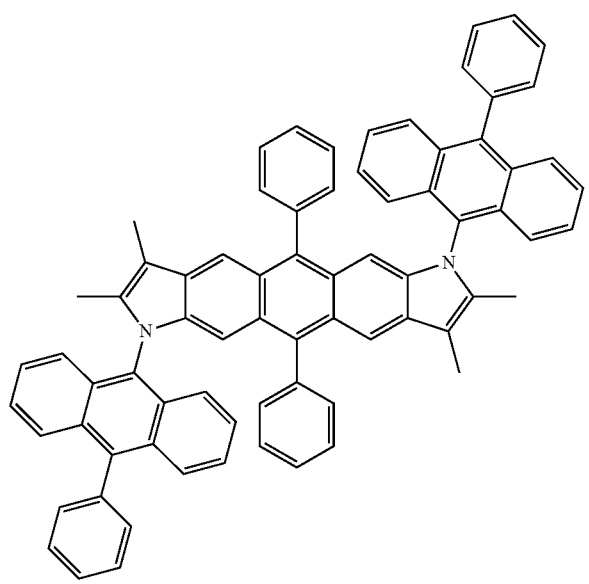
46
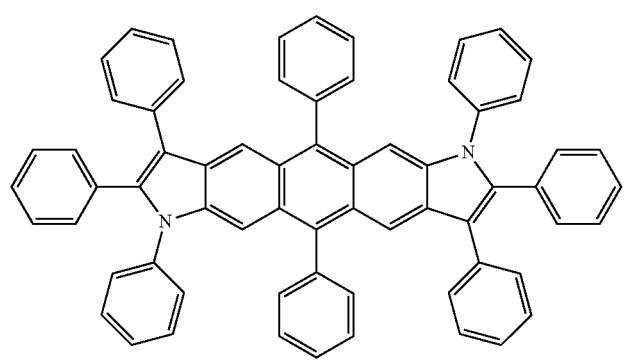
47
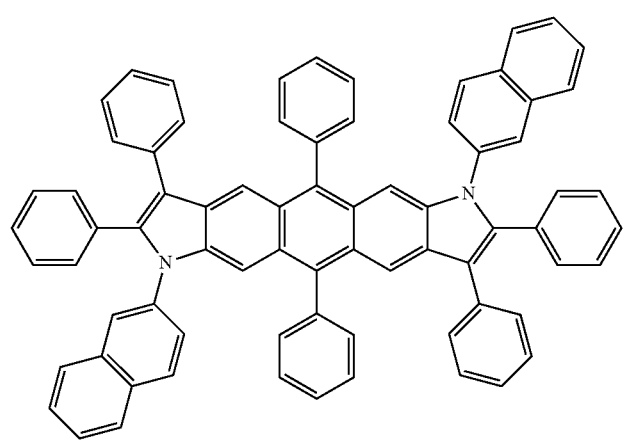

-continued
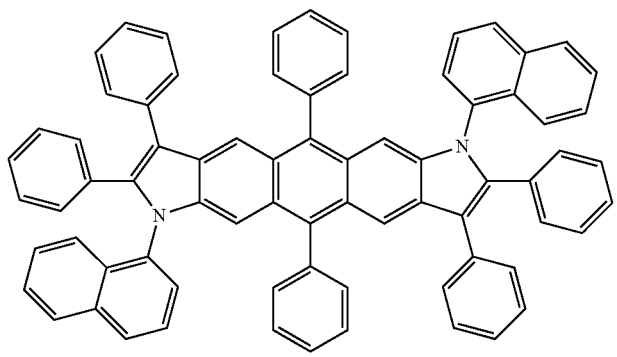
48
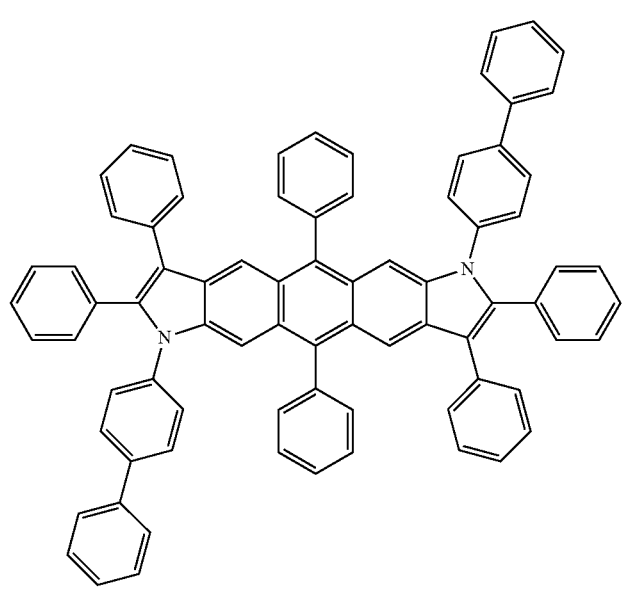
49
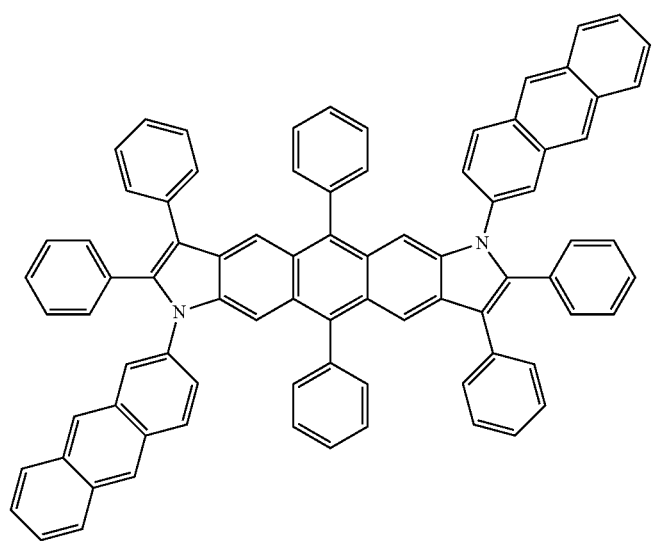
50

51
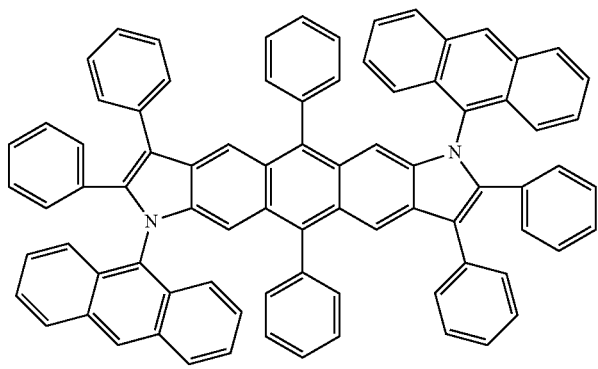
52
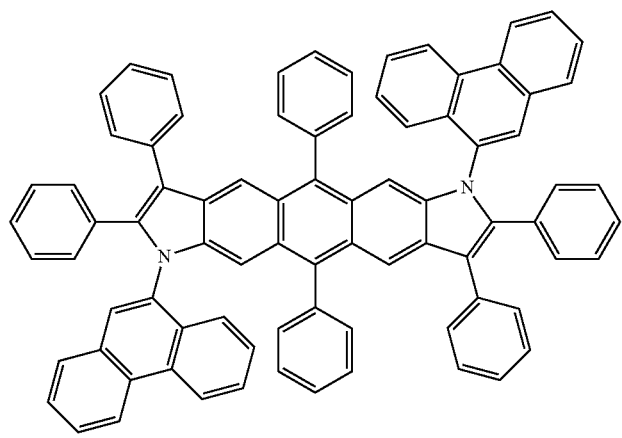
53
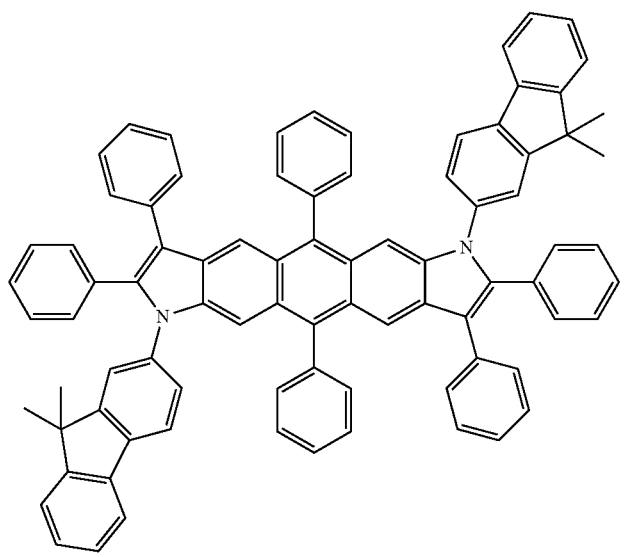

-continued
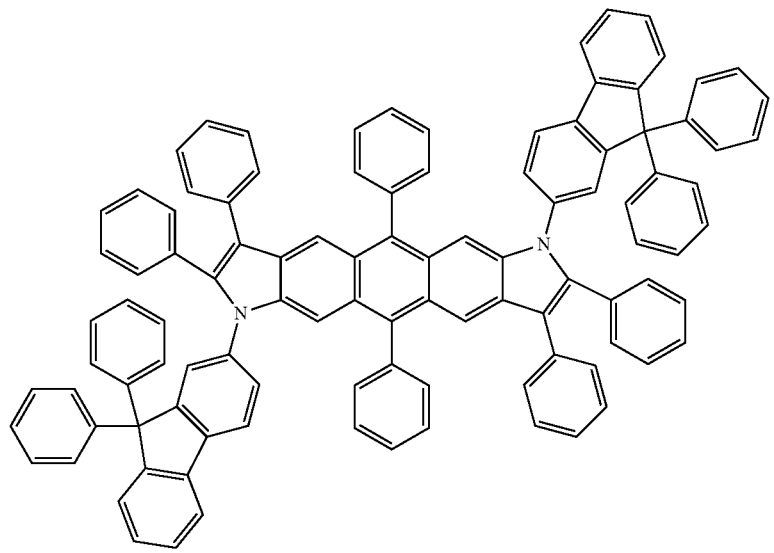
54
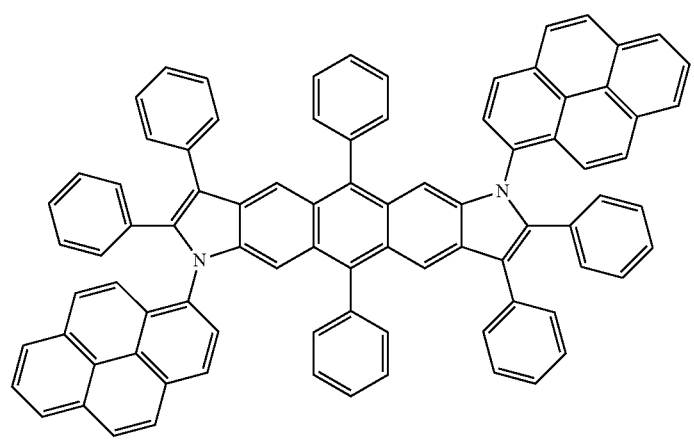
55

56
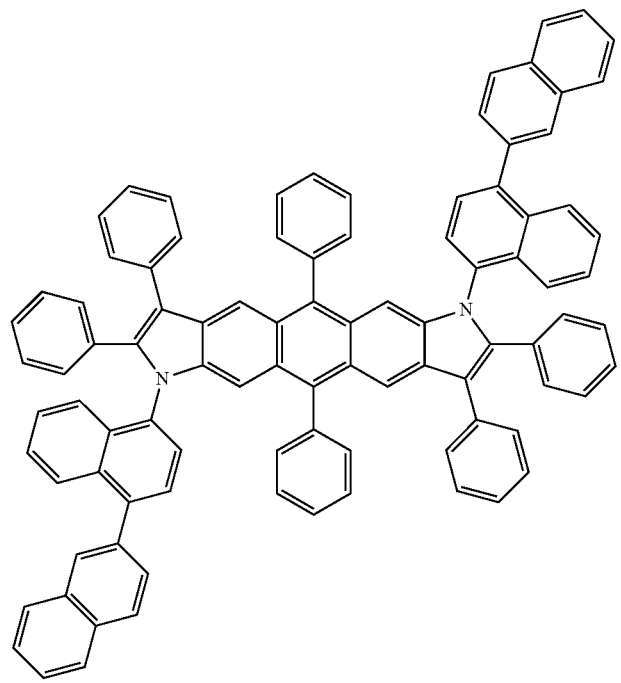
57
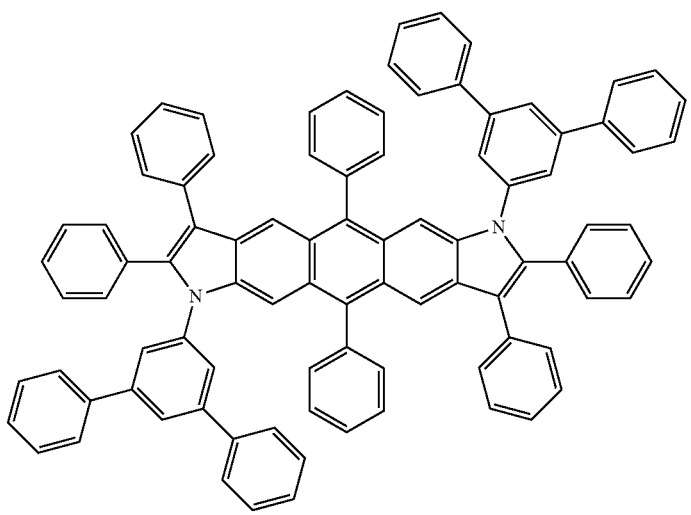

-continued
58
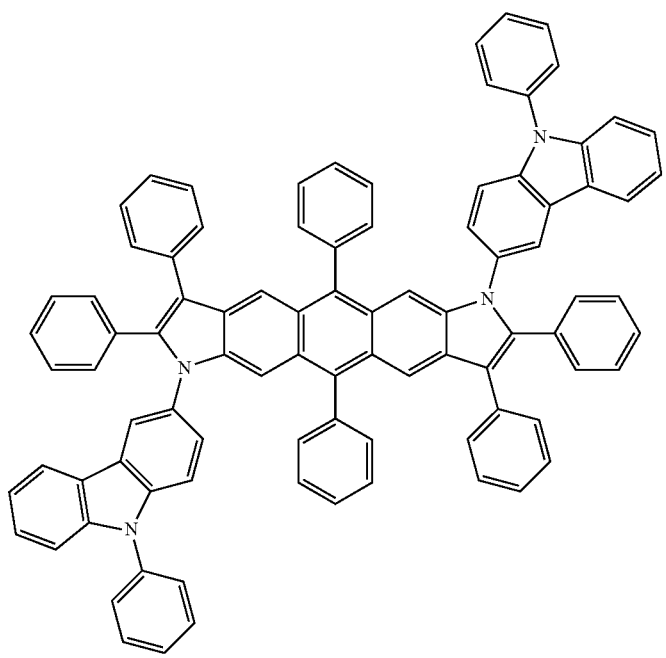
59
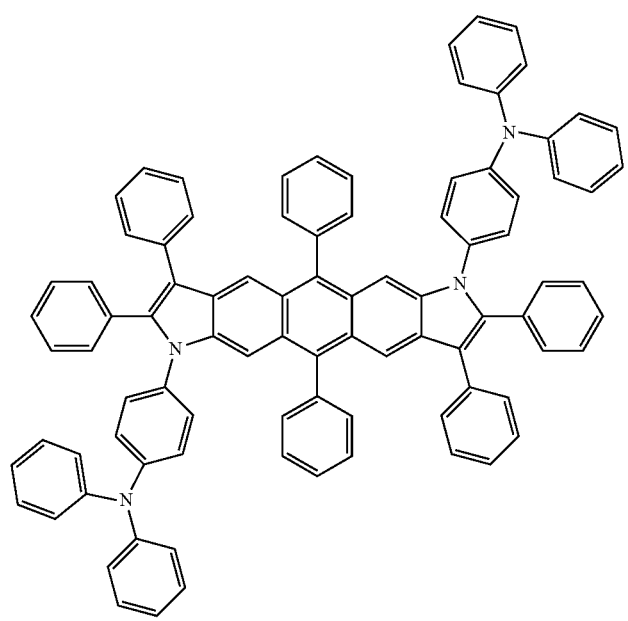

-continued
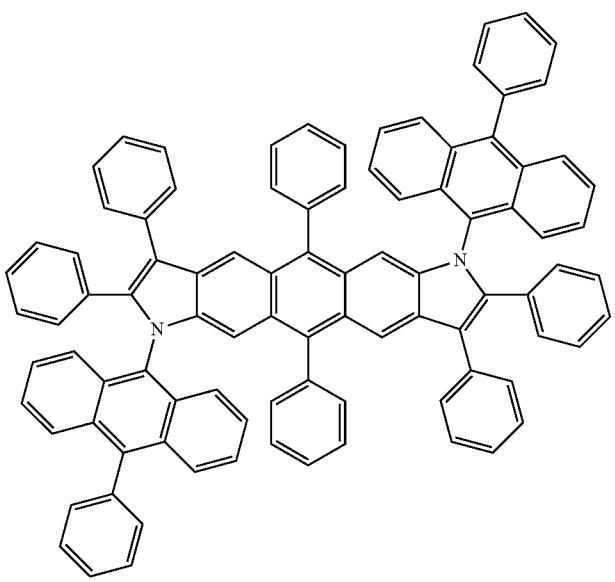
60
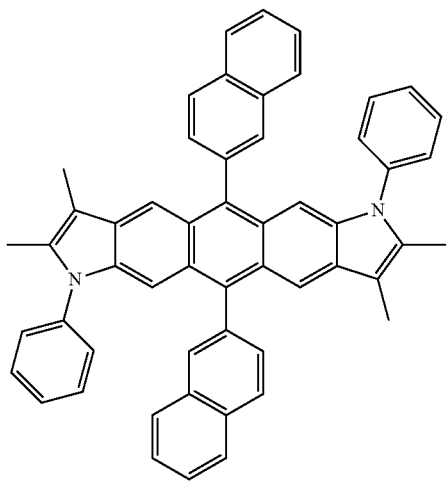
61
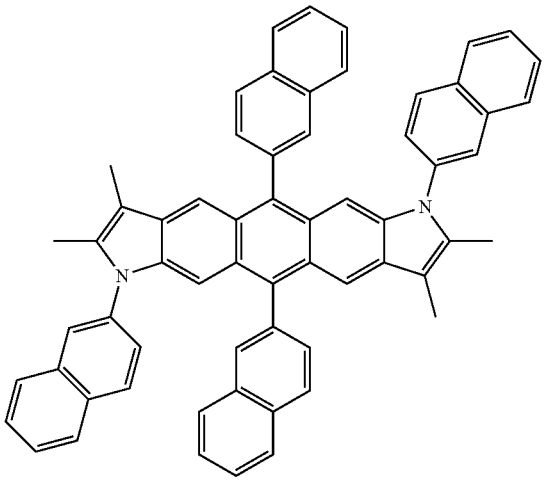
62
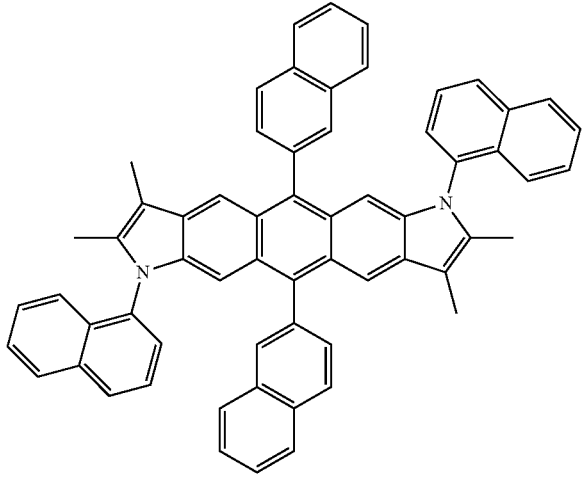
63
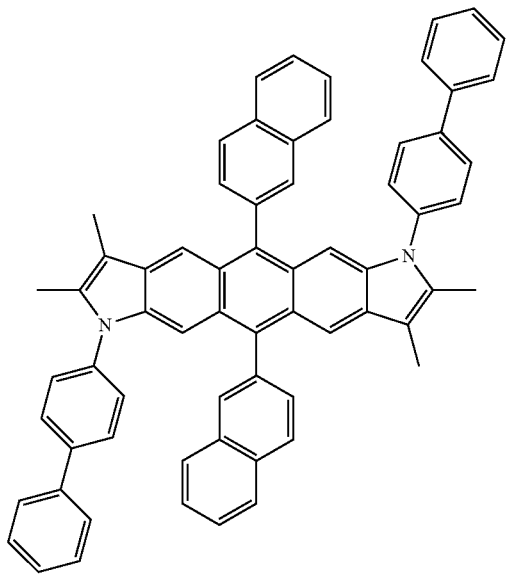
64

-continued
65
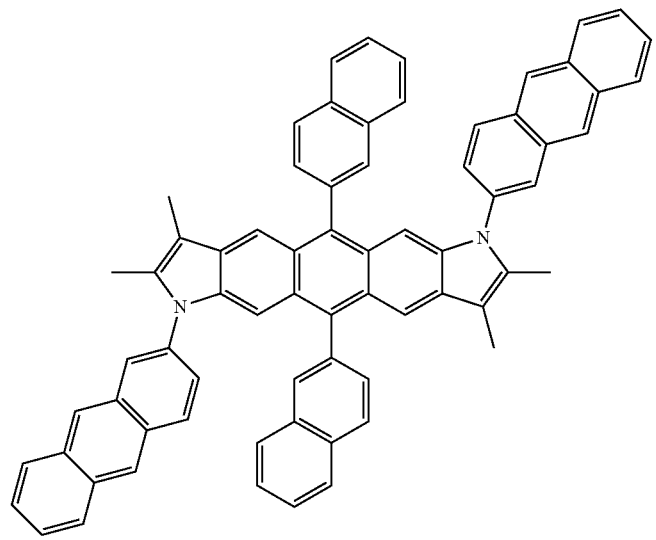
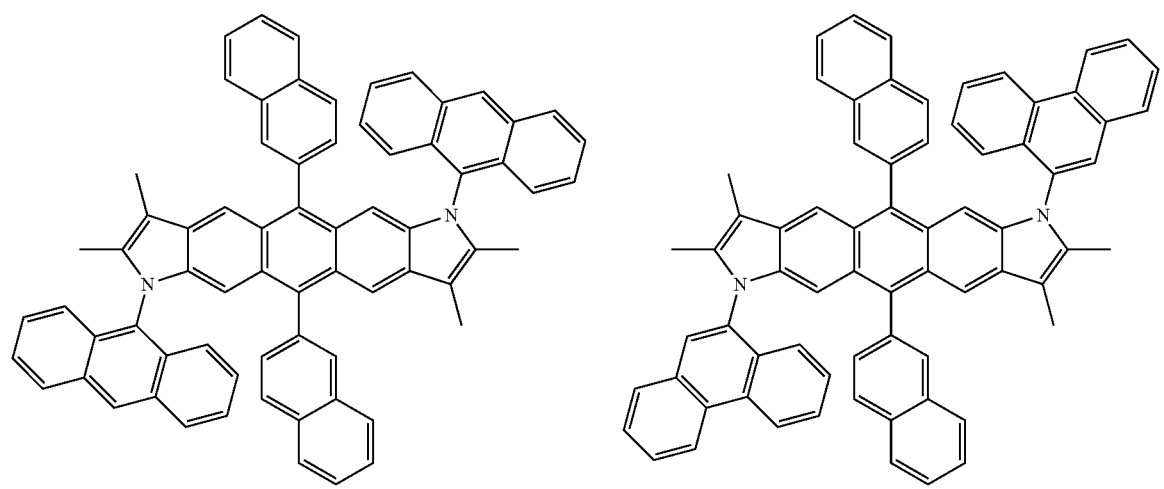

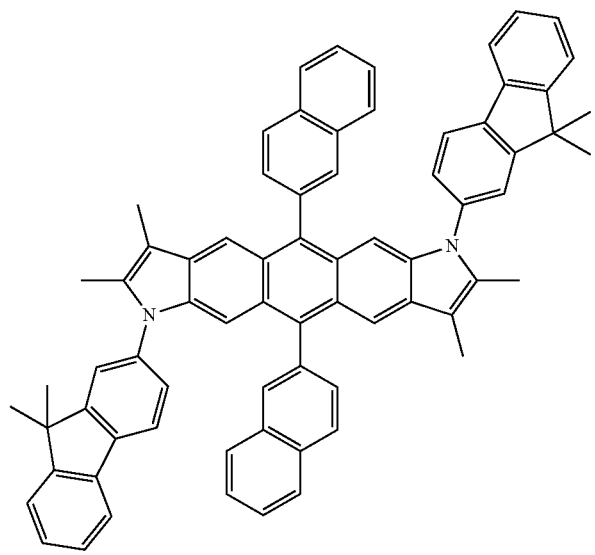
68
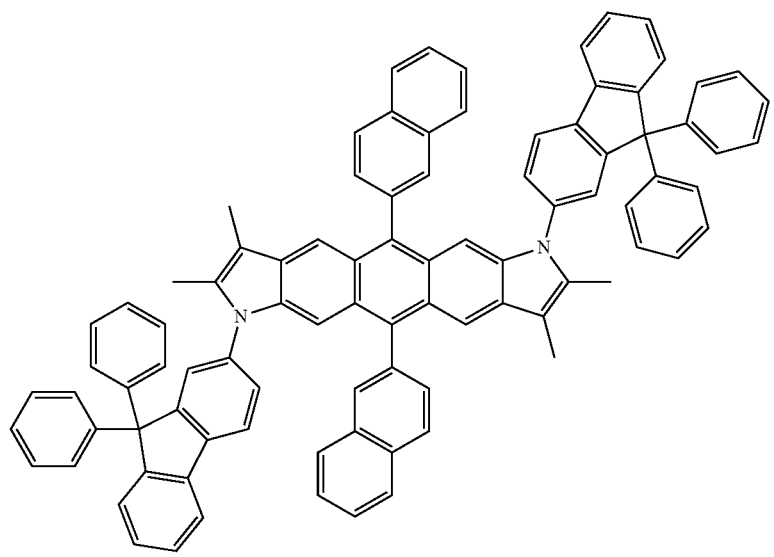
69
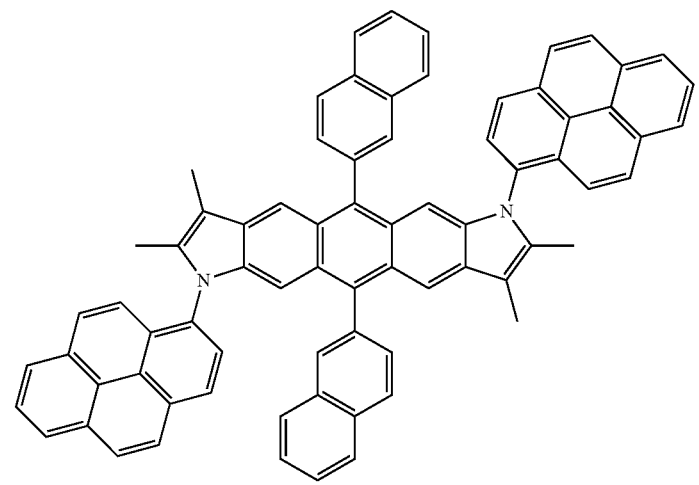
70

-continued
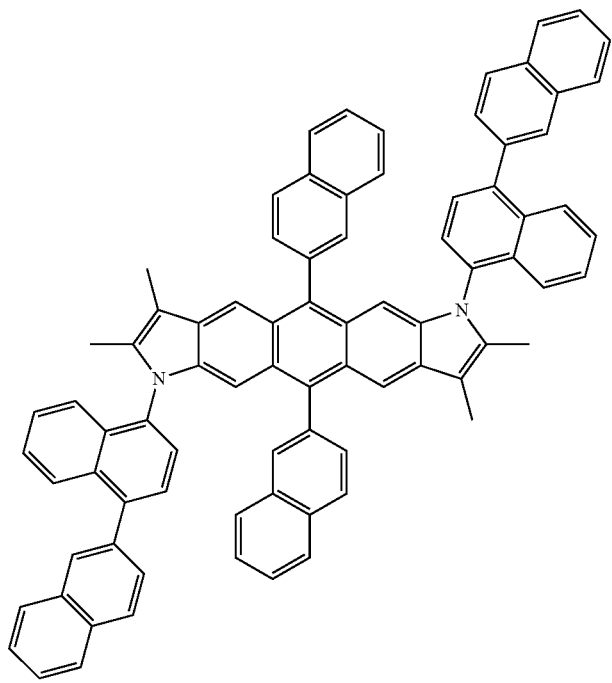
71
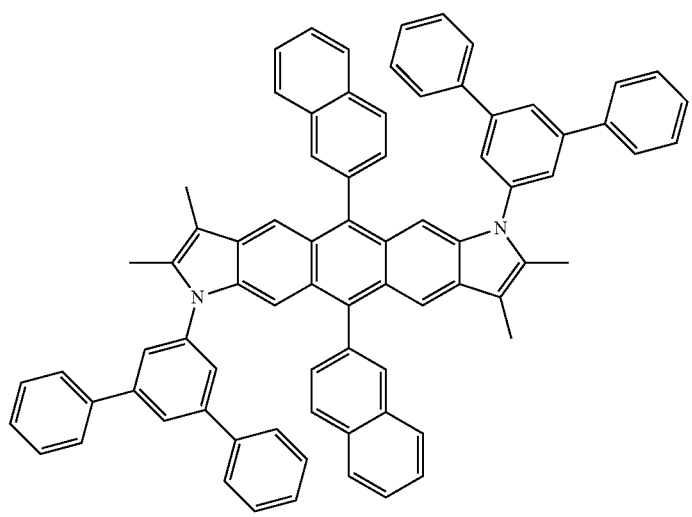
72

-continued
73
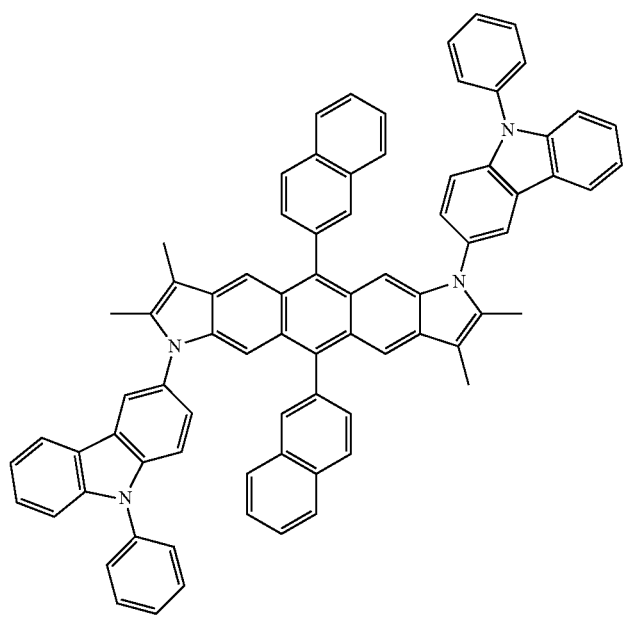
74
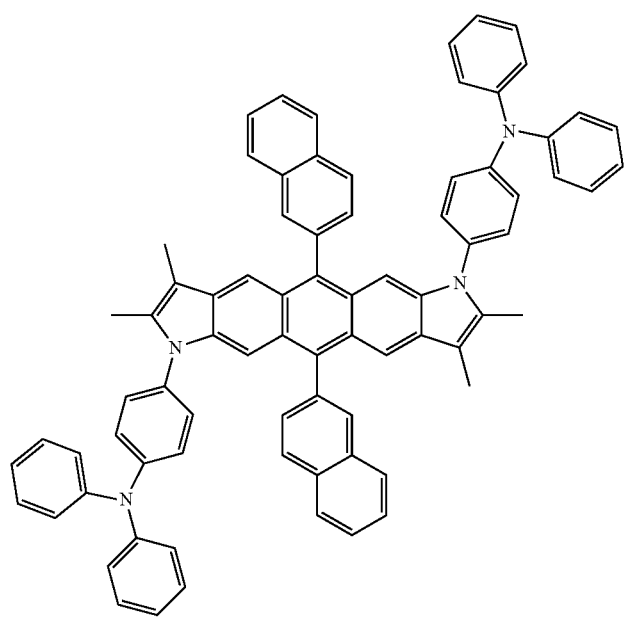

75
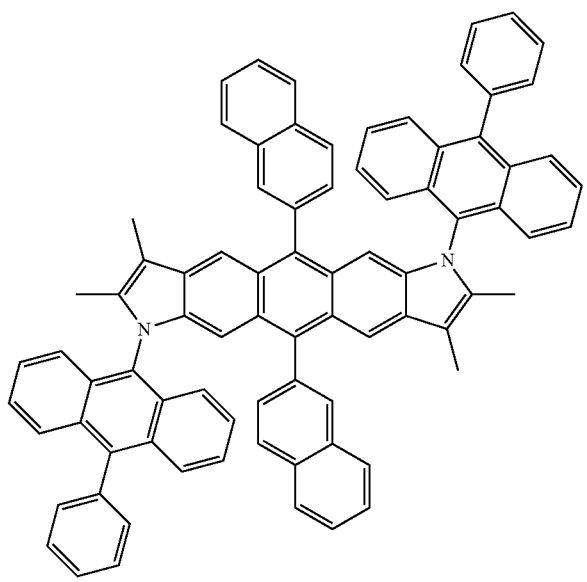
76
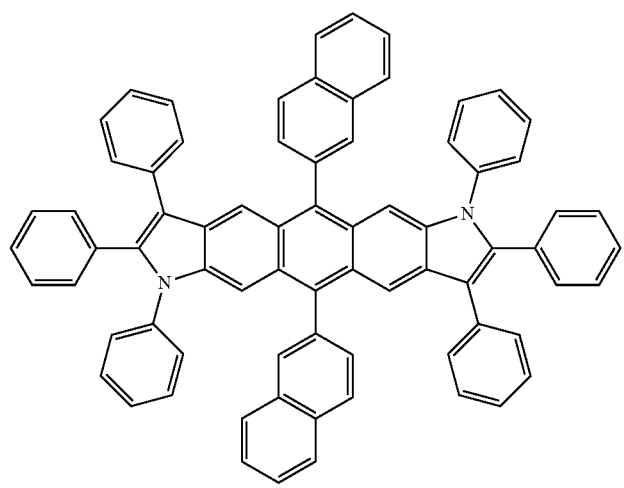
77
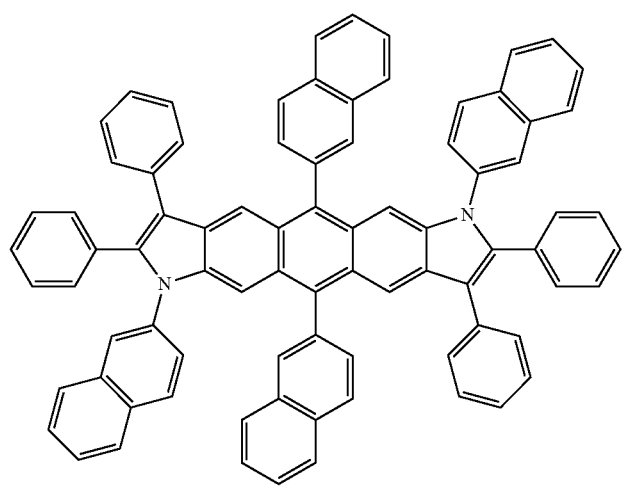

-continued
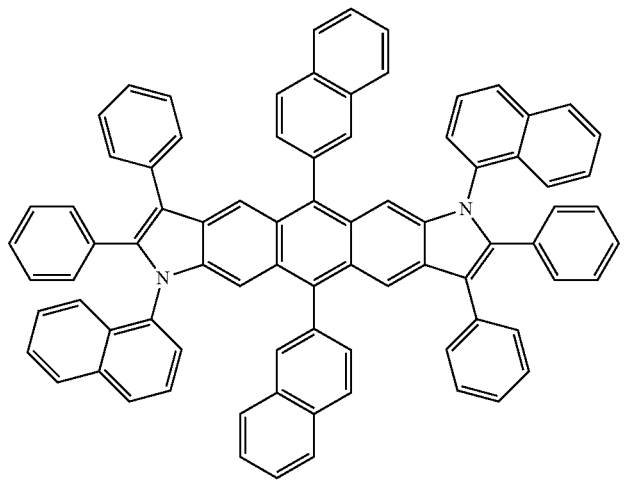
78
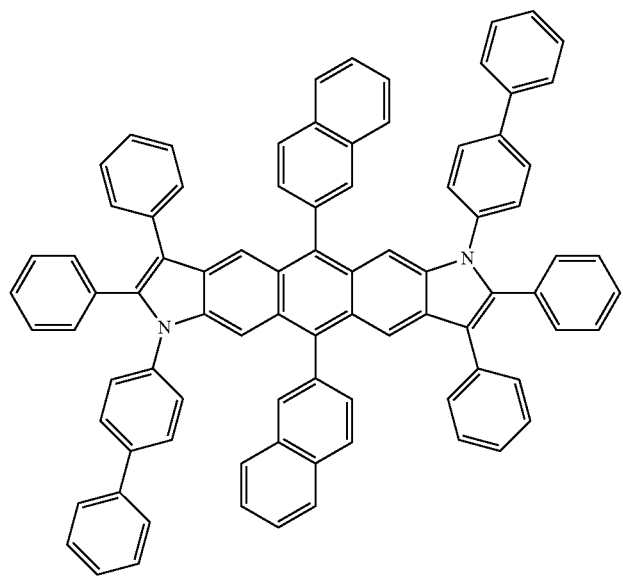
79
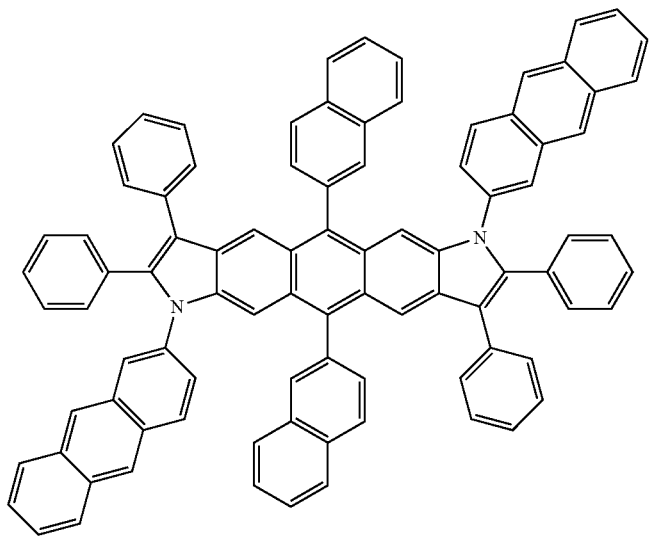
80

81
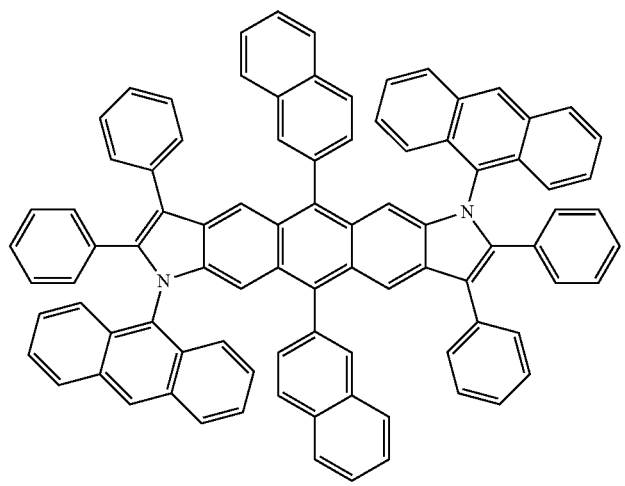
82
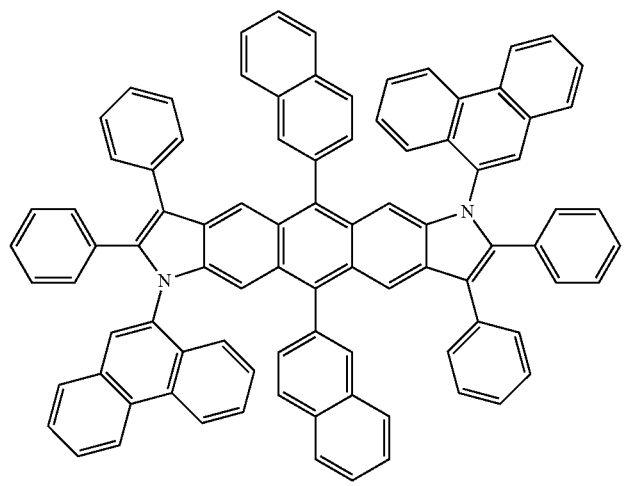
83
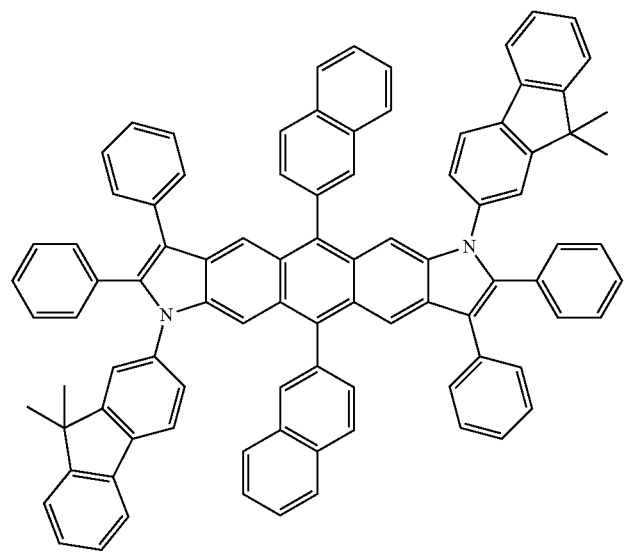

-continued
84
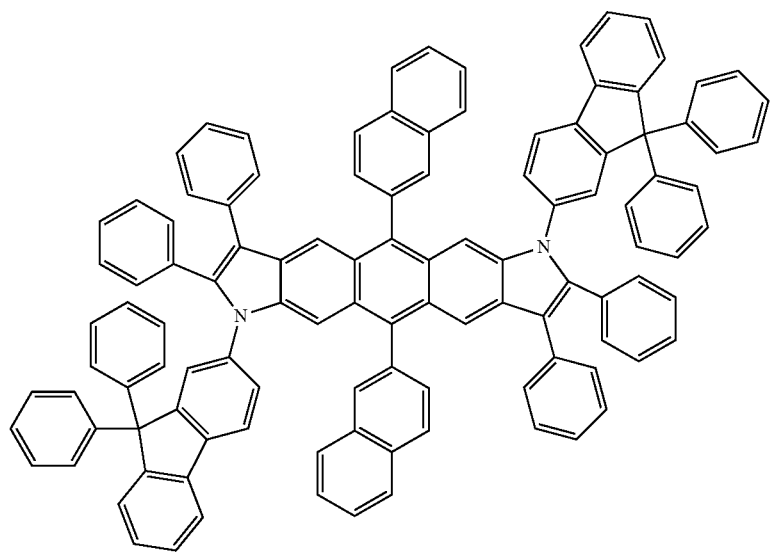
85
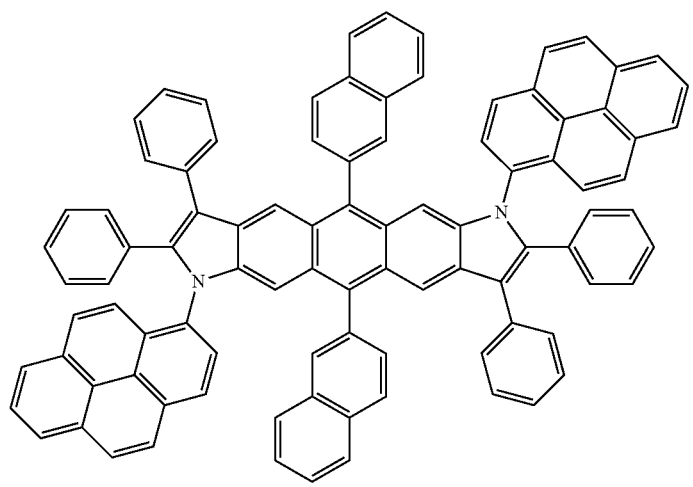

-continued
86
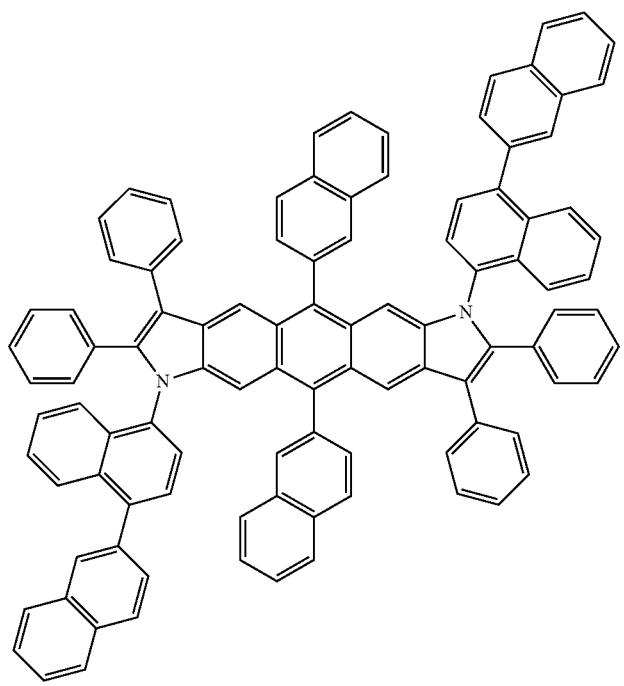
87
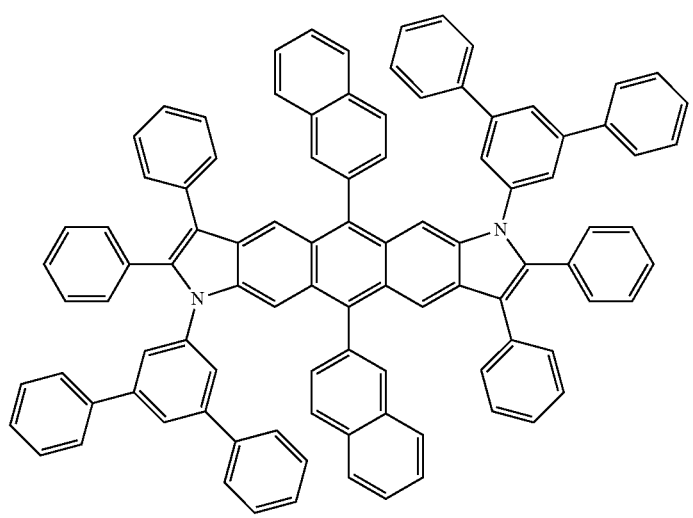

-continued
88
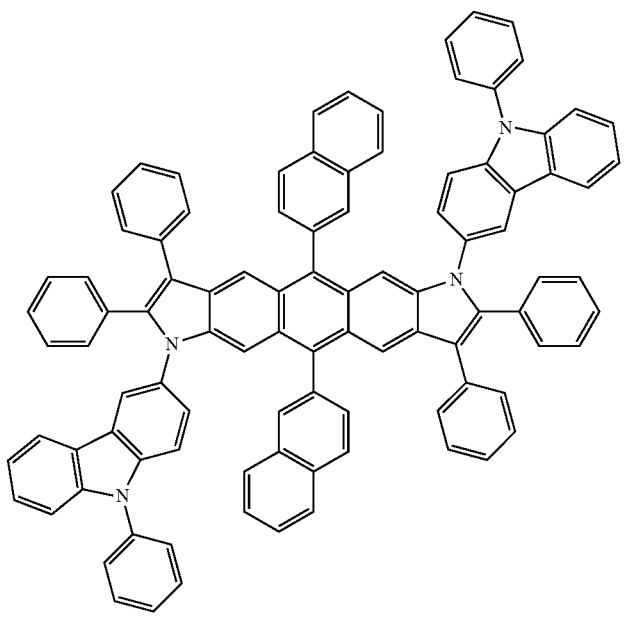
89
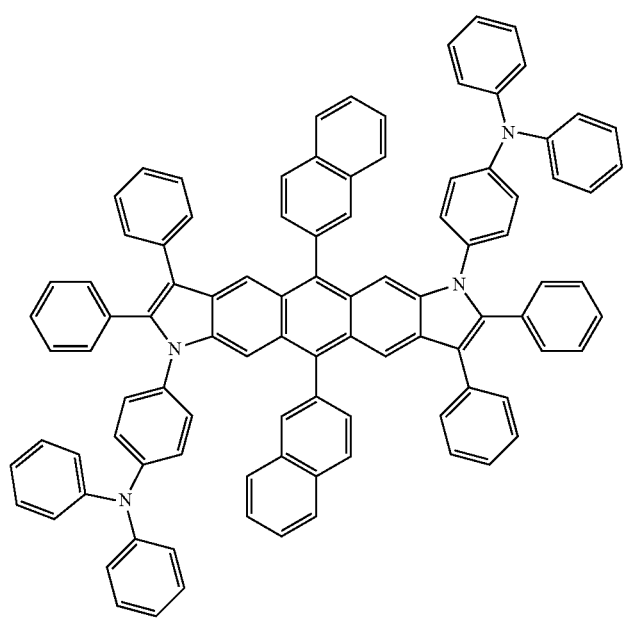

90
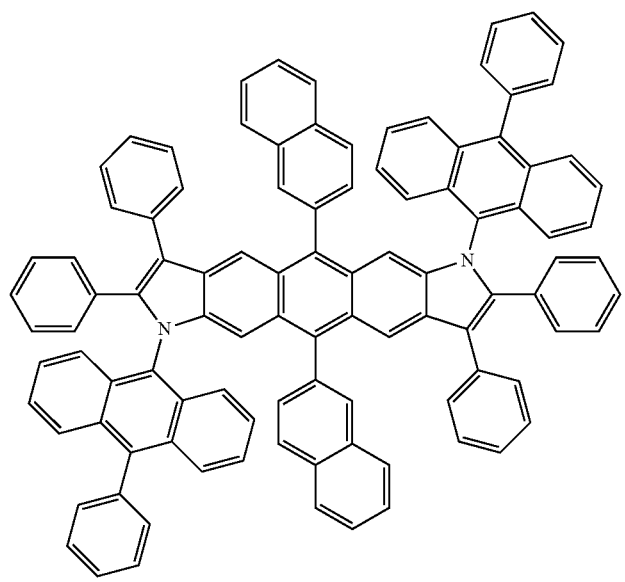
91
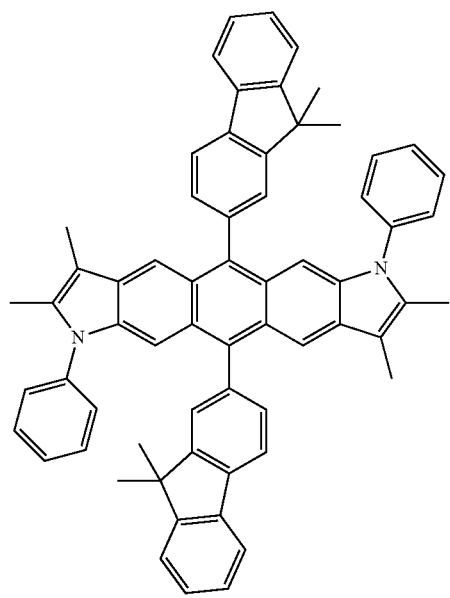
92
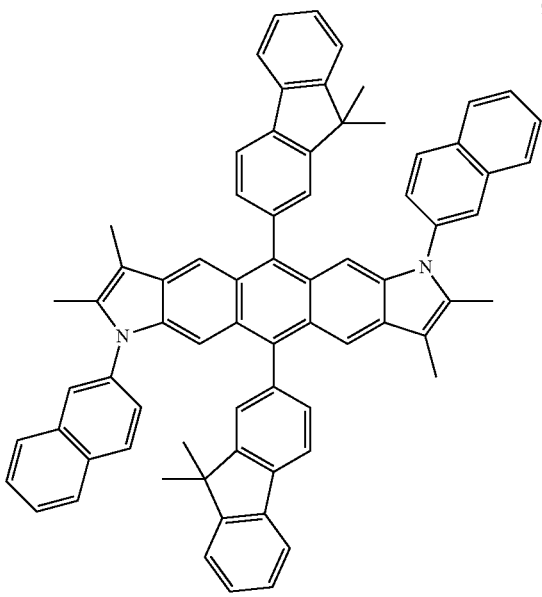

-continued
93
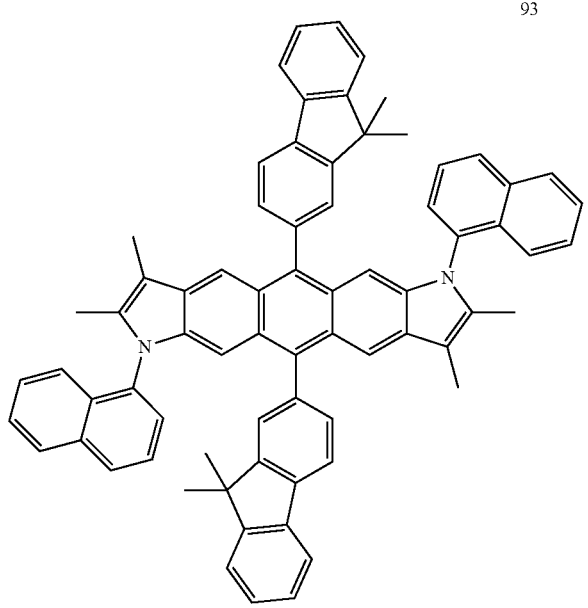
94
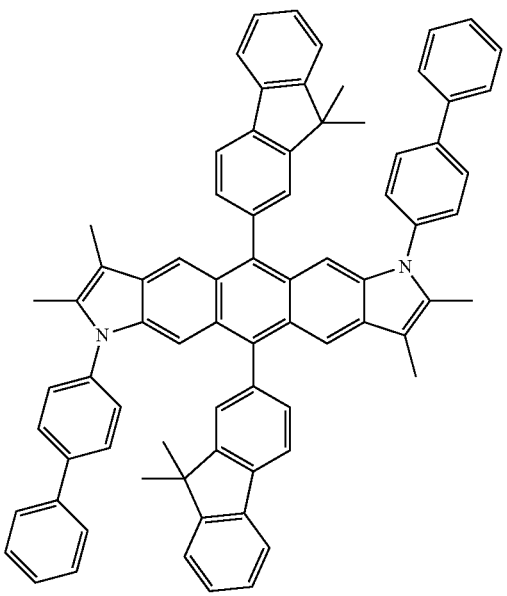
95
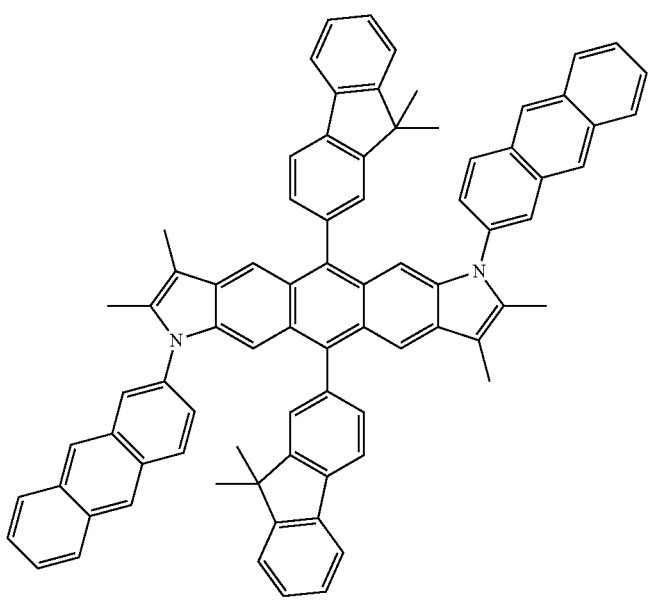

96
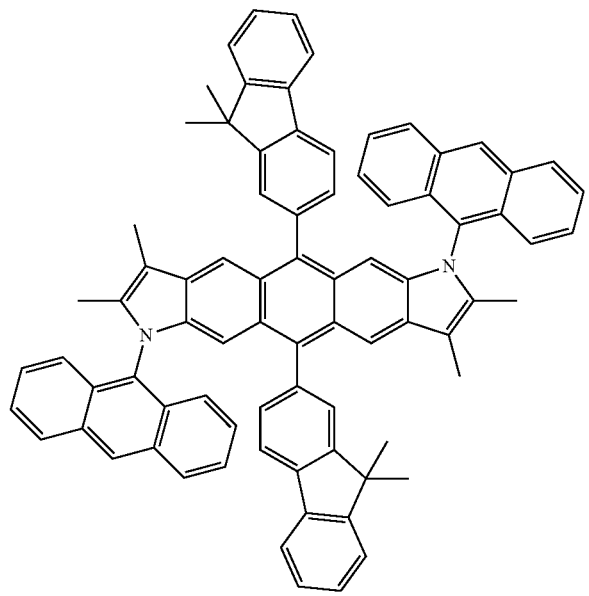
97
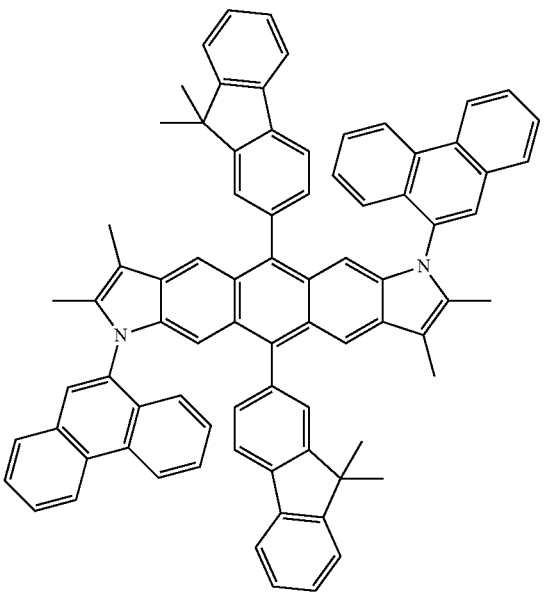
98
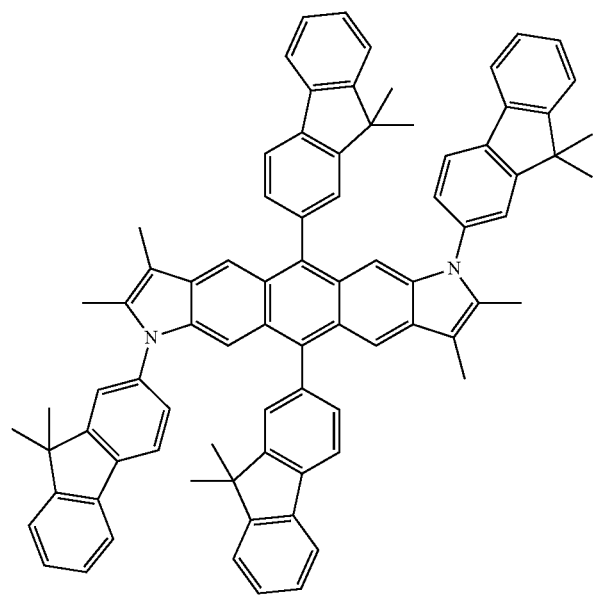

-continued
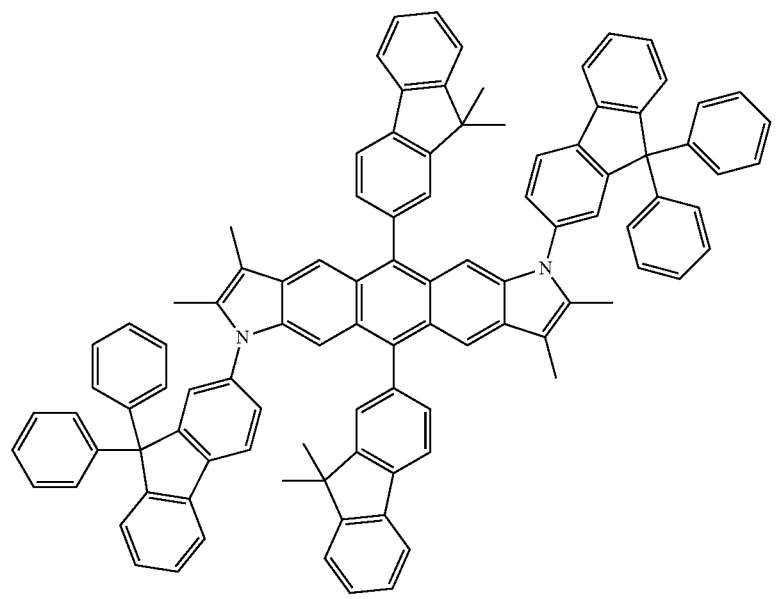
99
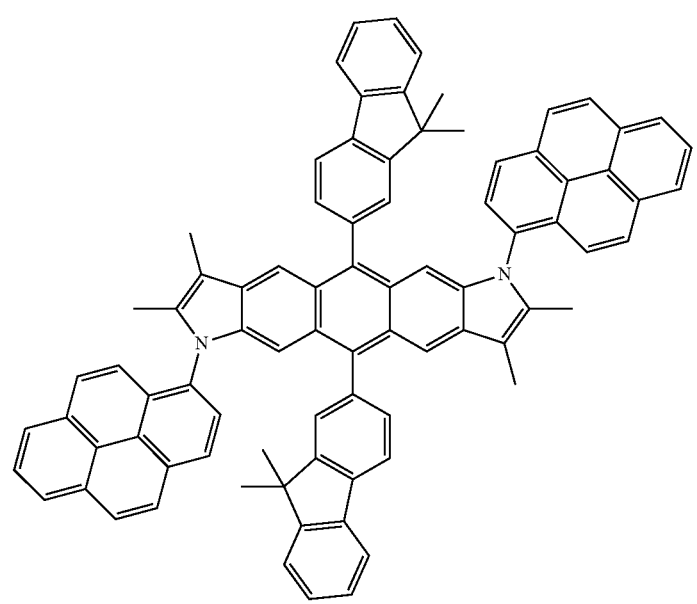
100

-continued
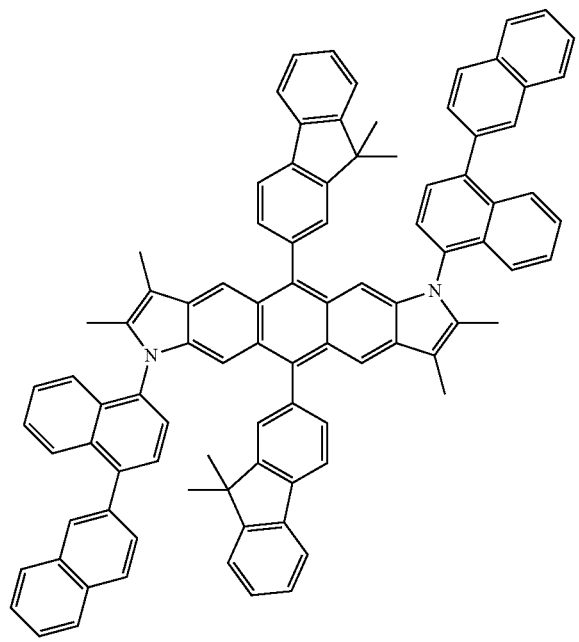
101
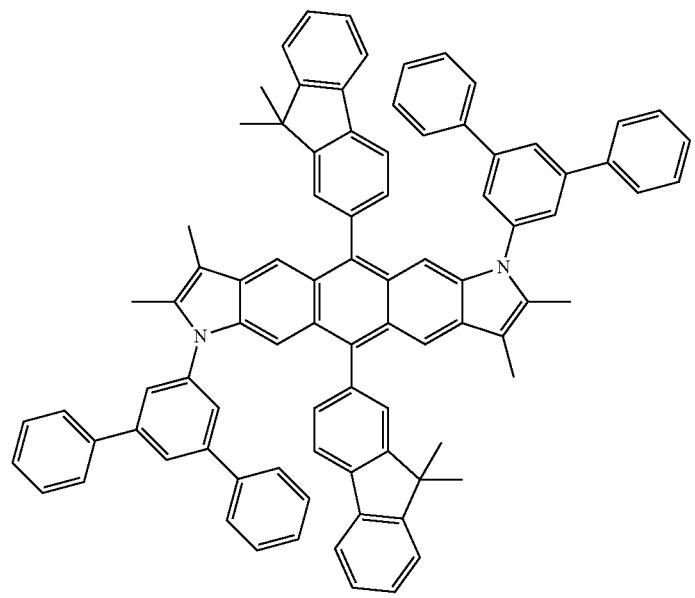
102

-continued
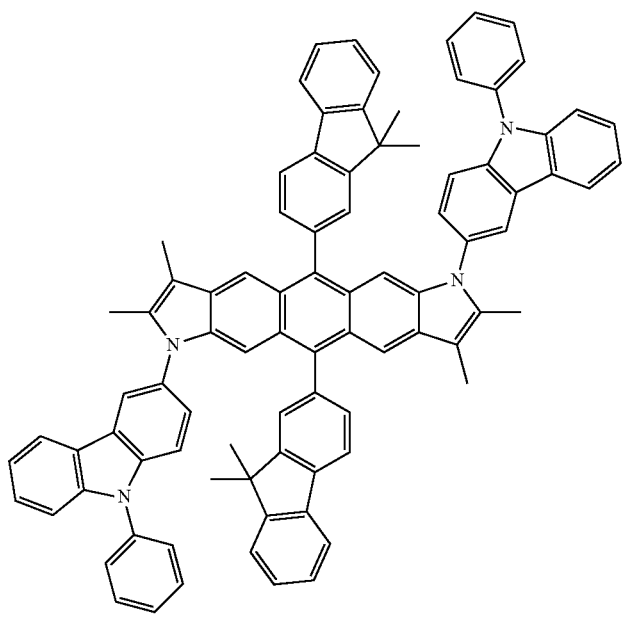
103
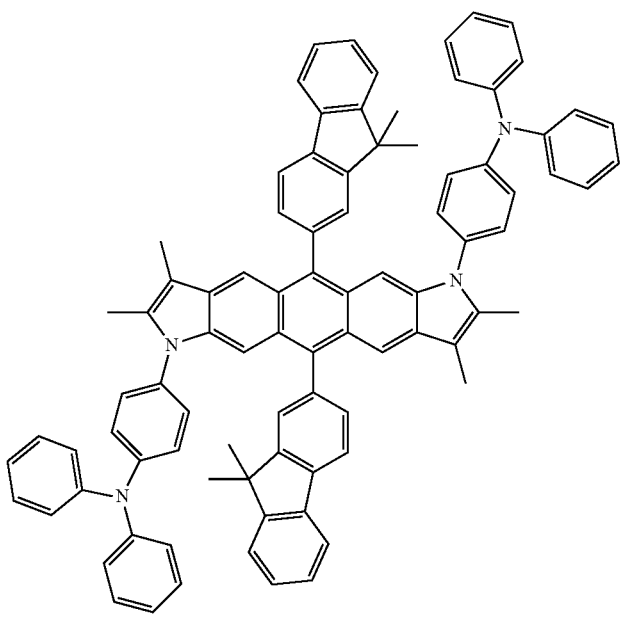
104

-continued
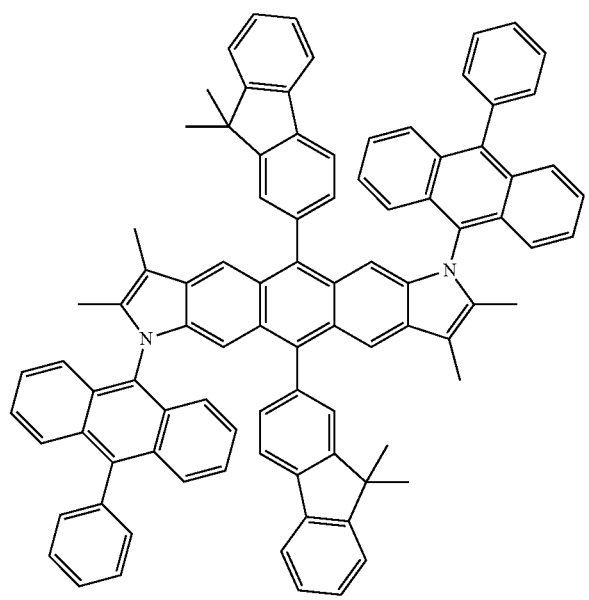
105
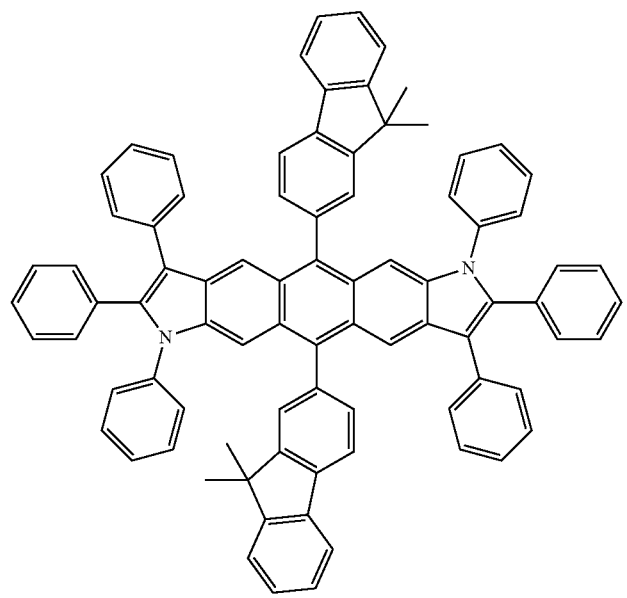
106

-continued
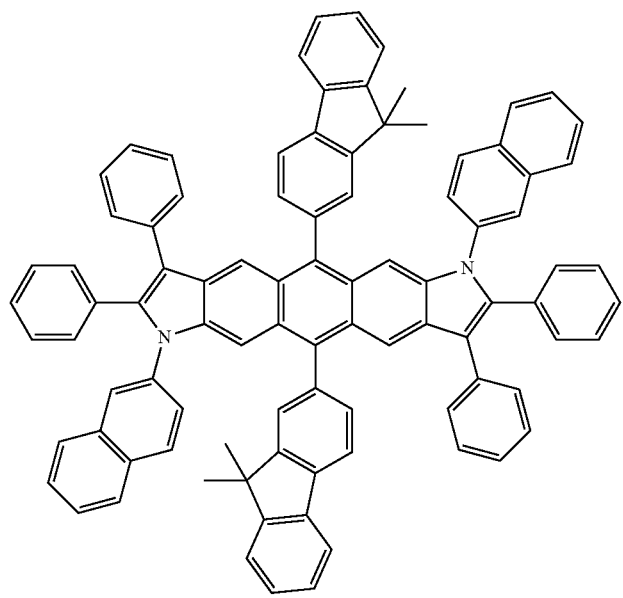
107
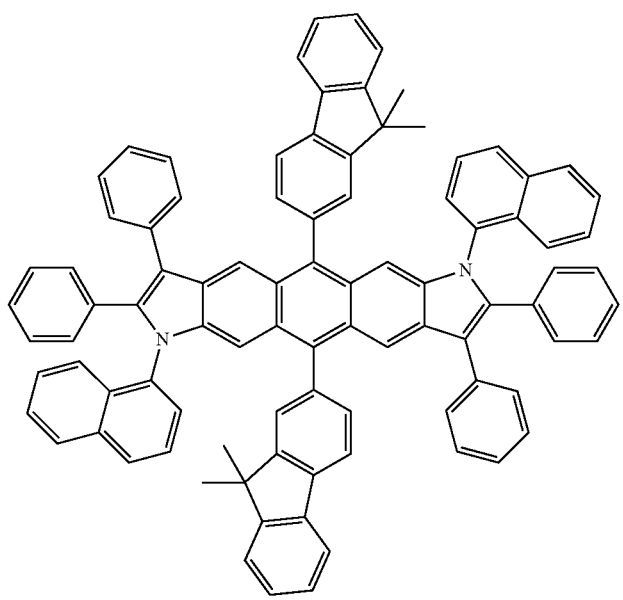
108

-continued
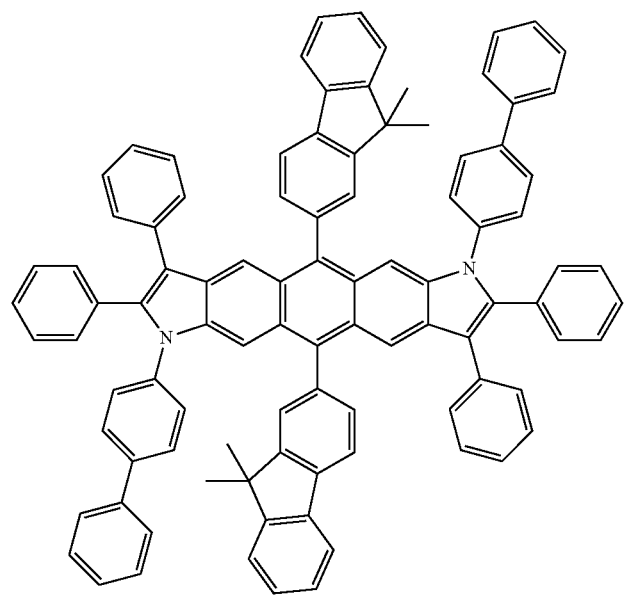
109
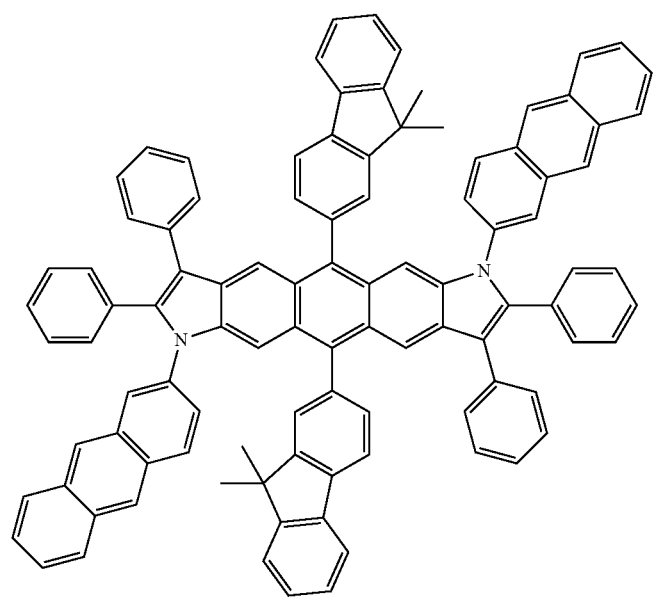
110

-continued
111
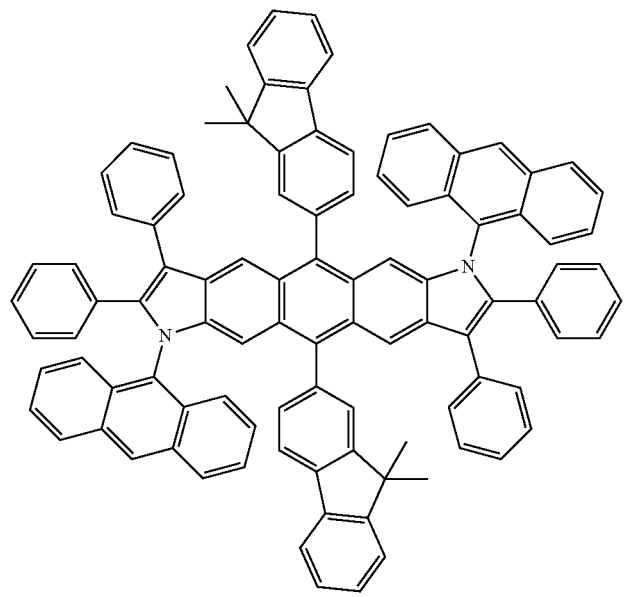
112
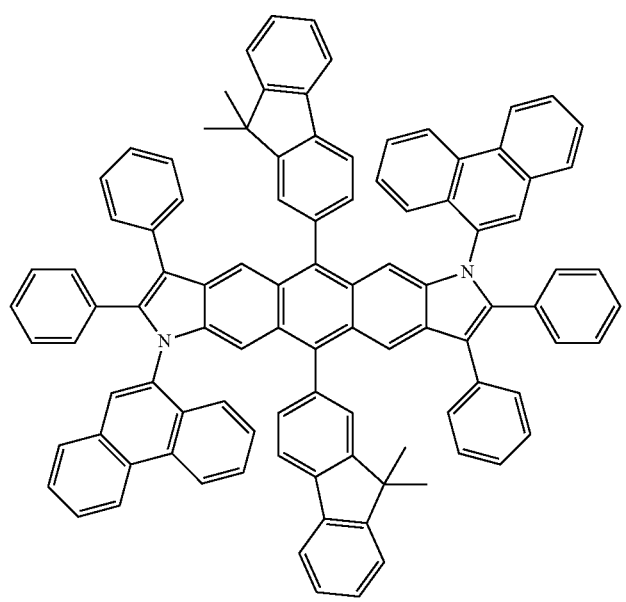

-continued
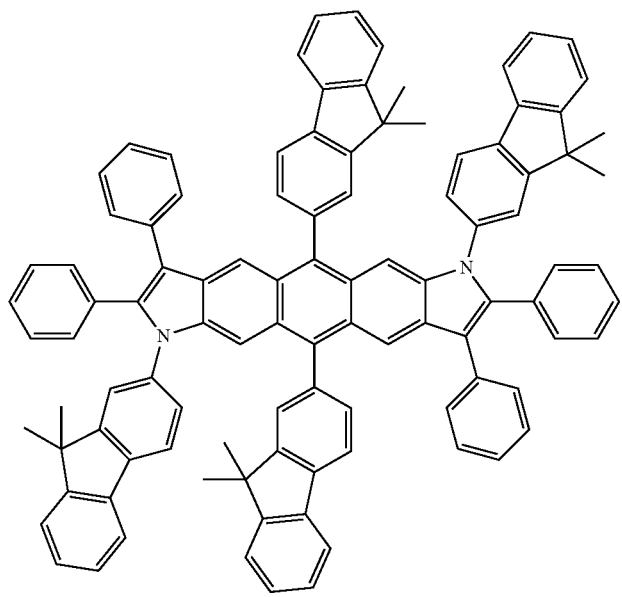
113
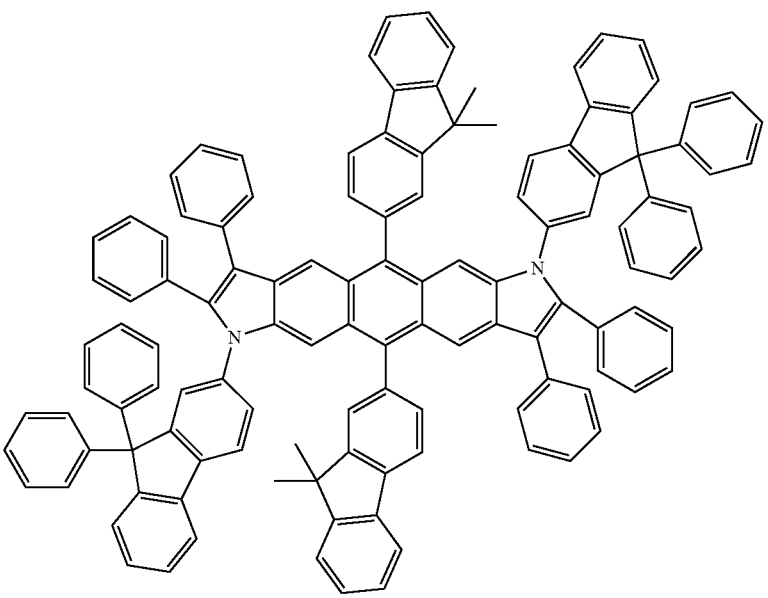
114

115
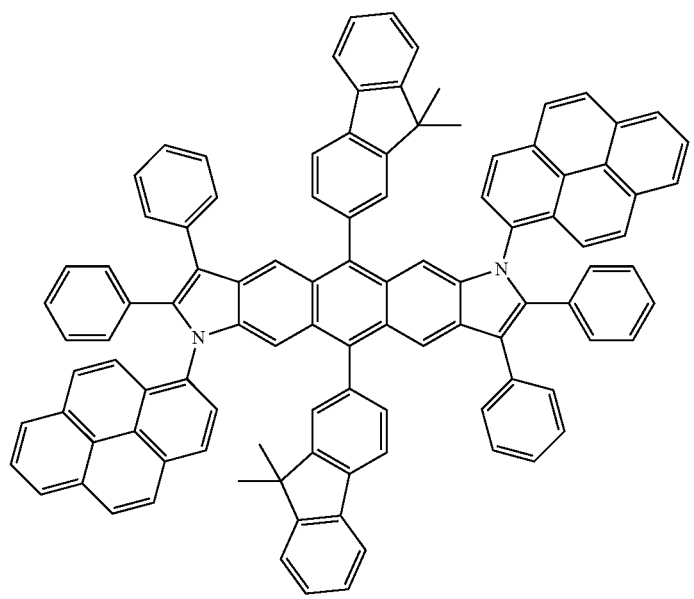
116
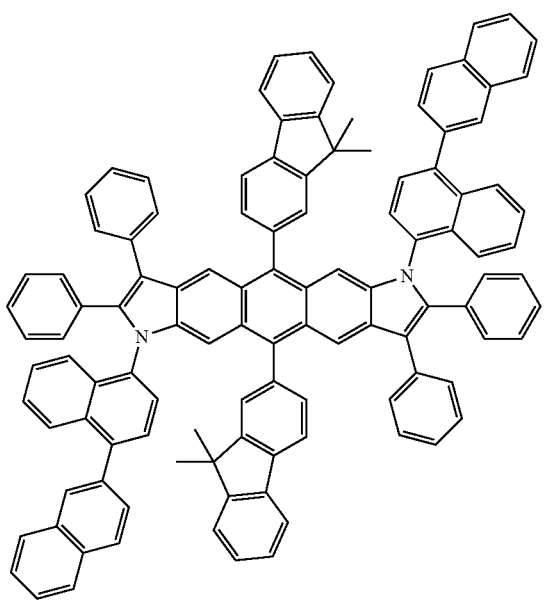

-continued
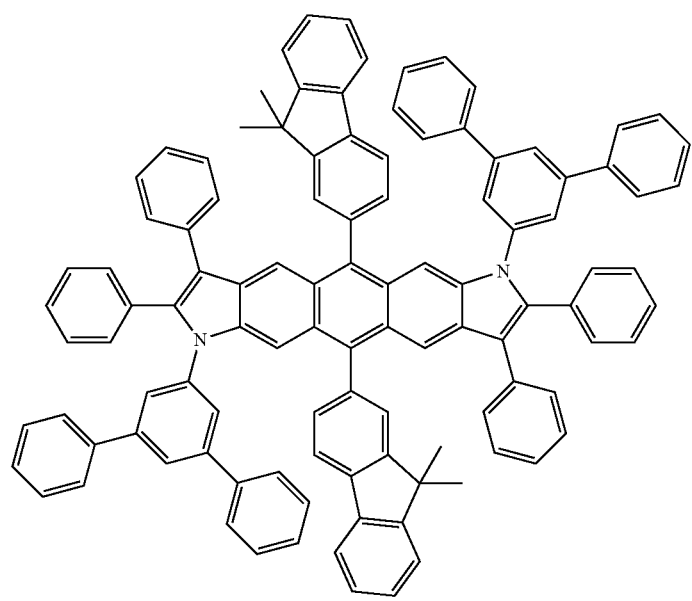
117
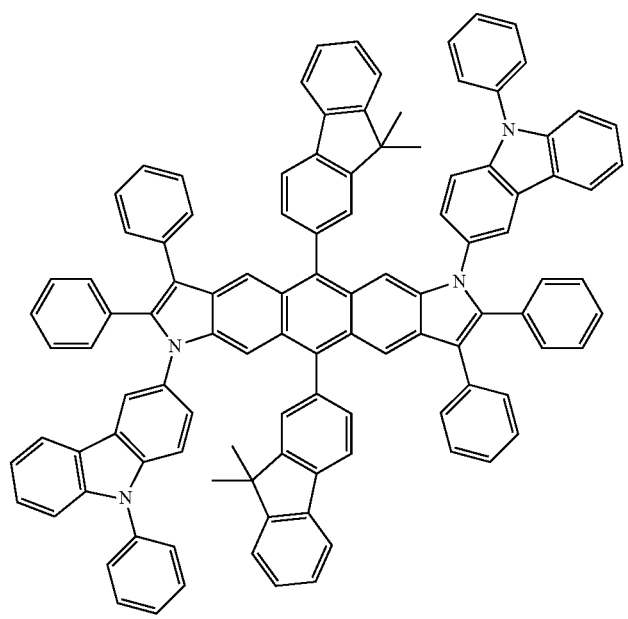
118

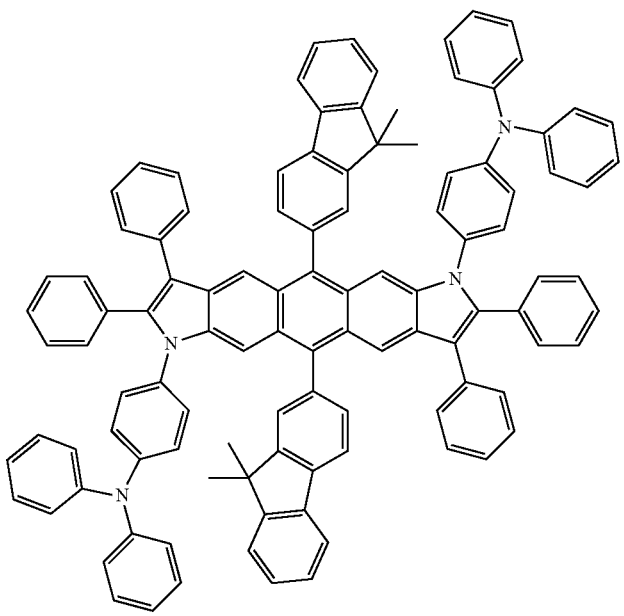

119

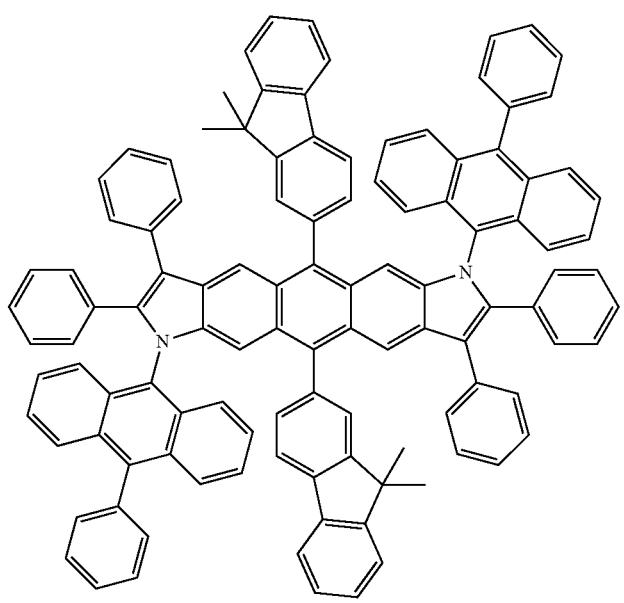

120

An organic light-emitting device according to embodiments of the present invention includes a first electrode, a second electrode, and an organic layer between the first electrode and the second electrode. The organic layer includes the heterocylic compound of Formula 1 described above.

The organic layer including the heterocyclic compound of Formula 1 may be an electron injection layer, a hole transport layer, or a single layer having both electron injection and electron transport capabilities. Alternatively, the organic layer including the heterocyclic compound of Formula 1 may be an emission layer. When the organic layer including the heterocyclic compound of Formula 1 is an emission layer, the heterocyclic compound of Formula 1 may be a fluorescent host, a phosphorescent host, or a fluorescent dopant.

According to embodiments of the present invention, when the emission layer, the hole injection layer or the hole transport layer includes the heterocyclic compound of Formula 1, the emission layer may include an anthracene compound, an arylamine compound or a styryl compound, where the anthracene compound, the arylamine compound or the styryl compound may be unsubstituted or substituted with a substituent such as those described with reference to the unsubstituted $C_1$-$C_{50}$ alkyl group.

In some embodiments of the present invention, when the hole injection layer or the hole transport layer includes the heterocyclic compound of Formula 1, a red emission layer, a green emission layer, a blue emission layer, or a white emission layer may include a fluorescent compound.

The first electrode may be an anode, and the second electrode may be a cathode, but the reverse is also possible.

The organic layer may further include at least one layer selected from a hole injection layer, a hole transport layer, an electron blocking layer, an emission layer, a hole blocking layer, an electron transport layer and an electron injection layer, if desired.

For example, an organic light-emitting device according to embodiments of the present invention may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. Alternatively, the organic light-emitting device may have a first electrode/ single layer having both hole injection and hole transport capabilities/emission layer/electron transport layer/second electrode structure, or a first electrode/single layer having both hole injection and hole transport capabilities/emission layer/electron transport layer/electron injection layer/second electrode structure.

According to embodiments of the present invention, the organic light emitting device may be a top-emission type organic light-emitting device or a bottom-emission type organic light-emitting device.

A method of manufacturing an organic light-emitting device according to embodiments of the present invention will now be described with reference to FIG. 1. FIG. 1 illustrates the structure of an organic light-emitting device according to an embodiment of the present invention. Referring to FIG. 1, an organic light-emitting device includes a substrate, a first electrode (anode), a hole injection layer (HIL), a hole transport layer (HTL), an emission layer (EML), an electron transport layer (ETL), an electron injection layer (EIL), and a second electrode (cathode).

First, the first electrode is formed on a substrate using a deposition or sputtering method. The first electrode may be formed of a first electrode material having a high work function. The first electrode may be an anode or a cathode. The substrate may be a substrate conventionally used in organic light-emitting devices, and may include, for example, a glass substrate or a transparent plastic substrate, which has excellent mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

Next, the HIL may be formed on the first electrode using various methods, for example, vacuum deposition, spin coating, casting, Langmuir-Blodgett (LB) deposition, or the like. When the HIL is formed using vacuum deposition, deposition conditions may vary according to the compound used to form the HIL, and the structure and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the compound used to form the HIL, and the structure and thermal properties of the HIL to be formed. For example, the coating conditions may include a coating speed of about 2000 rpm to about 5000 rpm, and a thermal treatment temperature of about 80° C. to about 200° C., wherein the thermal treatment serves to remove the solvent after coating.

The HIL material may include the heterocyclic compound of Formula 1 described above. Alternatively, known HIL materials may also be used. Nonlimiting examples of such HIL materials include phthalocyanine compounds such as copper phthalocyanine, 4,4',4"-tris(3-methylphenylphenylamino)triphenylamine (m-MTDATA), N,N'-di(1-naphthyl)-N,N'-diphenylbenzidine) (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/ PSS), polyaniline/camphor sulfonic acid (Pani/CSA), and (polyaniline)/poly(4-styrenesulfonate) (PANI/PSS).

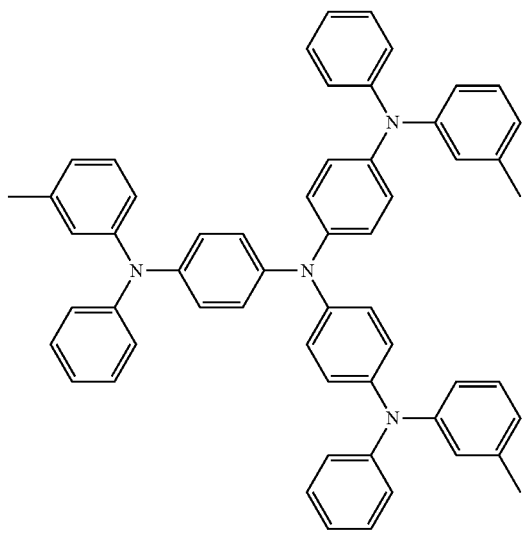

m-MTDATA

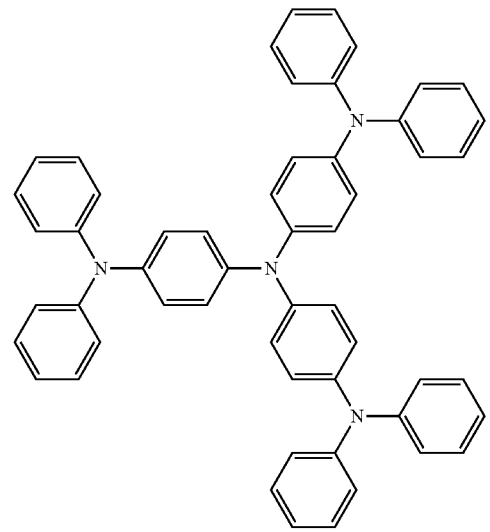

TDATA

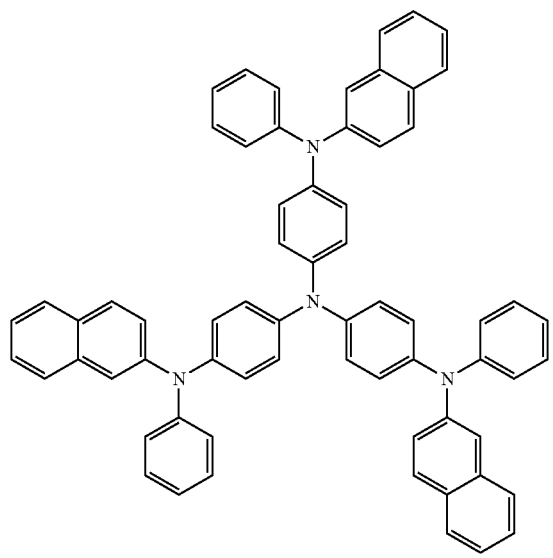

2-TNATA

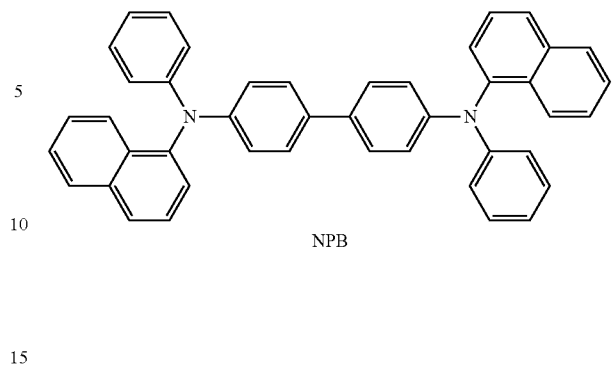

NPB

The HIL may have a thickness of about 100 Å to about 10,000 Å. For example, the HIL may have a thickness of about 100 Å to about 1000 Å. When the HIL has a thickness within these ranges, the HIL may have good hole injection characteristics without an increase in driving voltage.

Next, the HTL may be formed on the HIL using various methods, for example vacuum deposition, spin coating, casting, LB deposition, or the like. When the HTL is formed using vacuum deposition or spin coating, the deposition or coating conditions may be similar to those used to form the HIL, although the deposition or coating conditions may vary according to the material that is used to form the HTL.

The HTL material may include the heterocyclic compound of Formula 1 described above. Alternatively, known HTL materials may be used. Nonlimiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD). Among these materials, TCTA may not only transport holes but also inhibit excitons from being diffused from the EML.

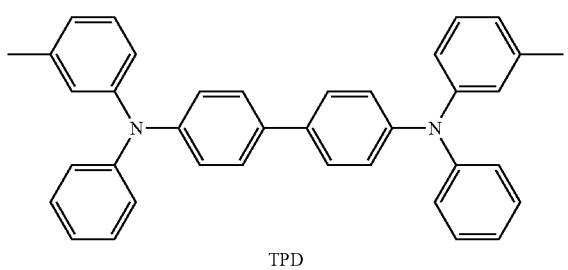

TPD

The HTL may have a thickness of about 50 Å to about 1000 Å. For example, the HTL may have a thickness of about 100 Å to about 600 Å. When the HTL has a thickness within these ranges, the HTL may have good hole transport characteristics without a substantial increase in driving voltage.

Next, the EML may be formed on the HTL using various methods, for example, vacuum deposition, spin coating, casting, LB deposition, or the like. When the EML is formed using vacuum deposition or spin coating, the deposition or coating conditions may be similar to those used to form the HIL, although the deposition and coating conditions may vary according to the material that is used to form the EML.

The EML may include the heterocyclic compound of Formula 1 described above. In particular, the heterocyclic compound of Formula 1 may be used as a host or a dopant. The EML may be formed using a variety of known light-emitting materials, in addition to the heterocyclic compound of Formula 1. Alternatively, the EML may be formed using a known host and a dopant. The dopant used to form the EML may include either a fluorescent dopant or a phosphorescent dopant.

Nonlimiting examples of suitable hosts include Alq$_3$, CPB (4,4'-N,N'-dicarbazole-biphenyl), 9,10-di(naphthalen-2-yl)anthracene (ADN), and distyrylarylene (DSA).

Nonlimiting examples of red dopants include platinum(II) octaethylporphyrin (PtOEP), Ir(piq)$_3$, Btp$_2$Ir(acac), and DCJTB.

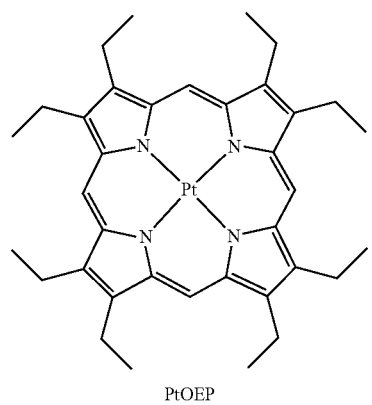

PtOEP

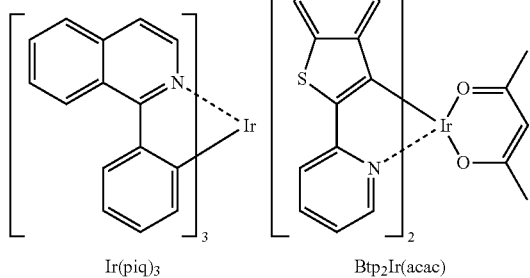
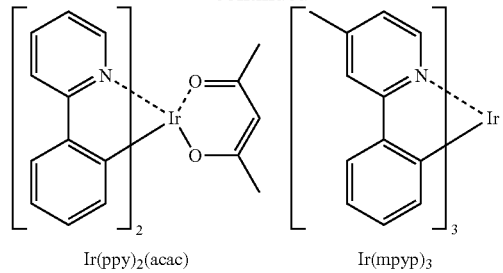
Nonlimiting examples of green dopants include Ir(ppy)₃ (where "ppy" denotes phenylpyridine), Ir(ppy)₂(acac), Ir(m-pyp)₃, and C545T.
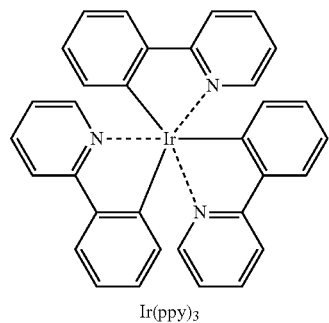
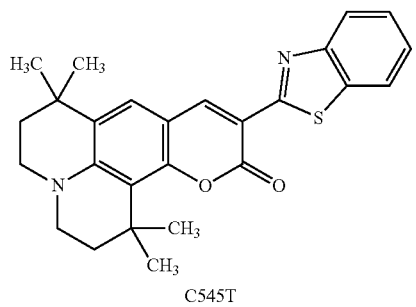
Nonlimiting examples of blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl phenylene (TBP).
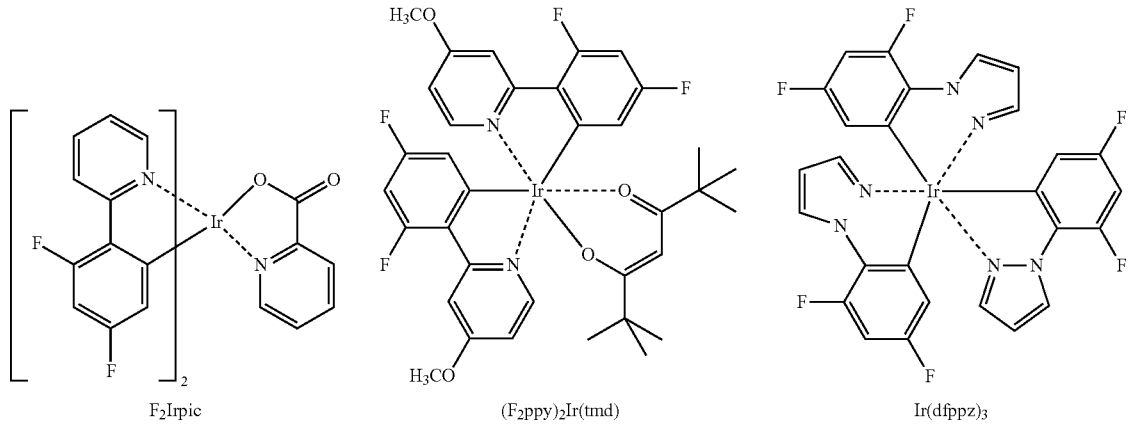
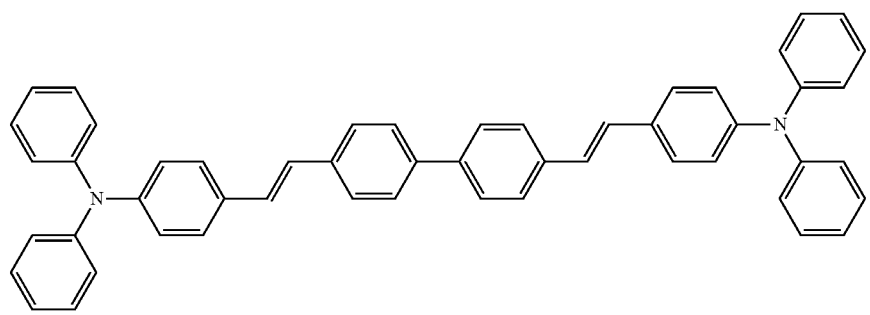

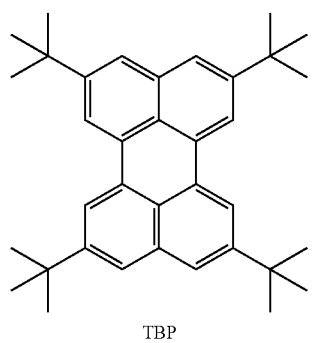
TBP

The amount of the dopant may be about 0.1 to about 20 parts by weight, or about 0.5 to about 12 parts by weight, based on 100 parts by weight of the EML material (which is equivalent to the total weight of the host and the dopant). When the amount of the dopant is within these ranges, concentration quenching may be substantially prevented.

The EML may have a thickness of about 100 Å to about 1000 Å. For example, the EML may have a thickness of about 200 Å to about 600 Å. When the EML has a thickness within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form a HBL, without limitation. Nonlimiting examples of such HBL materials include oxadiazole derivatives, triazole derivatives, phenathroline derivatives, Balq, and BCP.

The HBL may have a thickness of about 50 Å to about 1000 Å. For example, the HBL may have a thickness of about 100 Å to about 300 Å. When the HBL has a thickness within these ranges, the HBL may have excellent hole blocking characteristics without a substantial increase in driving voltage.

Next, the ETL is formed on the EML (or HBL) using various methods, for example, vacuum deposition, spin coating, casting, or the like. When the ETL is formed using vacuum deposition or spin coating, the deposition or coating conditions may be similar to those used to form the HIL, although the deposition and coating conditions may vary according to the material that is used to form the ETL.

The ETL material may include the heterocyclic compound of Formula 1 described above. Alternatively, the ETL may be formed of any known material. Nonlimiting examples of such ETL materials include quinoline derivatives, such as tris(8-quinolinolate)aluminum (Alq₃), TAZ, or Balq.

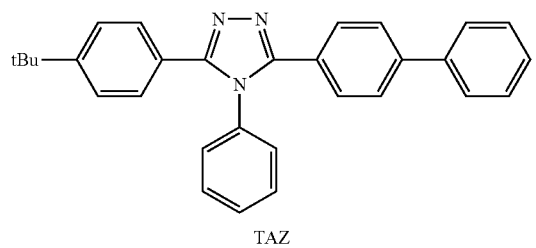
TAZ

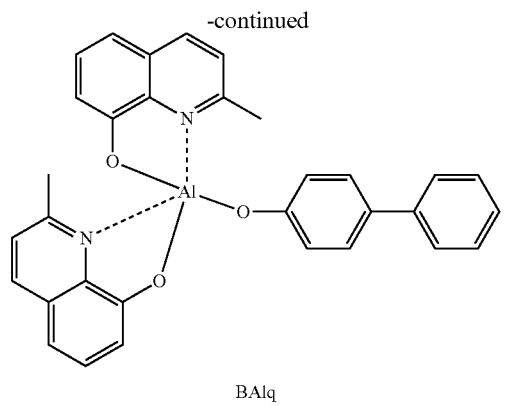
BAlq

The ETL may have a thickness of about 100 Å to about 1000 Å. For example, the ETL may have a thickness of about 100 Å to about 500 Å. When the ETL has a thickness within these ranges, the ETL may have good electron transport characteristics without a substantial increase in driving voltage.

In addition, the EIL, which facilitates injection of electrons from the cathode, may be formed on the ETL. An EIL material may include the heterocyclic compound of Formula 1 described above. Alternatively, known EIL materials, such as LiF, NaCl, CsF, Li₂O, or BaO, may be used to form the EIL. The deposition or coating conditions may be similar to those used to form the HIL, although the deposition and coating conditions may vary according to the material that is used to form the EIL.

The EIL may have a thickness of about 1 Å to 100 Å. For example, the EIL may have a thickness of about 5 Å to about 90 Å. When the EIL has a thickness within the above range, the EIL may have good electron injection characteristics without a substantial increase in driving voltage.

Finally, the second electrode may be formed on the EIL using, for example, vacuum deposition, sputtering, or the like. The second electrode may be a cathode or an anode. A second electrode material may include a metal, an alloy, an electrically conductive compound, or mixtures thereof, all of which have low work functions. Nonlimiting examples of such materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used as the second electrode.

The organic light-emitting device according to embodiments of the present invention may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

According to embodiments of the present invention, at least one layer of the organic light-emitting device may be formed of the heterocyclic compound of Formula 1 and may be formed using a deposition method or a wet method of coating a solution of the heterocylic compound of Formula 1.

The following Examples are presented for illustrative purposes only, and do not limit the scope of the present invention.

EXAMPLES

Synthesis Example 1

Synthesis of Compound 11

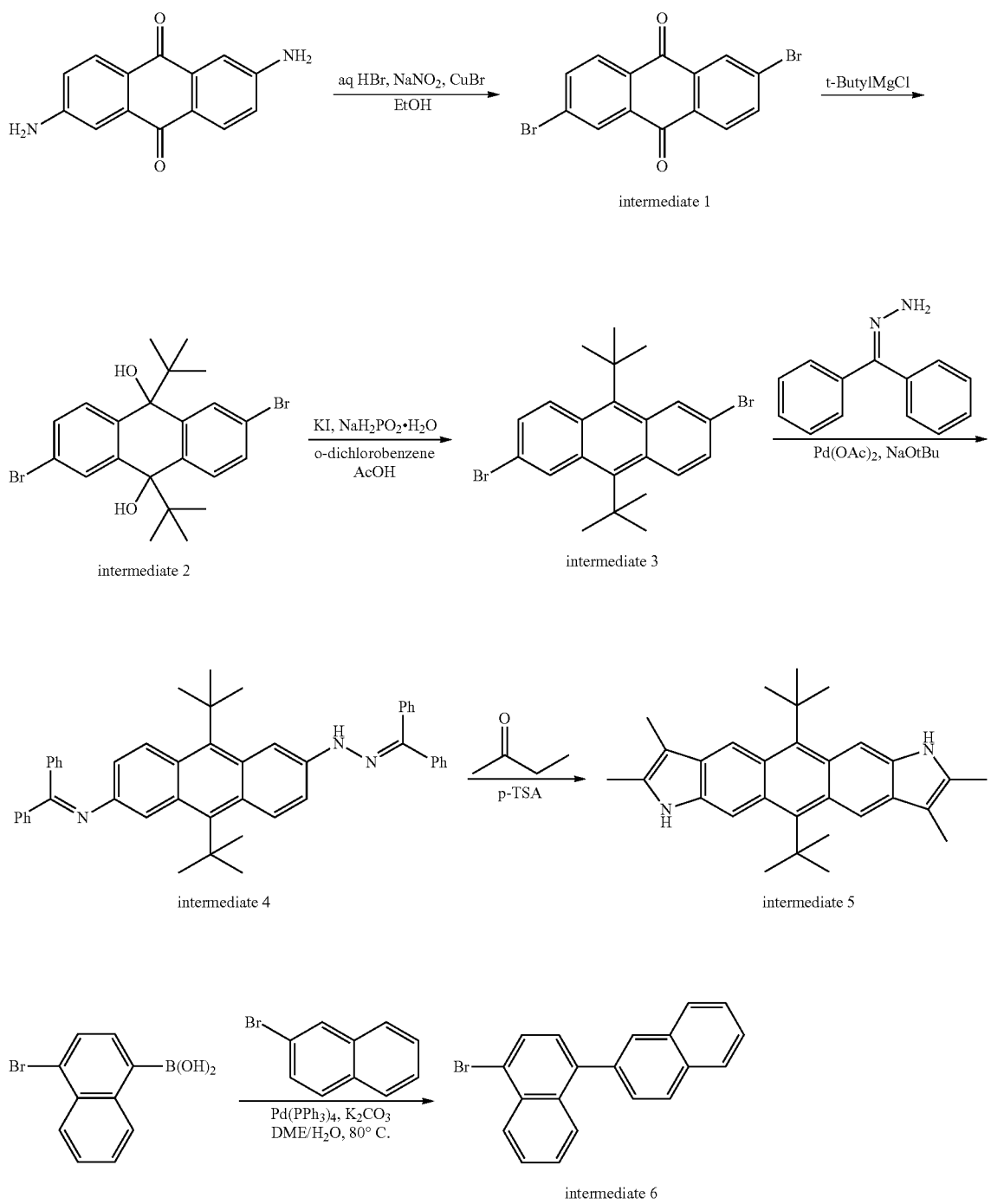

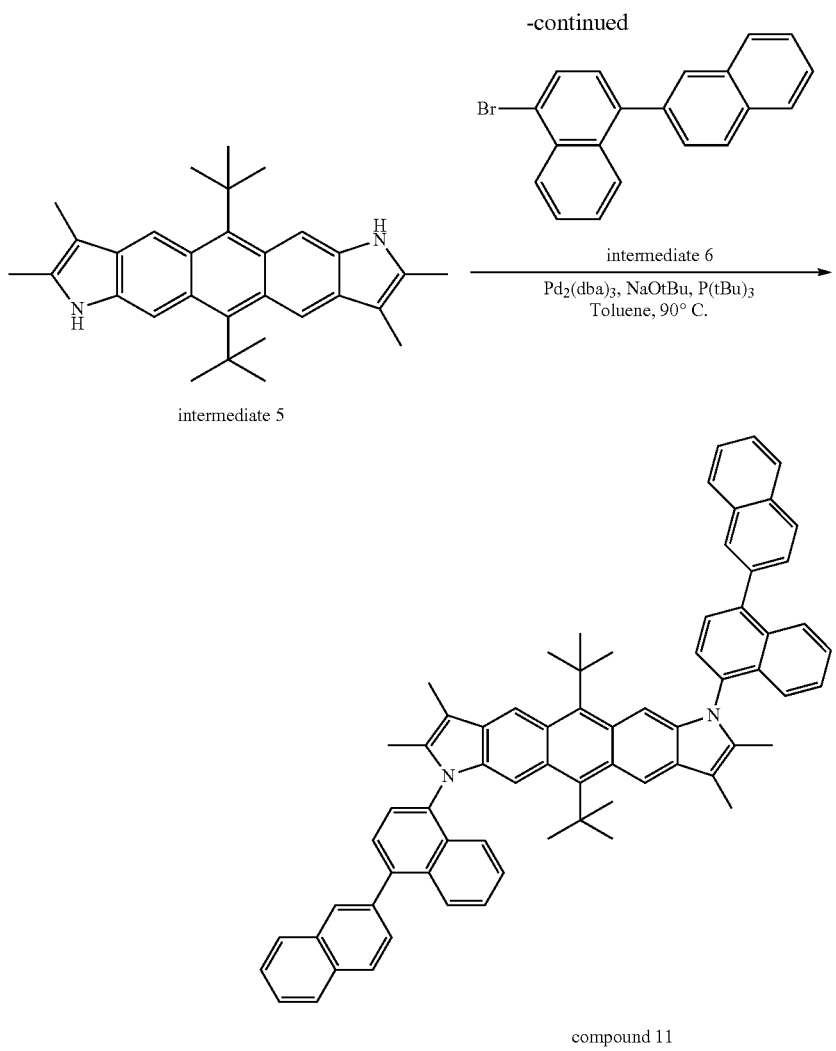

Synthesis of Intermediate 1

2.38 g (10 mmol) of 2,6-diaminoanthraquinone was dispersed in a 48 weight % HBr aqueous solution, and then 1.41 g (20.4 mmol) of NaNO$_2$ was slowly added thereto at a temperature of 20° C. When gas was no longer generated, a solution obtained by dissolving 2.95 g (20.6 mmol) of CuBr in 3 mL of 48 weight % HBr aqueous solution was slowly added thereto together with 5.0 mL of ethanol. The reaction temperature was increased to room temperature, and reflux was performed for 1 hour. The temperature was cooled to room temperature and then the precipitate generated by adding water was filtered and the filtrate was washed with water and vacuum dried. The obtained solid was dissolved with chloroform and passed through silica gel, and then subjected to reduced pressure to remove solvent. The precipitate was separated and purified using silica gel column chromatography to obtain 1.0 g (yield 28%) of intermediate 1, and this compound was identified using high-resolution mass spectra (HR-MS).

Synthesis of Intermediate 2

3.66 g (10 mmol) of Intermediate 1 was dissolved in 50 mL of tetrahydrofuran (THF) and cooled to −78° C., and 15 mL (2.0 M in diethylether) of tertiary-buty magnesium chloride was slowly added to the solution in a nitrogen atmosphere. Stirring was performed at the same temperature for 30 minutes and then, a cooling device was removed and the temperature was increased to room temperature. Stirring was performed for one hour and then, when the reaction was complete, the temperature was cooled to 0° C. and 10 mL of ammonium chloride aqueous solution was slowly added thereto. The reaction product was extracted twice using 40 mL of diethylether and then the collected organic layer was dried over magnesium sulfate, followed by filtration. Solvent was evaporated, and the residue was separated and purified using silica gel column chromatography to obtain 3.1 g of (yield: 65%) Intermediate 2. This compound was identified using HR-MS.

Synthesis of Intermediate 3

A mixture including 3.1 g (6.43 mmol) of Intermediate 2, 10.7 g (64.7 mmol) of potassiumiodide, and 11.4 g (129 mmol) of sodiumhydrophosphite hydrate was refluxed in a mixed solution including 600 mL of ortho-dichlorobenzene and 80 mL of acetic acid for 24 hours. The reaction product was cooled to room temperature and then extracted with chloroform and dried using anhydrous magnesium sulfate and subjected to reduced pressure to remove solvent. The obtained residue was separated and purified by silica gel column chromatography to obtain 2.0 g (yield: 69%) of Intermediate 3. This compound was identified using HR-MS.

Synthesis of Intermediate 4

2.0 g (4.5 mmol) of Intermediate 3, 1.92 g (9.8 mmol) of benzophenone hydrazone, 1.3 g (13.6 mmol) of t-BuONa, 40 mg (0.2 mmol) of Pd(OAc)$_2$, and 96 mg (0.2 mmol) of 2-Dicyclohexylphosphino-2',4',6'-triisopropylbiphenyl were dissolved in 30 mL of toluene and stirred at 90° C. for 3 hours. The reaction product was cooled to room temperature. Distilled water was added thereto. The resultant solution was extracted twice with 80 mL of diethylether and once with 80 mL of dichloromethane. The organic layer was collected and dried using magnesium sulfate, followed by filtration. Solvent was evaporated, and the residue was separated and purified by silica gel column chromatography to obtain 2.5 g (yield: 82%) of Intermediate 4. This compound was identified using HR-MS.

Synthesis of Intermediate 5

30 mL of methylethylketone was added to 2.5 g (3.8 mmol) of Intermediate 4 and 1.4 g (15 mmol) of p-toluenesulfonicacid monohydrate, and then the resultant solution was stirred at a temperature of 110° C. for 24 hours. The reaction product was cooled to room temperature. Distilled water was added thereto and then, the solution was extracted twice with 100 mL of diethylether and twice with 40 mL of dichloromethane. An organic layer was collected and dried using magnesium sulfate, followed by filtration. Solvent was evaporated, and the residue was separated and purified using silica gel column chromatography to obtain 1.2 g (yield: 77%) of Intermediate 5. This compound was identified using HR-MS.

Synthesis of Intermediate 6

2.51 g (10 mmol) of 1-bromo-4-naphthalene boric acid, 2.07 g (10 mmol) of 2-boromonaphthalene, 0.58 g (0.5 mmol) of Pd(PPh$_3$)$_4$, and 5.53 g (40 mmol) of K$_2$CO$_3$ were dissolved in 100 ml of a mixed solution of THF/H$_2$O (2:1), and stirred at 80° C. for 5 hours. The mixture was subjected to extraction three times with 100 mL of diethyl ether. An organic layer was collected and dried using magnesium sulfate to evaporate the solvent. The residue was recrystallized with dichloromethane and normal hexane to obtain 2.5 g (yield: 76%) of Intermediate 6. This compound was identified using HR-MS.

Synthesis of Compound 11

Under a N$_2$ atmosphere, 2.97 g (7.0 mmol) of Intermediate 5, 5.6 g (16.8 mmol) of Intermediate 6, 4.0 g (42 mmol) of t-BuONa, 260 mg (0.28 mmol) of Pd$_2$(dba)$_3$, and 56 mg (0.28 mmol) of P(t-Bu)$_3$ were dissolved in 60 ml of toluene, and then the mixture was stirred at a temperature of 90° C. for 3 hours. After the reaction was completed, the reaction product was cooled to room temperature and extracted three times with distilled water and 50 ml of diethylether. An organic layer was collected and dried using magnesium sulfate to evaporate the solvent. The residue was separated and purified using silica gel column chromatography to obtain 4 g (yield: 68%) of Compound 11. This compound was identified using HR-MS. (calc.; 928.4756, found; 928.4745) (1H-NMR, 400 MHz, CD2Cl2: δ8.02-7.37 (m,30H), δ2.30 (s,6H), δ2.25 (s,6H), δ 1.47 (s,18H), 13C-NMR: 143.5, 136.1, 134.5, 133.2, 132.1, 130.5, 130.2, 129.3, 128.7, 128.6,128.4, 128.0, 126.3, 124.8, 124.5, 124.3, 123.3, 123.1, 121.5, 121.9, 121.4, 121.1, 120.5, 120.4, 120.0, 116.3, 115,8, 32.3, 31.4, 7.0, 5.3).

Synthesis Example 2

Synthesis of Compound 29

Synthesis of Intermediate 7

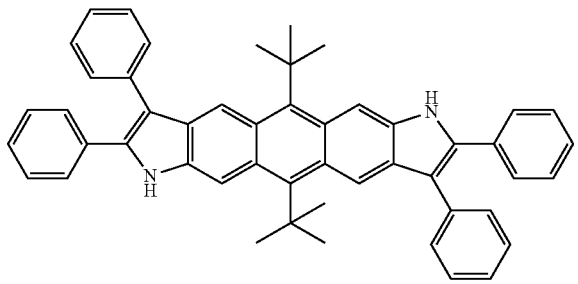

intermediate 7

1.2 g (3.0 mmol) of Intermediate 4, 2.28 g (12.0 mmol) of p-toluenesulfonic acid monohydrate, and 2.4 g (12.0 mmol) of benzylphenylketone were dissolved in 16 mL of ethanol and 4 mL of toluene and stirred at 110° C. for 24 hours. The reaction product was cooled to room temperature. Distilled water was added thereto and the resultant solution was extracted twice with 25 mL of diethylether and twice with 25 mL of dichloromethane. The organic layer was collected and dried using magnesium sulfate, followed by filtration. The solvent was evaporated, and the residue was separated and purified using silica gel column chromatography to obtain 1.5 g (yield: 76%) of Intermediate 7. This compound was identified using HR-MS.

Synthesis of Compound 29

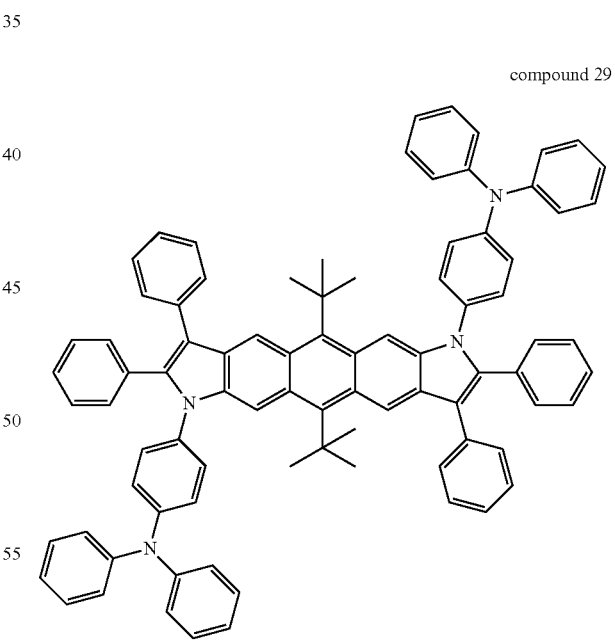

compound 29

Compound 29 was synthesized with a yield of 71% in the same manner as Compound 11, except that Intermediate 7 was used instead of Intermediate 5, and (4-boromophenyl)-diphenylamine was used instead of Intermediate 6. This compound was identified using HR-MS. (calc.; 1158.5600, found; 1158.5612) (1H-NMR, 400 MHz, CD2Cl2: δ8.01-6.50 (m,52H), δ1.50 (s,18H), 13C-NMR: 143.4, 136.9, 134.4, 134.2, 131.1, 131.5, 130.2, 129.3, 128.7, 128.6,128.4, 128.0, 126.3, 124.8, 124.5, 124.3, 123.3, 121.5, 121.9, 121.4, 121.1, 120.4, 116.3, 115,8, 32.3, 31.4, 7.2, 5.4).

Synthesis Example 3

Synthesis of Compound 43

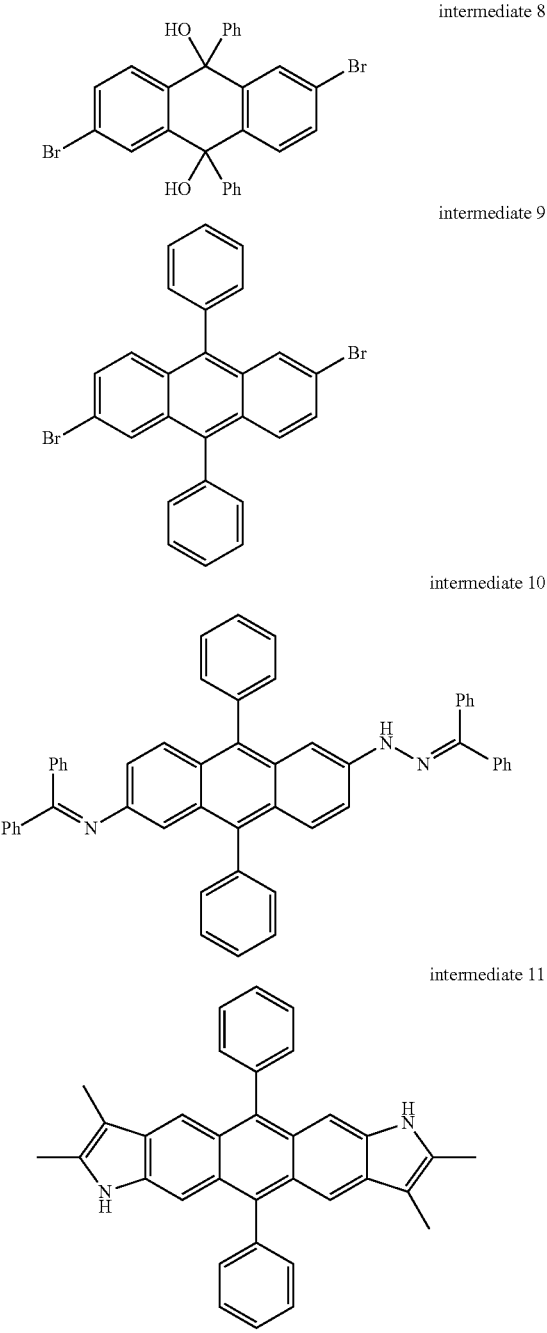

Synthesis of Intermediate 8

Intermediate 8 was synthesized with a yield of 65% in the same manner as Intermediate 2, except that phenyl magnesium chloride (2.0M in THF) was used instead of tertiary-butyl magnesium chloride. This compound was identified using HR-MS.

Synthesis of Intermediate 9

Intermediate 9 was synthesized with a yield of 52% in the same manner as

Intermediate 3, except that Intermediate 8 was used instead of Intermediate 3. This compound was identified using HR-MS.

Synthesis of Intermediate 10

Intermediate 10 was synthesized with a yield of 68% in the same manner as

Intermediate 4, except that Intermediate 9 was used instead of Intermediate 3. This compound was identified using HR-MS.

Synthesis of Intermediate 11

Intermediate 11 was synthesized with a yield of 75% in the same manner as

Intermediate 5, except that Intermediate 10 was used instead of Intermediate 4. This compound was identified using HR-MS.

Synthesis of Compound 43

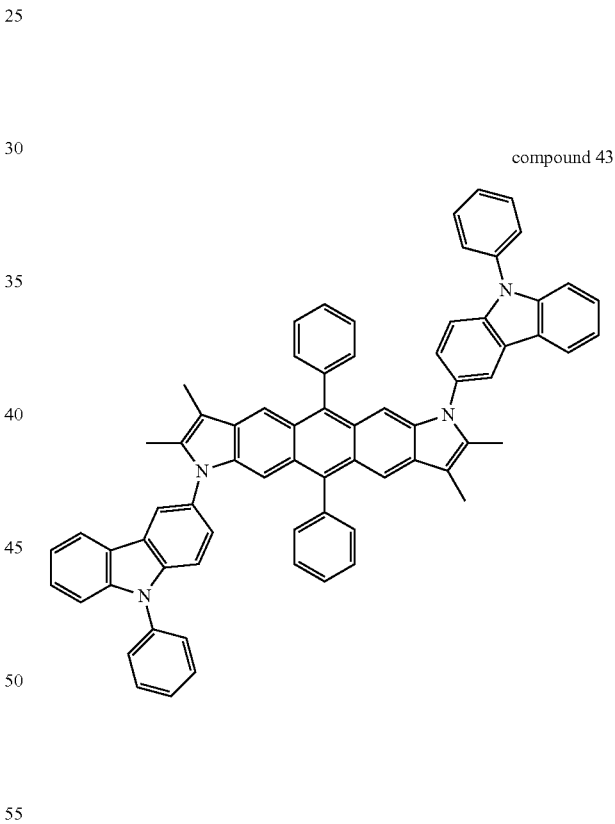

Compound 43 was synthesized with a yield of 73% in the same manner as Compound 11, except that Intermediate 11 was used instead of Intermediate 5, and 3-iodo-9-phenylcarbazole was used instead of Intermediate 6. This compound was identified using HR-MS. (calc.; 946.4035, found; 946.4025), (1 H-NMR, 400 MHz, CD2C12: δ8.21-7.80 (m,4H), δ7.65-6.90 (m,4H), δ2.30 (s,6H), δ2.21 (s,6H) 13C-NMR: 143.4, 136.9, 136.2, 134.4, 134.2, 131.1, 131.5, 130.2, 129.3, 128.7, 128.6,128.4, 128.0, 127.6, 126.3, 124.8, 124.5, 124.3, 123.9, 123.3, 121.5, 121.9, 121.4, 121.1, 120.4, 116.3, 115,8, 12.5, 10.8).

Synthesis Example 4

Synthesis of Compound 56

Synthesis of Intermediate 12

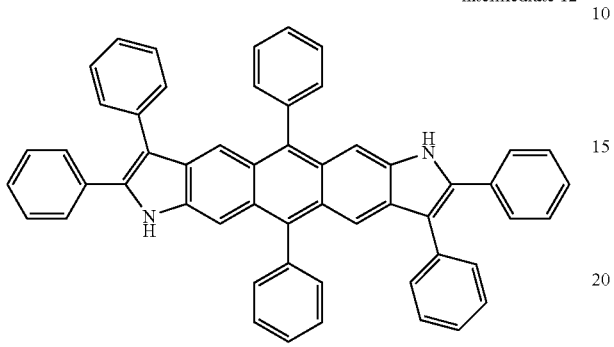

intermediate 12

Intermediate 12 was synthesized with a yield of 68% in the same manner as Intermediate 7, except that Intermediate 10 was used instead of Intermediate 4. This compound was identified using HR-MS.

Synthesis of Compound 56

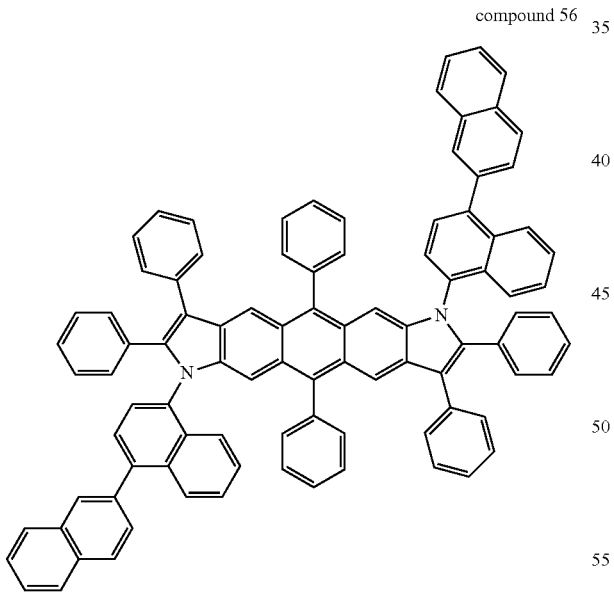

compound 56

Compound 56 was synthesized with a yield of 70% in the same manner as Compound 11, except that Intermediate 12 was used instead of Intermediate 5, and 1-(2-naphthyl)-4-naphthalene boric acid was used instead of Intermediate 6. This compound was identified using HR-MS. (calc.; 1216.4756, found; 1216.4745), (1H-NMR, 400 MHz, CD2Cl2: δ7.80-6.90 (m,60H) 13C-NMR: 138.4, 136.9, 136.2, 135.4, 135.1, 133.4, 133.1, 132.6, 131.2, 131.1, 131.0, 130.6, 130.2, 129.6, 129.3, 128.7, 128.6, 128.4, 128.0, 127.6, 127.2, 126.3, 125.5, 125.1, 124.8, 124.5, 124.3, 123.9, 123.3, 121.5, 121.9, 121.4, 121.1, 120.4, 116.3, 115.8).

Synthesis Example 5

Synthesis of Compound 74

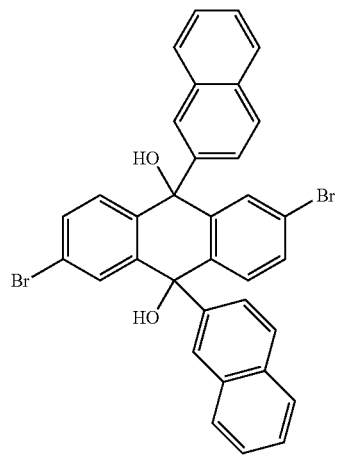

intermediate 13

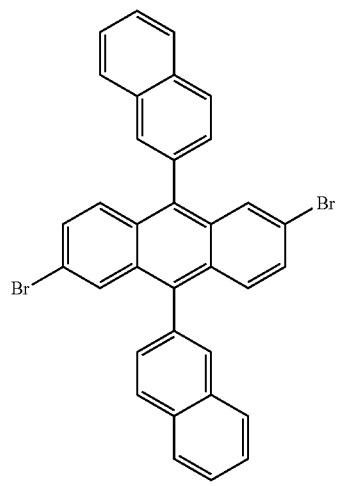

intermediate 14

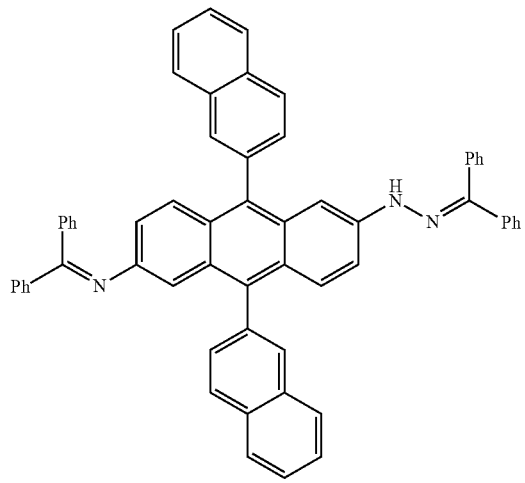

intermediate 15

-continued intermediate 16

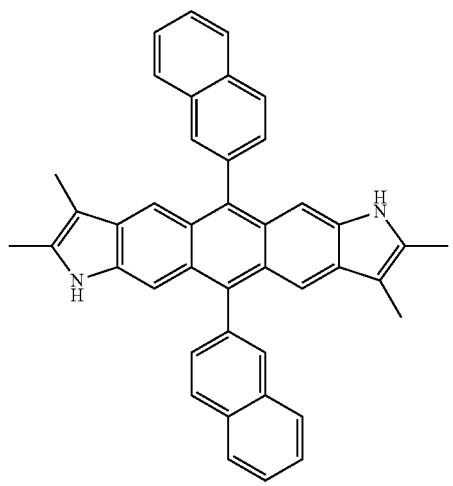

Synthesis of Intermediate 13

Intermediate 13 was synthesized with a yield of 55% in the same manner as Intermediate 2, except that 2-naphthylmagnesiumbromide (0.5 M in THF) was used instead of tertiary-butyl magnesium chloride. This compound was identified using HR-MS.

Synthesis of Intermediate 14

Intermediate 14 was synthesized with a yield of 61% in the same manner as Intermediate 3, except that Intermediate 13 was used instead of Intermediate 3. This compound was identified using HR-MS.

Synthesis of Intermediate 15

Intermediate 15 was synthesized with a yield of 73% in the same manner as Intermediate 4, except that Intermediate 14 was used instead of Intermediate 3. This compound was identified using HR-MS.

Synthesis of Intermediate 16

Intermediate 16 was synthesized with a yield of 71% in the same manner as Intermediate 5, except that Intermediate 15 was used instead of Intermediate 4. This compound was identified using HR-MS.

Synthesis of Compound 74 compound 74

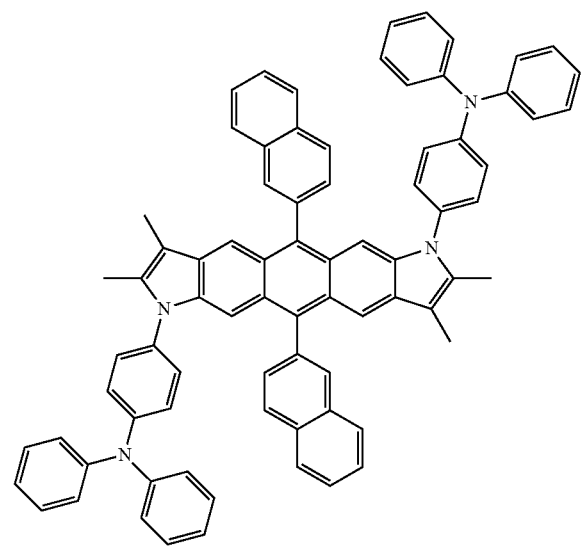

Compound 74 was synthesized with a yield of 74% in the same manner as Compound 11, except that Intermediate 16 was used instead of Intermediate 5, and (4-bromophenyl)-diphenylamine was used instead of Intermediate 6. This compound was identified using HR-MS. (calc.; 1050.4661, found; 1050.4654), (1H-NMR, 400 MHz, CD2Cl2: δ7.80-6.90 (m,46H), δ2.13 (s,6H), δ2.03 (s,6H), 13C-NMR: 139.4, 138.9, 136.9, 135.3, 135.0, 133.1, 131.1, 131.0, 129.6, 129.3, 128.7, 128.6, 128.4, 128.0, 127.6, 127.2, 126.3, 125.5, 124.5, 124.3, 123.9, 123.3, 121.5, 121.9, 121.4, 121.1, 115,8.13.2, 11.4).

Synthesis Example 6

Synthesis of Compound 82

Synthesis of Intermediate 17 intermediate 17

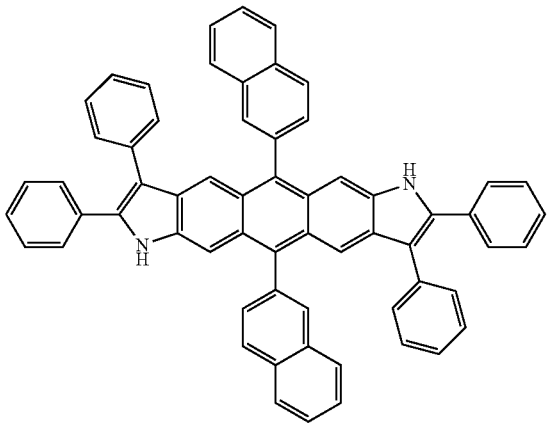

Intermediate 17 was synthesized with a yield of 75% in the same manner as Intermediate 7, except that Intermediate 15 was used instead of Intermediate 4. This compound was identified using HR-MS.

Synthesis of Compound 82 compound 82

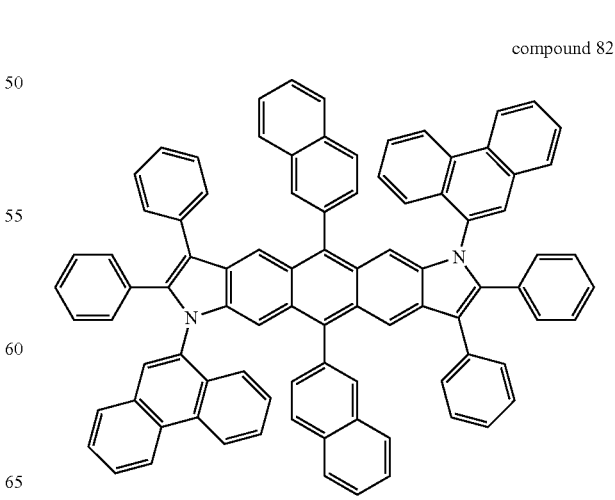

Compound 82 was synthesized with a yield of 66% in the same manner as Compound 11, except that Intermediate 17 was used instead of Intermediate 5, and 9-bromophenanthrene was used instead of Intermediate 6. This compound was identified using HR-MS. (calc.; 1164.4443, found; 1164.4434), (1H-NMR, 400 MHz, CD2Cl2: δ7.80-6.90 (m,56H), 13C-NMR: 142.2, 141.5, 140.5, 139.0, 138.4, 136.9, 136.0, 135.7, 135.1, 133.4, 133.1, 132.6, 131.2, 131.0, 130.6, 130.2, 129.6, 129.1, 128.7, 128.6, 128.4, 128.0, 127.6, 125.3, 125.5, 125.1, 124.8, 124.5, 124.3, 123.9, 123.3, 122.5, 121.9, 121.4, 121.1, 120.6, 116.5, 115,4).

Example 1

An anode was prepared by cutting a Corning 15 Ωcm² (1200 Å) ITO glass substrate to a size of 50 mm×50 mm×0.7 mm, ultrasonically cleaning the glass substrate using isopropyl alcohol and pure water for 5 minutes each, and then irradiating UV light for 30 minutes and exposing to ozone to clean. Then, the anode was mounted in a vacuum deposition apparatus.

2-TNATA was vacuum-deposited on the glass substrate to form a HIL having a thickness of 600 Å, and then 4,4'-bis[N-(1-naphthyl)-N-phenylamino]biphenyl (hereinafter referred to as NPB) was vacuum deposited on the HIL to form a HTL having a thickness of 300 Å.

Then, Alq₃ (as a green fluorescent host), and Compound 11 (as a green fluorescent dopant) were simultaneously deposited in a weight ratio of 98:2 on the HTL, to form an EML having a thickness of 300 Å.

Then, Alq₃ was deposited on the EML to form an ETL having a thickness of 300 Å, and then LiF, which is a halogenated alkali metal, was deposited on the ETL to form an EIL having a thickness of 10 Å. Then, Al was deposited on the EIL to a thickness of 3000 Å (cathode), thereby forming a LiF/Al electrode. As a result, the manufacture of an organic light-emitting device was completed.

The organic light-emitting device had a driving voltage of 6.20 V at a current density of 50 mA/cm², a high emission brightness of 8,642 cd/m², and an emission efficiency of 18.70 cd/A.

Example 2

An organic light-emitting device was manufactured in the same manner as in Example 1, except that Compound 29 was used instead of Compound 11 to form the EML.

The organic light-emitting device had a driving voltage of 6.14 V at a current density of 50 mA/cm², a high emission brightness of 7,804 cd/m², and an emission efficiency of 18.09 cd/A.

Example 3

An organic light-emitting device was manufactured in the same manner as in Example 1, except that Compound 43 was used instead of Compound 11 to form the EML.

The organic light-emitting device had a driving voltage of 6.15 V at a current density of 50 mA/cm², a high emission brightness of 7,856 cd/m², and an emission efficiency of 18.82 cd/A.

Example 4

An organic light-emitting device was manufactured in the same manner as in Example 1, except that Compound 56 was used instead of Compound 11 to form the EML.

The organic light-emitting device had a driving voltage of 6.54 V at a current density of 50 mA/cm², a high emission brightness of 8,357 cd/m², and an emission efficiency of 19.04 cd/A.

Example 5

An organic light-emitting device was manufactured in the same manner as in Example 1, except that Compound 74 was used instead of Compound 11 to form the EML.

The organic light-emitting device had a driving voltage of 6.65 V at a current density of 50 mA/cm², a high emission brightness of 8,571 cd/m², and an emission efficiency of 18.74 cd/A.

Example 6

An organic light-emitting device was manufactured in the same manner as in Example 1, except that Compound 82 was used instead of Compound 11 to form the HTL.

The organic light-emitting device had a driving voltage of 6.32 V at a current density of 50 mA/cm², a high emission brightness of 7,936 cd/m², and an emission efficiency of 18.14 cd/A.

Example 7

An organic light-emitting device was manufactured in the same manner as in Example 1, except that Compound 82 was used instead of Alq₃ to form the ETL.

The organic light-emitting device had a driving voltage of 6.38 V at a current density of 50 mA/cm², a high emission brightness of 8,576 cd/m², and an emission efficiency of 17.94 cd/A.

Comparative Example 1

An organic light-emitting device was manufactured in the same manner as in Example 1, except that C545T (as a green fluorescent dopant) was used instead of Compound 11 to form the EML.

The organic light-emitting device had a driving voltage of 7.85 V at a current density of 50 mA/cm², a high emission brightness of 5,641 cd/m², and an emission efficiency of 13.12 cd/A.

The organic light-emitting devices manufactured using the heterocyclic compounds of Formula 1 according to embodiments of the present invention had driving voltages that were lower by 1V or greater than devices using C545T, and thus had higher efficiency and good I-V-L characteristics. In particular, lifetime characteristics were markedly improved by 100% or greater in the organic light-emitting devices according to Examples 1 through 7 compared with the organic light-emitting device according to Comparative Example 1. The results are shown in Table 1 below.

TABLE 1

| | EML material or ETL material | Driving voltage | Current density | Brightness | Efficiency [%] | Emitted Light color | Half-life span (hr @ 100 mA/cm$^2$) |
|---|---|---|---|---|---|---|---|
| Example 1 | Compound 11 | 6.20 | 50 | 8,642 | 18.70 | green | 756 hr |
| Example 2 | Compound 29 | 6.14 | 50 | 7,804 | 18.09 | green | 824 hr |
| Example 3 | Compound 43 | 6.15 | 50 | 7,856 | 18.82 | green | 775 hr |
| Example 4 | Compound 56 | 6.54 | 50 | 8,357 | 19.04 | blue-green | 810 hr |
| Example 5 | Compound 74 | 6.65 | 50 | 8,571 | 18.74 | blue-green | 805 hr |
| Example 6 | Compound 82 | 6.32 | 50 | 7,936 | 18.14 | green | 747 hr |
| Example 7 | Compound 82 | 6.38 | 50 | 8,576 | 17.94 | green | 770 hr |
| Comparative Example 1 | C545T | 7.85 | 50 | 5,641 | 13.12 | green | 351 hr |

The heterocyclic compounds according to embodiments of the present invention have good electrical characteristics, charge transporting capabilities, light-emission capabilities, and high glass transition temperatures, and thus may be used as at least one of an electron transporting material or an emitting material for all-color fluorescent and phosphorescent devices, such as red, green, blue, and white fluorescent and phosphorescent devices. Thus, an organic light-emitting device with high-efficiency, low driving voltage, high luminance and long lifespan may be manufactured using the heterocylic compounds.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heterocyclic compound comprising a compound represented by Formula 1:

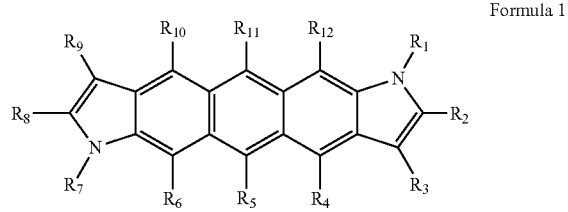

Formula 1 wherein each of $R_1$, $R_4$ through $R_7$, and $R_{10}$ through $R_{12}$ is independently selected from the group consisting of hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_5$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups, wherein each of $R_2$, $R_3$, $R_8$ and $R_9$ is independently selected from the group consisting of methyl groups and phenyl groups, and wherein two or more neighboring substituents selected from $R_1$, $R_4$ through $R_7$, and $R_{10}$ through $R_{12}$ may optionally bond to each other to form an aromatic ring.

2. The heterocyclic compound of claim 1, wherein each of $R_1$ and $R_7$ is independently selected from the group consisting of:

monocyclic to tetracyclic aryl groups and $C_{12}$-$C_{50}$ arylamine groups selected from the group consisting of unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups;

substituted monocyclic to tetracyclic aryl groups selected from the group consisting of phenyl groups, naphthyl groups, biphenyl groups, terphenyl groups, anthracenyl groups, fluorenyl groups, carbazolyl groups, and pyrenyl groups having at least one substituent selected from the group consisting of $C_1$-$C_5$ alkyl groups, $C_1$-$C_5$ alkoxy groups, cyano groups, amine groups, phenoxy groups, phenyl groups, naphthyl groups, and halogen groups;

substituted $C_{12}$-$C_{50}$ arylamine groups having at least one substituent selected from the group consisting of $C_1$-$C_5$ alkyl groups, $C_1$-$C_4$ alkoxy groups, cyano groups, amine groups, phenoxy groups, phenyl groups, and halogen groups.

3. The heterocyclic compound of claim 1, wherein $R_1$ and $R_7$ are the same, $R_2$, $R_3$, $R_8$ and $R_9$ are the same, or $R_5$ and $R_{11}$ are the same.

4. The heterocyclic compound of claim 1, wherein the compound represented by Formula 1 is selected from the group consisting of Compounds 11, 29, 43, 56, 74 and 82:

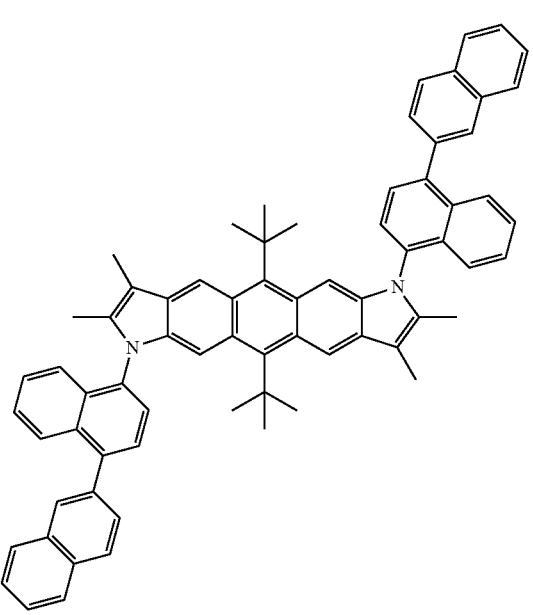

11

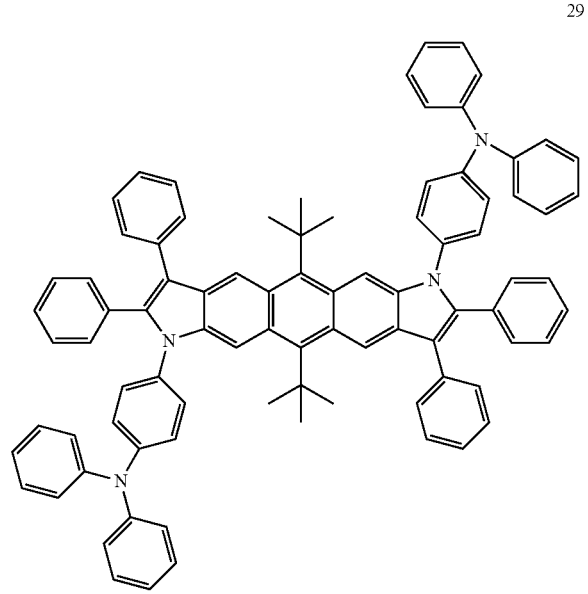

5. A heterocyclic compound comprising a compound represented by Formula 1:

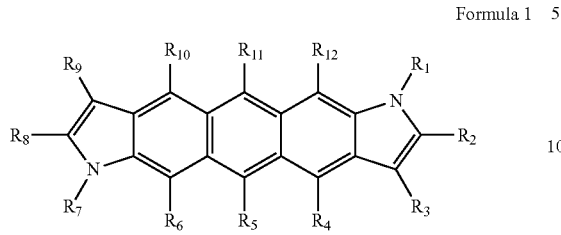

Formula 1 wherein each of $R_1$ through $R_4$, $R_6$ through $R_{10}$, and $R_{12}$ is independently selected from the group consisting of hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups, wherein two or more neighboring substituents selected from $R_1$ through $R_4$, $R_6$ through $R_l o$ and $R_{12}$ may optionally bond to each other to form an aromatic ring, and wherein each of $R_5$ and $R_{11}$ is independently selected from the group consisting of t-butyl groups, phenyl groups, naphthyl groups, and fluorenyl groups.

6. An organic light-emitting device comprising:
a first electrode;
a second electrode; and
an organic layer between the first electrode and the second electrode,
wherein the organic layer comprises a heterocyclic compound of comprising a compound represented by Formula 1:

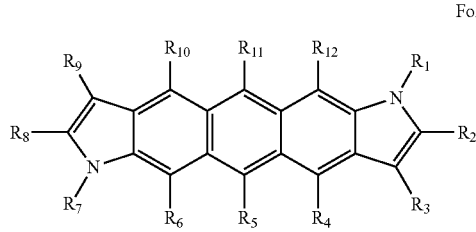

Formula 1 wherein each of $R_1$ through $R_{12}$ is independently selected from the group consisting of hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted alkoxy groups, substituted and unsubstituted $C_5$-$O_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups, and wherein two or more neighboring substituents selected from $R_1$ through $R_{12}$ may optionally bond to each other to form an aromatic ring.

7. The organic light-emitting device of claim 6, wherein the organic layer comprises a hole injection layer or a hole transport layer.

8. The organic light-emitting device of claim 6, wherein the organic layer comprises a single film configured for electron injection and electron transport.

9. The organic light-emitting device of claim 6, wherein the organic layer comprises an emission layer.

10. The organic light-emitting device of claim 6, wherein the organic layer comprises an emission layer, and the heterocyclic compound is a host for a fluorescent or phosphorescent device.

11. The organic light-emitting device of claim 6, wherein the organic layer comprises an emission layer, and the heterocyclic compound is a fluorescent dopant.

12. The organic light-emitting device of claim 6, wherein the organic layer comprises an electron injection layer or an electron transport layer, and an emission layer comprising an anthracene compound or an arylamine compound or a styryl compound.

13. The organic light-emitting device of claim 6, wherein the organic layer comprises an emission layer, and an electron injection layer or an electron transport layer, wherein the emission layer comprises a red emission layer, a green emission layer, a blue emission layer or a white emission layer that comprises a phosphorescent compound.

14. The organic light-emitting device of claim 6, wherein the organic layer comprises at least one layer selected from the group consisting of a hole injection layer, a hole transport layer, an electron blocking layer, an emission layer, a hole blocking layer, an electron transport layer, and an electron injection layer.

15. The organic light-emitting device of claim 14, wherein the organic light-emitting device comprises a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure.

16. A flat panel display device comprising the organic light-emitting device of claim 6, wherein the first electrode of the organic light-emitting device is electrically connected to a source electrode or a drain electrode of a thin-film transistor.

17. The organic light-emitting device of claim 6,
wherein the at least one layer is formed using a wet process.

* * * * *

UNITED STATES PATENT AND TRADEMARK OFFICE
CERTIFICATE OF CORRECTION

PATENT NO. : 8,535,814 B2
APPLICATION NO. : 12/854065
DATED : September 17, 2013
INVENTOR(S) : Yoon-Hyun Kwak et al.

It is certified that error appears in the above-identified patent and that said Letters Patent is hereby corrected as shown below:

In the Claims

Col. 123, line 51, Claim 1    Delete "$C_5$-$C_{50}$ alkoxy",
Insert --$C_1$-$C_{50}$ alkoxy--

Col. 126, Claim 4, Formula 74

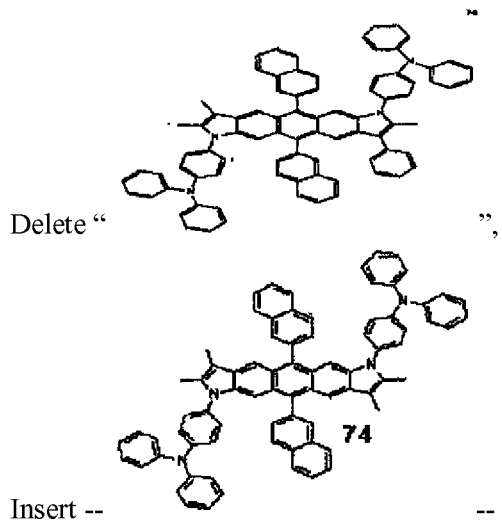

Delete " ",

Insert -- --

Col. 126, Claim 4, Formula 82

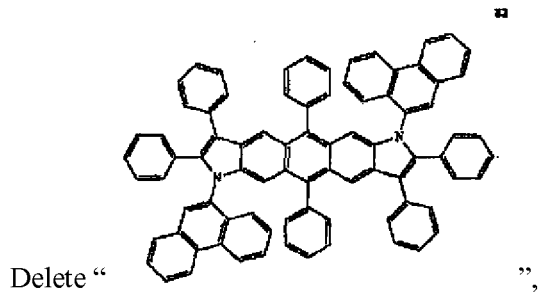

Delete " ",

Signed and Sealed this
Thirtieth Day of December, 2014

Michelle K. Lee
*Deputy Director of the United States Patent and Trademark Office*

CERTIFICATE OF CORRECTION (continued)
U.S. Pat. No. 8,535,814 B2

| | |
|---|---|
| | Insert -- 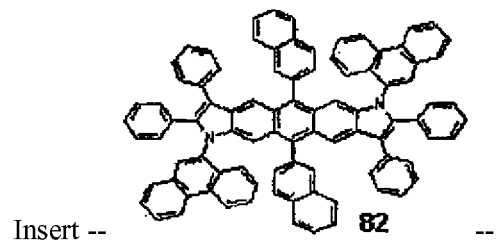 -- |
| Col. 127, line 30, Claim 5 | Delete "R$_i$o", <br> Insert --R$_{10}$-- |
| Col. 127, line 41, Claim 6 | Delete "compound of comprising", <br> Insert --compound comprising-- |
| Col. 127, line 59, Claim 6 | Delete "unsubstituted alkoxy", <br> Insert --unsubstituted C$_1$-C$_{50}$ alkoxy-- |
| Col. 128, line 1, Claim 6 | Delete "C$_5$-0$_{50}$", <br> Insert --C$_5$-C$_{50}$-- |